(12) United States Patent
Tanis et al.

(10) Patent No.: US 10,639,502 B2
(45) Date of Patent: *May 5, 2020

(54) MEDICAL DEVICE

(71) Applicant: SMITH & NEPHEW, INC., Memphis, TN (US)

(72) Inventors: Kevin J. Tanis, Collierville, TN (US); Jin Zhang, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 505 days.

This patent is subject to a terminal disclaimer.

(21) Appl. No.: 15/482,449

(22) Filed: Apr. 7, 2017

(65) Prior Publication Data

US 2017/0209718 A1 Jul. 27, 2017

Related U.S. Application Data

(63) Continuation of application No. 15/357,883, filed on Nov. 21, 2016, now Pat. No. 10,086,216, which is a
(Continued)

(51) Int. Cl.
*A61N 7/00* (2006.01)
*G16H 40/63* (2018.01)
(Continued)

(52) U.S. Cl.
CPC ............ *A61N 7/00* (2013.01); *A61B 5/1172* (2013.01); *A61B 34/25* (2016.02); *G06F 19/00* (2013.01);
(Continued)

(58) Field of Classification Search
CPC ............ A61N 7/00; A61N 2007/0078; A61N 2007/0013; G06F 19/00; G06F 19/3418;
(Continued)

(56) References Cited

U.S. PATENT DOCUMENTS

| 695,270 A | 3/1902 | Beringer |
| 3,194,239 A | 7/1965 | Sullivan |
| (Continued) | | |

FOREIGN PATENT DOCUMENTS

| CA | 2 819 475 | 6/2012 |
| CN | 102961815 | 3/2013 |
| (Continued) | | |

OTHER PUBLICATIONS

Australian Office Action, re AU Application No. 2011316599, dated Jan. 9, 2015.
(Continued)

*Primary Examiner* — Sanjay Cattungal
(74) *Attorney, Agent, or Firm* — Knobbe, Martens, Olson & Bear LLP

(57) ABSTRACT

A medical device includes a treatment module configured to apply a treatment to a patient. The medical device includes an interface configured to operatively connect to a removable storage device storing authorization data that identifies a level of treatment authorization. The medical device includes a processing device configured to perform operations in response to receiving user input indicating a treatment should be initiated. The operations include determining whether the removable storage device is valid for use with the medical device. If the removable storage device is determined to be valid, the authorization data is accessed. The processing device determines whether the treatment is authorized based on the accessed authorization data. If the treatment is determined to be authorized, the treatment module is controlled to apply the treatment. If the treatment is determined to not be authorized, the treatment module is controlled such that the treatment is not applied.

22 Claims, 20 Drawing Sheets

Related U.S. Application Data continuation of application No. 13/271,870, filed on Oct. 12, 2011, now Pat. No. 9,526,920.

(60) Provisional application No. 61/483,445, filed on May 6, 2011, provisional application No. 61/405,757, filed on Oct. 22, 2010, provisional application No. 61/405,405, filed on Oct. 21, 2010, provisional application No. 61/392,154, filed on Oct. 12, 2010.

(51) Int. Cl.
   *A61B 34/00* (2016.01)
   *G06F 19/00* (2018.01)
   *A61B 5/1172* (2016.01)
   *A61B 90/90* (2016.01)
   *A61B 90/00* (2016.01)

(52) U.S. Cl.
   CPC ......... *G06F 19/3418* (2013.01); *G16H 40/63* (2018.01); *A61B 90/90* (2016.02); *A61B 2034/258* (2016.02); *A61B 2090/0803* (2016.02); *A61M 2205/6009* (2013.01); *A61N 2007/0013* (2013.01); *A61N 2007/0078* (2013.01)

(58) Field of Classification Search
   CPC ....... G16H 40/63; A61B 5/1172; A61B 34/25; A61B 2090/0803; A61B 90/90; A61B 2034/258; A61M 2205/6009
   See application file for complete search history.

(56) References Cited

U.S. PATENT DOCUMENTS

| | | |
|---|---|---|
| 4,642,769 A | 2/1987 | Petrofsky |
| 4,832,299 A | 5/1989 | Gorton et al. |
| 4,899,839 A | 2/1990 | Dessertine et al. |
| 5,016,172 A | 5/1991 | Dessertine |
| 5,158,528 A | 10/1992 | Walker et al. |
| 5,174,533 A | 12/1992 | Pryor et al. |
| 5,215,523 A | 6/1993 | Williams et al. |
| 5,219,428 A | 6/1993 | Stern |
| 5,419,768 A | 5/1995 | Kayser |
| 5,449,347 A | 9/1995 | Preen et al. |
| 5,466,229 A | 11/1995 | Elson |
| 5,473,536 A | 12/1995 | Wimmer |
| 5,556,372 A | 9/1996 | Talish et al. |
| 5,582,601 A | 12/1996 | Wortrich et al. |
| 5,584,824 A | 12/1996 | Gillette et al. |
| 5,590,658 A | 1/1997 | Chiang et al. |
| 5,599,308 A | 2/1997 | Krupa |
| 5,622,429 A | 4/1997 | Heinze |
| 5,634,939 A | 6/1997 | Kuster et al. |
| 5,656,027 A | 8/1997 | Ellingboe |
| 5,669,892 A | 9/1997 | Keogh et al. |
| 5,687,717 A | 11/1997 | Halpern et al. |
| 5,693,013 A | 12/1997 | Geuder |
| 5,748,103 A | 5/1998 | Flach et al. |
| 5,779,207 A | 7/1998 | Danby |
| D408,625 S | 4/1999 | Barker |
| 5,933,136 A | 8/1999 | Brown |
| 5,956,023 A | 9/1999 | Lyle et al. |
| 5,960,403 A | 9/1999 | Brown et al. |
| 5,989,234 A | 11/1999 | Valerio et al. |
| 6,018,289 A | 1/2000 | Sekura et al. |
| 6,055,506 A | 4/2000 | Frasca et al. |
| 6,161,095 A | 12/2000 | Brown |
| 6,174,306 B1 | 1/2001 | Fleischmann |
| 6,228,056 B1 | 5/2001 | Boehringer et al. |
| 6,241,739 B1 | 6/2001 | Waldron |
| 6,250,482 B1 | 6/2001 | Want et al. |
| 6,261,249 B1 | 7/2001 | Talish et al. |
| 6,270,460 B1 | 8/2001 | McCartan et al. |
| 6,308,089 B1 | 10/2001 | von der Ruhr et al. |
| 6,336,900 B1 | 1/2002 | Alleckson et al. |
| 6,353,445 B1 | 3/2002 | Babula et al. |
| 6,375,614 B1 | 4/2002 | Braun et al. |
| 6,385,622 B2 | 5/2002 | Bouve et al. |
| 6,387,092 B1 | 5/2002 | Burnside et al. |
| 6,406,426 B1 | 6/2002 | Reuss et al. |
| 6,413,213 B1 | 7/2002 | Essenpreis et al. |
| 6,434,572 B2 | 8/2002 | Derzay et al. |
| 6,460,041 B2 | 10/2002 | Lloyd et al. |
| 6,572,530 B1 | 6/2003 | Araki et al. |
| 6,574,518 B1 | 6/2003 | Lounsberry et al. |
| 6,577,893 B1 | 6/2003 | Besson et al. |
| 6,605,032 B2 | 8/2003 | Benkowski et al. |
| 6,640,145 B2 | 10/2003 | Hoffberg et al. |
| 6,640,246 B1 | 10/2003 | Gary, Jr. et al. |
| 6,675,131 B2 | 1/2004 | Hahn et al. |
| 6,681,003 B2 | 1/2004 | Linder et al. |
| 6,723,046 B2 | 4/2004 | Lichtenstein et al. |
| 6,738,052 B1 | 5/2004 | Manke et al. |
| 6,747,556 B2 | 6/2004 | Medema et al. |
| 6,766,218 B2 | 7/2004 | Rosenblum |
| 6,779,024 B2 | 8/2004 | Delahuerga et al. |
| 6,782,285 B2 | 8/2004 | Birkenbach et al. |
| 6,792,306 B2 | 9/2004 | Henley et al. |
| 6,811,533 B2 | 11/2004 | Lebel et al. |
| 6,868,528 B2 | 3/2005 | Roberts et al. |
| 6,871,211 B2 | 3/2005 | Labounty et al. |
| 6,909,974 B2 | 6/2005 | Yung et al. |
| 6,912,481 B2 | 6/2005 | Breunissen et al. |
| 6,961,731 B2 | 11/2005 | Holbrook et al. |
| 7,004,915 B2 | 2/2006 | Boynton et al. |
| 7,022,113 B2 | 4/2006 | Lockwood et al. |
| 7,048,687 B1 | 5/2006 | Reuss et al. |
| 7,051,012 B2 | 5/2006 | Cole et al. |
| 7,066,883 B2 | 6/2006 | Schmidt et al. |
| 7,103,578 B2 | 9/2006 | Beck et al. |
| 7,108,683 B2 | 9/2006 | Zamierowski et al. |
| 7,120,488 B2 | 10/2006 | Nova et al. |
| 7,128,735 B2 | 10/2006 | Weston |
| 7,133,869 B2 | 11/2006 | Bryan et al. |
| 7,167,858 B2 | 1/2007 | Naeymi-Rad et al. |
| 7,212,829 B1 | 5/2007 | Lau et al. |
| 7,264,591 B2 | 9/2007 | Brown et al. |
| 7,273,483 B2 | 9/2007 | Wiener et al. |
| 7,304,573 B2 | 12/2007 | Postma et al. |
| 7,311,665 B2 | 12/2007 | Hawthorne et al. |
| 7,333,002 B2 | 2/2008 | Bixler et al. |
| D565,177 S | 3/2008 | Locke et al. |
| 7,353,179 B2 | 4/2008 | Ott et al. |
| 7,361,184 B2 | 4/2008 | Joshi |
| 7,364,554 B2 | 4/2008 | Bolze et al. |
| 7,384,267 B1 | 6/2008 | Franks et al. |
| 7,395,214 B2 | 7/2008 | Shillingburg |
| 7,430,598 B2 | 9/2008 | Raden et al. |
| D581,042 S | 11/2008 | Randolph et al. |
| D581,522 S | 11/2008 | Randolph et al. |
| 7,448,265 B2 | 11/2008 | Smyser et al. |
| 7,451,002 B2 | 11/2008 | Choubey et al. |
| 7,457,804 B2 | 11/2008 | Uber et al. |
| 7,460,872 B2 | 12/2008 | Millard et al. |
| 7,505,815 B2 | 3/2009 | Lee et al. |
| D590,934 S | 4/2009 | Randolph et al. |
| 7,534,240 B1 | 5/2009 | Johnson et al. |
| 7,553,306 B1 | 6/2009 | Hunt et al. |
| 7,569,742 B2 | 8/2009 | Haggstrom et al. |
| 7,594,901 B2 | 9/2009 | Hopkins et al. |
| D602,582 S | 10/2009 | Pidgeon et al. |
| D602,583 S | 10/2009 | Pidgeon et al. |
| 7,598,855 B2 | 10/2009 | Scalisi et al. |
| 7,611,500 B1 | 11/2009 | Lina et al. |
| 7,615,036 B2 | 11/2009 | Joshi et al. |
| 7,627,334 B2 | 12/2009 | Cohen et al. |
| 7,639,120 B2 | 12/2009 | Sekura |
| 7,649,449 B2 | 1/2010 | Fenske et al. |
| 7,670,323 B2 | 3/2010 | Hunt et al. |
| 7,671,733 B2 | 3/2010 | McNeal et al. |
| 7,684,999 B2 | 3/2010 | Brown et al. |
| 7,699,823 B2 | 4/2010 | Haggstrom et al. |
| 7,723,560 B2 | 5/2010 | Lockwood et al. |

(56) References Cited

U.S. PATENT DOCUMENTS

| | | |
|---|---|---|
| 7,734,764 B2 | 6/2010 | Weiner et al. |
| 7,749,164 B2 | 7/2010 | Davis et al. |
| 7,753,894 B2 | 7/2010 | Blott et al. |
| 7,770,855 B2 | 8/2010 | Locke et al. |
| 7,776,028 B2 | 8/2010 | Miller et al. |
| 7,779,153 B2 | 8/2010 | Van den Heuvel et al. |
| 7,785,277 B2 | 8/2010 | Babaev et al. |
| 7,789,828 B2 | 9/2010 | Clapp et al. |
| D625,801 S | 10/2010 | Pidgeon et al. |
| 7,827,148 B2 | 11/2010 | Mori et al. |
| 7,846,141 B2 | 12/2010 | Weston |
| 7,857,806 B2 | 12/2010 | Karpowicz et al. |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,912,823 B2 | 3/2011 | Ferrari et al. |
| D635,588 S | 4/2011 | Sprules |
| 7,925,603 B1 | 4/2011 | Laidig et al. |
| 7,927,319 B2 | 4/2011 | Lawhorn |
| 7,933,817 B2 | 4/2011 | Radl et al. |
| 7,945,452 B2 | 5/2011 | Fathallah et al. |
| 7,955,281 B2 | 6/2011 | Pedersen et al. |
| 7,956,727 B2 | 6/2011 | Loncar |
| 7,976,519 B2 | 7/2011 | Bubb et al. |
| 7,981,098 B2 | 7/2011 | Boehringer et al. |
| D644,250 S | 8/2011 | Barber et al. |
| 7,988,850 B2 | 8/2011 | Roncadi et al. |
| 8,007,481 B2 | 8/2011 | Schuessler et al. |
| 8,015,443 B2 | 9/2011 | Adachi et al. |
| 8,015,972 B2 | 9/2011 | Pirzada |
| 8,019,618 B2 | 9/2011 | Brown et al. |
| 8,048,046 B2 | 11/2011 | Hudspeth et al. |
| 8,054,950 B1 | 11/2011 | Hung et al. |
| 8,061,360 B2 | 11/2011 | Locke et al. |
| 8,066,243 B2 | 11/2011 | Svedman et al. |
| 8,094,009 B2 | 1/2012 | Allen et al. |
| 8,096,515 B2 | 1/2012 | Locke et al. |
| 8,100,873 B2 | 1/2012 | Jaeb et al. |
| 8,105,295 B2 | 1/2012 | Blott et al. |
| 8,126,735 B2 | 2/2012 | Dicks et al. |
| 8,130,095 B2 | 3/2012 | Allen et al. |
| 8,131,472 B2 | 3/2012 | Chow et al. |
| 8,180,750 B2 | 5/2012 | Wilmering et al. |
| 8,190,445 B2 | 5/2012 | Kuth et al. |
| 8,190,448 B2 | 5/2012 | Bajars et al. |
| 8,216,198 B2 | 7/2012 | Heagle et al. |
| 8,228,188 B2 | 7/2012 | Key et al. |
| 8,235,955 B2 | 8/2012 | Blott et al. |
| 8,240,470 B2 | 8/2012 | Pidgeon et al. |
| 8,246,606 B2 | 8/2012 | Stevenson et al. |
| 8,246,607 B2 | 8/2012 | Karpowicz et al. |
| 8,249,894 B2 | 8/2012 | Brown et al. |
| 8,255,241 B2 | 8/2012 | Cafer et al. |
| 8,257,328 B2 | 9/2012 | Augustine et al. |
| 8,260,630 B2 | 9/2012 | Brown et al. |
| 8,267,918 B2 | 9/2012 | Johnson et al. |
| 8,280,682 B2 | 10/2012 | Vock et al. |
| 8,284,024 B2 | 10/2012 | Toleti et al. |
| 8,284,046 B2 | 10/2012 | Allen et al. |
| 8,290,792 B2 | 10/2012 | Sekura et al. |
| 8,291,337 B2 | 10/2012 | Gannin et al. |
| 8,294,586 B2 | 10/2012 | Pidgeon et al. |
| 8,298,200 B2 | 10/2012 | Vess et al. |
| 8,308,714 B2 | 11/2012 | Weston et al. |
| 8,317,752 B2 | 11/2012 | Cozmi et al. |
| 8,317,774 B2 | 11/2012 | Adahan |
| 8,323,263 B2 | 12/2012 | Wood et al. |
| 8,332,233 B2 | 12/2012 | Ott et al. |
| 8,333,744 B2 | 12/2012 | Hartwell et al. |
| 8,334,768 B2 | 12/2012 | Eaton et al. |
| 8,337,482 B2 | 12/2012 | Wood et al. |
| 8,360,975 B1 | 1/2013 | Schwieterman et al. |
| 8,366,692 B2 | 2/2013 | Weston |
| 8,377,016 B2 | 2/2013 | Argenta et al. |
| 8,377,018 B2 | 2/2013 | Bendele et al. |
| 8,400,295 B1 | 3/2013 | Khaira |
| 8,403,902 B2 | 3/2013 | Locke et al. |
| 8,409,170 B2 | 4/2013 | Locke et al. |
| 8,422,377 B2 | 4/2013 | Weiner et al. |
| 8,424,517 B2 | 4/2013 | Sutherland et al. |
| 8,436,871 B2 | 5/2013 | Alberte et al. |
| 8,439,882 B2 | 5/2013 | Kelch |
| 8,444,392 B2 | 5/2013 | Turner et al. |
| 8,457,740 B2 | 6/2013 | Osche et al. |
| 8,480,641 B2 | 7/2013 | Jacobs |
| 8,494,349 B2 | 7/2013 | Gordon |
| 8,515,776 B2 | 8/2013 | Schoenberg et al. |
| 8,532,764 B2 | 9/2013 | Duke et al. |
| 8,540,688 B2 | 9/2013 | Eckstein et al. |
| 8,545,483 B2 | 10/2013 | Schwabe et al. |
| 8,552,880 B2 | 10/2013 | Kopp et al. |
| 8,554,195 B2 | 10/2013 | Rao et al. |
| 8,558,964 B2 | 10/2013 | Bedingfield |
| 8,560,082 B2 | 10/2013 | Wei et al. |
| 8,577,694 B2 | 11/2013 | Kanaan et al. |
| 8,595,553 B2 | 11/2013 | Goertler et al. |
| 8,604,265 B2 | 12/2013 | Locke et al. |
| 8,617,129 B2 | 12/2013 | Hartwell |
| 8,622,981 B2 | 1/2014 | Hartwell et al. |
| 8,626,342 B2 | 1/2014 | Williams, Jr. et al. |
| 8,626,526 B2 | 1/2014 | Lemke et al. |
| 8,628,258 B2 | 1/2014 | Vogt |
| 8,632,485 B2 | 1/2014 | Schlaeper et al. |
| 8,641,693 B2 | 2/2014 | Locke et al. |
| 8,652,111 B2 | 2/2014 | Pratt et al. |
| 8,659,420 B2 | 2/2014 | Salvat et al. |
| 8,668,677 B2 | 3/2014 | Eckstein et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,747,376 B2 | 6/2014 | Locke et al. |
| 8,756,078 B2 | 6/2014 | Collins et al. |
| 8,768,441 B2 | 7/2014 | De Zwart et al. |
| 8,771,259 B2 | 7/2014 | Karpowicz et al. |
| 8,781,847 B2 | 7/2014 | Simms et al. |
| 8,795,171 B2 | 8/2014 | Adamczyk et al. |
| 8,795,244 B2 | 8/2014 | Randolph et al. |
| 8,798,284 B2 | 8/2014 | Cartwright et al. |
| 8,814,841 B2 | 8/2014 | Hartwell |
| 8,814,842 B2 | 8/2014 | Coulthard et al. |
| 8,827,983 B2 | 9/2014 | Braga et al. |
| 8,843,327 B2 | 9/2014 | Vernon-Harcourt et al. |
| 8,845,603 B2 | 9/2014 | Middleton et al. |
| 8,845,604 B2 | 9/2014 | Croizat et al. |
| 8,852,149 B2 | 10/2014 | Weston et al. |
| 8,858,517 B2 | 10/2014 | Pan et al. |
| 8,862,393 B2 | 10/2014 | Zhou et al. |
| 8,868,794 B2 | 10/2014 | Masoud et al. |
| 8,870,812 B2 | 10/2014 | Alberti et al. |
| 8,874,035 B2 | 10/2014 | Sherman et al. |
| 8,887,100 B1 | 11/2014 | Cook et al. |
| 8,890,656 B2 | 11/2014 | Pendse et al. |
| 8,897,198 B2 | 11/2014 | Gaines et al. |
| 8,902,278 B2 | 12/2014 | Pinter et al. |
| 8,905,959 B2 | 12/2014 | Basaglia |
| 8,905,985 B2 | 12/2014 | Allen et al. |
| 8,909,595 B2 | 12/2014 | Gandy et al. |
| 8,926,574 B2 | 1/2015 | Croizat et al. |
| 8,943,168 B2 | 1/2015 | Wiesner et al. |
| 8,945,030 B2 | 2/2015 | Weston |
| 8,945,073 B2 | 2/2015 | Croizat et al. |
| 8,945,074 B2 | 2/2015 | Buan et al. |
| 8,947,237 B2 | 2/2015 | Margon et al. |
| 8,961,497 B2 | 2/2015 | Ryu et al. |
| 8,974,429 B2 | 3/2015 | Gordon et al. |
| 8,978,026 B2 | 3/2015 | Charlton et al. |
| 8,996,393 B2 | 3/2015 | Sobie |
| 9,017,286 B2 | 4/2015 | Kamen et al. |
| 9,019,681 B2 | 4/2015 | Locke et al. |
| 9,023,002 B2 | 5/2015 | Robinson et al. |
| 9,047,648 B1 | 6/2015 | Lekutai et al. |
| 9,058,634 B2 | 6/2015 | Buan et al. |
| 9,067,003 B2 | 6/2015 | Buan et al. |
| 9,084,845 B2 | 7/2015 | Adie et al. |

(56) References Cited

U.S. PATENT DOCUMENTS

| | | |
|---|---|---|
| 9,098,114 B2 | 8/2015 | Potter et al. |
| 9,105,006 B2 | 8/2015 | Williamson et al. |
| 9,135,398 B2 | 9/2015 | Kaib et al. |
| 9,215,581 B2 | 12/2015 | Julian et al. |
| 9,268,827 B2 | 2/2016 | Fernandez et al. |
| 9,286,443 B2 | 3/2016 | Ford et al. |
| 9,323,893 B2 | 4/2016 | Berry et al. |
| 9,408,954 B2 | 8/2016 | Gordon et al. |
| 9,436,800 B2 | 9/2016 | Forrester et al. |
| 9,526,920 B2 | 12/2016 | Tanis et al. |
| 9,539,373 B2 | 1/2017 | Jones et al. |
| 9,658,066 B2 | 5/2017 | Yuen et al. |
| 9,662,438 B2 | 5/2017 | Kamen et al. |
| 9,741,084 B2 | 8/2017 | Holmes et al. |
| 9,792,660 B2 | 10/2017 | Cannon et al. |
| 9,818,164 B2 | 11/2017 | Nolte et al. |
| 9,878,081 B2 | 1/2018 | Leiendecker et al. |
| 9,990,466 B2 | 6/2018 | Debusk et al. |
| 10,061,894 B2 | 8/2018 | Sethumadhavan et al. |
| 10,173,008 B2 | 1/2019 | Simpson et al. |
| 10,231,878 B2 | 3/2019 | Hartwell et al. |
| 2001/0013822 A1 | 8/2001 | Nazarian et al. |
| 2001/0031944 A1 | 10/2001 | Peterson et al. |
| 2001/0041831 A1 | 11/2001 | Starkweather et al. |
| 2001/0049609 A1 | 12/2001 | Girouard et al. |
| 2002/0002326 A1 | 1/2002 | Causey, III et al. |
| 2002/0002368 A1 | 1/2002 | Tomita et al. |
| 2002/0013516 A1 | 1/2002 | Freyre et al. |
| 2002/0015034 A1 | 2/2002 | Malmborg |
| 2002/0026160 A1 | 2/2002 | Takahashi et al. |
| 2002/0049562 A1 | 4/2002 | Hahn |
| 2002/0065685 A1 | 5/2002 | Sasaki et al. |
| 2002/0082568 A1 | 6/2002 | Yam |
| 2002/0087360 A1 | 7/2002 | Pettit |
| 2002/0120467 A1 | 8/2002 | Buanes |
| 2002/0128804 A1 | 9/2002 | Geva |
| 2002/0128869 A1 | 9/2002 | Kuth |
| 2002/0135336 A1 | 9/2002 | Zhou et al. |
| 2002/0161317 A1 | 10/2002 | Risk et al. |
| 2002/0177757 A1 | 11/2002 | Britton |
| 2002/0184055 A1 | 12/2002 | Naghavi et al. |
| 2002/0193679 A1 | 12/2002 | Malave et al. |
| 2002/0198505 A1 | 12/2002 | Want et al. |
| 2003/0009244 A1 | 1/2003 | Engleson et al. |
| 2003/0018395 A1 | 1/2003 | Crnkovich et al. |
| 2003/0018736 A1 | 1/2003 | Christ et al. |
| 2003/0023460 A1 | 1/2003 | Ackermann et al. |
| 2003/0028175 A1 | 2/2003 | D'Antonio |
| 2003/0036683 A1 | 2/2003 | Kehr et al. |
| 2003/0093041 A1 | 5/2003 | Risk, Jr. et al. |
| 2003/0093181 A1 | 5/2003 | Rosenblum |
| 2003/0095648 A1 | 5/2003 | Kaib et al. |
| 2003/0105389 A1 | 6/2003 | Noonan et al. |
| 2003/0105649 A1 | 6/2003 | Sheiner et al. |
| 2003/0128125 A1 | 7/2003 | Burbank et al. |
| 2003/0130567 A1 | 7/2003 | Mault et al. |
| 2003/0164600 A1 | 9/2003 | Dunn et al. |
| 2003/0176183 A1 | 9/2003 | Drucker et al. |
| 2003/0182158 A1 | 9/2003 | Son |
| 2003/0199794 A1 | 10/2003 | Sakurai et al. |
| 2003/0214412 A1 | 11/2003 | Ho et al. |
| 2003/0221687 A1 | 12/2003 | Kaigler |
| 2003/0229518 A1 | 12/2003 | Abraham-Fuchs |
| 2003/0233071 A1 | 12/2003 | Gillespie, Jr. et al. |
| 2003/0236450 A1 | 12/2003 | Kocinski |
| 2004/0006492 A1 | 1/2004 | Watanabe |
| 2004/0015132 A1 | 1/2004 | Brown |
| 2004/0019464 A1 | 1/2004 | Martucci et al. |
| 2004/0039255 A1 | 2/2004 | Simonsen et al. |
| 2004/0049172 A1 | 3/2004 | Root et al. |
| 2004/0054338 A1 | 3/2004 | Bybordi et al. |
| 2004/0054775 A1 | 3/2004 | Poliac et al. |
| 2004/0059284 A1 | 3/2004 | Nash et al. |
| 2004/0064132 A1 | 4/2004 | Boehringer et al. |
| 2004/0078223 A1 | 4/2004 | Sacco et al. |
| 2004/0102743 A1 | 5/2004 | Walker |
| 2004/0120825 A1 | 6/2004 | Bouton et al. |
| 2004/0143458 A1 | 7/2004 | Pulkkinen et al. |
| 2004/0158193 A1 | 8/2004 | Bui et al. |
| 2004/0167802 A1 | 8/2004 | Takada et al. |
| 2004/0167804 A1 | 8/2004 | Simpson et al. |
| 2004/0171982 A1 | 9/2004 | Danchin |
| 2004/0172301 A1 | 9/2004 | Mihai et al. |
| 2004/0176983 A1 | 9/2004 | Birkett et al. |
| 2004/0181314 A1 | 9/2004 | Zaleski |
| 2004/0181433 A1 | 9/2004 | Blair |
| 2004/0193449 A1 | 9/2004 | Wildman et al. |
| 2004/0204962 A1 | 10/2004 | Howser et al. |
| 2004/0227737 A1 | 11/2004 | Novak et al. |
| 2004/0249673 A1 | 12/2004 | Smith |
| 2005/0011282 A1 | 1/2005 | Voege et al. |
| 2005/0022274 A1 | 1/2005 | Campbell et al. |
| 2005/0027311 A1 | 2/2005 | Wiener et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065471 A1 | 3/2005 | Kuntz |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0108190 A1 | 5/2005 | Conkel |
| 2005/0114176 A1 | 5/2005 | Dominick et al. |
| 2005/0116126 A1 | 6/2005 | Ugent et al. |
| 2005/0119914 A1 | 6/2005 | Batch |
| 2005/0124966 A1 | 6/2005 | Karpowicz et al. |
| 2005/0187528 A1 | 8/2005 | Berg |
| 2005/0209560 A1 | 9/2005 | Boukhny et al. |
| 2005/0222873 A1 | 10/2005 | Nephin et al. |
| 2005/0230575 A1 | 10/2005 | Zelenski |
| 2005/0240111 A1 | 10/2005 | Chung |
| 2005/0256447 A1 | 11/2005 | Richardson et al. |
| 2005/0261805 A1 | 11/2005 | Mori et al. |
| 2005/0283382 A1 | 12/2005 | Donoghue et al. |
| 2006/0004604 A1 | 1/2006 | White |
| 2006/0020161 A1 | 1/2006 | Mageras et al. |
| 2006/0029675 A1 | 2/2006 | Ginther |
| 2006/0064323 A1 | 3/2006 | Alleckson et al. |
| 2006/0064491 A1 | 3/2006 | Ebert et al. |
| 2006/0085393 A1 | 4/2006 | Modesitt |
| 2006/0089539 A1 | 4/2006 | Miodownik et al. |
| 2006/0089544 A1 | 4/2006 | Williams, Jr. et al. |
| 2006/0095853 A1 | 5/2006 | Amyot et al. |
| 2006/0132283 A1 | 6/2006 | Eberhart et al. |
| 2006/0144440 A1 | 7/2006 | Merkle |
| 2006/0149171 A1 | 7/2006 | Vogel et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0224051 A1 | 10/2006 | Teller et al. |
| 2006/0229557 A1 | 10/2006 | Fathallah et al. |
| 2006/0246922 A1 | 11/2006 | Gasbarro et al. |
| 2006/0255935 A1 | 11/2006 | Scalisi et al. |
| 2007/0005029 A1 | 1/2007 | Hopkins et al. |
| 2007/0016152 A1 | 1/2007 | Karpowicz et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0038044 A1 | 2/2007 | Dobbles et al. |
| 2007/0052683 A1 | 3/2007 | Knott et al. |
| 2007/0055209 A1 | 3/2007 | Patel et al. |
| 2007/0078444 A1 | 4/2007 | Larsson |
| 2007/0100403 A1 | 5/2007 | Felice et al. |
| 2007/0118096 A1 | 5/2007 | Smith et al. |
| 2007/0118397 A1 | 5/2007 | Williams et al. |
| 2007/0136099 A1 | 6/2007 | Neligh et al. |
| 2007/0138069 A1 | 6/2007 | Roncadi et al. |
| 2007/0156186 A1 | 7/2007 | Lee et al. |
| 2007/0156456 A1 | 7/2007 | McGillin et al. |
| 2007/0173708 A9 | 7/2007 | Dobbles et al. |

(56) References Cited

U.S. PATENT DOCUMENTS

| | | |
|---|---|---|
| 2007/0179460 A1 | 8/2007 | Adahan |
| 2007/0180904 A1 | 8/2007 | Gao |
| 2007/0197881 A1 | 8/2007 | Wolf et al. |
| 2007/0219480 A1 | 9/2007 | Kamen et al. |
| 2007/0219826 A1 | 9/2007 | Brodsky et al. |
| 2007/0227360 A1 | 10/2007 | Atlas et al. |
| 2007/0227537 A1 | 10/2007 | Bemister et al. |
| 2007/0233022 A1 | 10/2007 | Henley et al. |
| 2007/0250009 A1 | 10/2007 | Barak |
| 2007/0255114 A1 | 11/2007 | Ackerman et al. |
| 2007/0255116 A1 | 11/2007 | Mehta et al. |
| 2007/0260226 A1 | 11/2007 | Jaeb et al. |
| 2007/0271298 A1 | 11/2007 | Juang et al. |
| 2007/0276309 A1 | 11/2007 | Xu et al. |
| 2007/0282249 A1 | 12/2007 | Quisenberry et al. |
| 2008/0004818 A1 | 1/2008 | Zaleski |
| 2008/0005000 A1 | 1/2008 | Radl et al. |
| 2008/0009681 A1 | 1/2008 | Hussiny |
| 2008/0015526 A1 | 1/2008 | Reiner et al. |
| 2008/0039761 A1 | 2/2008 | Heaton et al. |
| 2008/0041401 A1 | 2/2008 | Casola et al. |
| 2008/0051708 A1 | 2/2008 | Kumar et al. |
| 2008/0071209 A1 | 3/2008 | Moubayed et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2008/0077091 A1 | 3/2008 | Mulligan |
| 2008/0082040 A1 | 4/2008 | Kubler et al. |
| 2008/0082077 A1 | 4/2008 | Williams |
| 2008/0086357 A1 | 4/2008 | Choubey et al. |
| 2008/0091175 A1 | 4/2008 | Frikart et al. |
| 2008/0091659 A1 | 4/2008 | McFaul |
| 2008/0119705 A1 | 5/2008 | Patel et al. |
| 2008/0125697 A1 | 5/2008 | Gao |
| 2008/0125698 A1 | 5/2008 | Gerg et al. |
| 2008/0126126 A1 | 5/2008 | Ballai |
| 2008/0140160 A1 | 6/2008 | Goetz et al. |
| 2008/0147431 A1 | 6/2008 | Walneck et al. |
| 2008/0167534 A1 | 7/2008 | Young et al. |
| 2008/0177224 A1 | 7/2008 | Kelly et al. |
| 2008/0177579 A1 | 7/2008 | Dehaan |
| 2008/0180268 A1 | 7/2008 | Nissels et al. |
| 2008/0200868 A1 | 8/2008 | Alberti et al. |
| 2008/0200905 A1 | 8/2008 | Heaton |
| 2008/0200906 A1 | 8/2008 | Sanders et al. |
| 2008/0201174 A1 | 8/2008 | Ramasubramanian et al. |
| 2008/0208147 A1 | 8/2008 | Argenta et al. |
| 2008/0209357 A1 | 8/2008 | Vasta et al. |
| 2008/0221396 A1 | 9/2008 | Garces et al. |
| 2008/0228526 A1 | 9/2008 | Locke et al. |
| 2008/0234641 A1 | 9/2008 | Locke et al. |
| 2008/0242945 A1 | 10/2008 | Gugliotti et al. |
| 2008/0243035 A1 | 10/2008 | Crunkilton |
| 2008/0243096 A1 | 10/2008 | Svedman |
| 2008/0249377 A1 | 10/2008 | Molducci et al. |
| 2008/0272254 A1 | 11/2008 | Harr et al. |
| 2008/0300572 A1 | 12/2008 | Rankers et al. |
| 2008/0307353 A1 | 12/2008 | Molducci et al. |
| 2008/0312953 A1 | 12/2008 | Claus |
| 2008/0319510 A1 | 12/2008 | Simpson et al. |
| 2009/0005746 A1 | 1/2009 | Nielsen et al. |
| 2009/0023432 A1 | 1/2009 | MacInnis et al. |
| 2009/0037216 A1 | 2/2009 | Bluemler et al. |
| 2009/0037220 A1 | 2/2009 | Chambers et al. |
| 2009/0043268 A1 | 2/2009 | Eddy et al. |
| 2009/0048492 A1 | 2/2009 | Rantala et al. |
| 2009/0048865 A1 | 2/2009 | Breazeale, Jr. |
| 2009/0082741 A1 | 3/2009 | Hu |
| 2009/0097623 A1 | 4/2009 | Bharadwaj |
| 2009/0099866 A1 | 4/2009 | Newman |
| 2009/0099867 A1 | 4/2009 | Newman |
| 2009/0101219 A1 | 4/2009 | Martini et al. |
| 2009/0115663 A1 | 5/2009 | Brown et al. |
| 2009/0118591 A1 | 5/2009 | Kim et al. |
| 2009/0118751 A1 | 5/2009 | Wiener et al. |
| 2009/0125055 A1 | 5/2009 | Larkin et al. |
| 2009/0125331 A1 | 5/2009 | Pamsgaard et al. |
| 2009/0125389 A1 | 5/2009 | Dunko et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0171288 A1 | 7/2009 | Wheeler |
| 2009/0171289 A1 | 7/2009 | Davis et al. |
| 2009/0177495 A1 | 7/2009 | Abousy et al. |
| 2009/0182266 A1 | 7/2009 | Gordon et al. |
| 2009/0182594 A1 | 7/2009 | Choubey |
| 2009/0187424 A1 | 7/2009 | Grabowski |
| 2009/0204434 A1 | 8/2009 | Breazeale |
| 2009/0204435 A1 | 8/2009 | Gale |
| 2009/0205042 A1 | 8/2009 | Zhou et al. |
| 2009/0206017 A1 | 8/2009 | Rohde et al. |
| 2009/0224889 A1 | 9/2009 | Aggarwal et al. |
| 2009/0227910 A1 | 9/2009 | Pedersen et al. |
| 2009/0248448 A1 | 10/2009 | Zakay et al. |
| 2009/0248578 A1 | 10/2009 | Pollock et al. |
| 2009/0254362 A1 | 10/2009 | Choubey et al. |
| 2009/0259220 A1 | 10/2009 | Appling et al. |
| 2009/0270833 A1 | 10/2009 | DeBelser et al. |
| 2009/0276008 A1 | 11/2009 | Lee et al. |
| 2009/0281464 A1 | 11/2009 | Cioanta et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0282192 A1 | 11/2009 | Maus et al. |
| 2009/0292264 A1 | 11/2009 | Hudspeth et al. |
| 2009/0299306 A1 | 12/2009 | Buan |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0010646 A1 | 1/2010 | Drew et al. |
| 2010/0017471 A1 | 1/2010 | Brown et al. |
| 2010/0020021 A1 | 1/2010 | Mills et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0056875 A1 | 3/2010 | Schoenberg et al. |
| 2010/0069829 A1 | 3/2010 | Hutchinson et al. |
| 2010/0081971 A1 | 4/2010 | Allison |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0114026 A1 | 5/2010 | Karratt et al. |
| 2010/0121257 A1 | 5/2010 | King |
| 2010/0126268 A1 | 5/2010 | Baily et al. |
| 2010/0137775 A1 | 6/2010 | Hu et al. |
| 2010/0145161 A1 | 6/2010 | Niyato et al. |
| 2010/0145289 A1 | 6/2010 | Line et al. |
| 2010/0150991 A1 | 6/2010 | Bernstein |
| 2010/0152624 A1 | 6/2010 | Tanis et al. |
| 2010/0168687 A1 | 7/2010 | Yu |
| 2010/0169111 A1 | 7/2010 | Brue et al. |
| 2010/0169120 A1 | 7/2010 | Herbst et al. |
| 2010/0191178 A1 | 7/2010 | Ross et al. |
| 2010/0191199 A1 | 7/2010 | Evans et al. |
| 2010/0198142 A1 | 8/2010 | Sloan et al. |
| 2010/0200486 A1 | 8/2010 | Gunther et al. |
| 2010/0204663 A1 | 8/2010 | Wudyka |
| 2010/0211030 A1 | 8/2010 | Turner et al. |
| 2010/0222645 A1 | 9/2010 | Nadler et al. |
| 2010/0228205 A1 | 9/2010 | Hu et al. |
| 2010/0234708 A1 | 9/2010 | Buck et al. |
| 2010/0250697 A1 | 9/2010 | Hansen et al. |
| 2010/0251114 A1 | 9/2010 | Wehba et al. |
| 2010/0255876 A1 | 10/2010 | Jordan et al. |
| 2010/0268179 A1 | 10/2010 | Kelch et al. |
| 2010/0274177 A1 | 10/2010 | Rybski et al. |
| 2010/0280435 A1 | 11/2010 | Raney et al. |
| 2010/0280536 A1 | 11/2010 | Hartwell |
| 2010/0282834 A1 | 11/2010 | Devergne et al. |

(56) References Cited

U.S. PATENT DOCUMENTS

| | | |
|---|---|---|
| 2010/0305490 A1 | 12/2010 | Coulthard et al. |
| 2010/0305523 A1 | 12/2010 | Vess |
| 2010/0313958 A1 | 12/2010 | Patel et al. |
| 2010/0314517 A1 | 12/2010 | Patzer |
| 2010/0317933 A1 | 12/2010 | Colman et al. |
| 2010/0318043 A1 | 12/2010 | Malhi et al. |
| 2010/0318071 A1 | 12/2010 | Wudyka |
| 2010/0331673 A1 | 12/2010 | Maschke et al. |
| 2010/0331741 A9 | 12/2010 | Cioanta et al. |
| 2011/0003610 A1 | 1/2011 | Key et al. |
| 2011/0004188 A1 | 1/2011 | Shekalim |
| 2011/0006876 A1 | 1/2011 | Moberg et al. |
| 2011/0009824 A1 | 1/2011 | Yodfat et al. |
| 2011/0015585 A1 | 1/2011 | Svedman et al. |
| 2011/0015587 A1 | 1/2011 | Tumey et al. |
| 2011/0015590 A1 | 1/2011 | Svedman et al. |
| 2011/0021952 A1 | 1/2011 | Vallone |
| 2011/0028881 A1 | 2/2011 | Basaglia |
| 2011/0028882 A1 | 2/2011 | Basaglia |
| 2011/0028921 A1 | 2/2011 | Hartwell et al. |
| 2011/0034861 A1 | 2/2011 | Schaefer |
| 2011/0038741 A1 | 2/2011 | Lissner et al. |
| 2011/0040288 A1 | 2/2011 | Eckstein et al. |
| 2011/0046521 A1 | 2/2011 | Farrelly |
| 2011/0054810 A1 | 3/2011 | Turner |
| 2011/0063117 A1 | 3/2011 | Turner |
| 2011/0066096 A1 | 3/2011 | Svedman |
| 2011/0066110 A1 | 3/2011 | Fathallah et al. |
| 2011/0066123 A1 | 3/2011 | Tout et al. |
| 2011/0071415 A1 | 3/2011 | Karwoski et al. |
| 2011/0071844 A1 | 3/2011 | Cannon et al. |
| 2011/0073107 A1 | 3/2011 | Rodman et al. |
| 2011/0073644 A1 | 3/2011 | Sarkis, Jr. et al. |
| 2011/0077605 A1 | 3/2011 | Karpowicz et al. |
| 2011/0092927 A1 | 4/2011 | Wilkes et al. |
| 2011/0092958 A1 | 4/2011 | Jacobs |
| 2011/0106028 A1 | 5/2011 | Giezendanner et al. |
| 2011/0106561 A1 | 5/2011 | Eaton, Jr. et al. |
| 2011/0107251 A1 | 5/2011 | Guaitoli et al. |
| 2011/0112492 A1 | 5/2011 | Bharti et al. |
| 2011/0112857 A1 | 5/2011 | Yurko et al. |
| 2011/0130712 A1 | 6/2011 | Topaz |
| 2011/0133948 A1 | 6/2011 | Ervin |
| 2011/0137759 A1 | 6/2011 | Wellington et al. |
| 2011/0145018 A1 | 6/2011 | Fotsch et al. |
| 2011/0152739 A1 | 6/2011 | Roncadi et al. |
| 2011/0173028 A1 | 7/2011 | Bond |
| 2011/0184754 A1 | 7/2011 | Park et al. |
| 2011/0190703 A1 | 8/2011 | Pratt et al. |
| 2011/0196321 A1 | 8/2011 | Wudyka |
| 2011/0225008 A1 | 9/2011 | Elkouh et al. |
| 2011/0237981 A1 | 9/2011 | Voss |
| 2011/0245682 A1 | 10/2011 | Robinson et al. |
| 2011/0246219 A1 | 10/2011 | Smith et al. |
| 2011/0251569 A1 | 10/2011 | Turner et al. |
| 2011/0257572 A1 | 10/2011 | Locke et al. |
| 2011/0275353 A1 | 11/2011 | Liu |
| 2011/0285244 A1 | 11/2011 | Lewis et al. |
| 2011/0288511 A1 | 11/2011 | Locke et al. |
| 2011/0288878 A1 | 11/2011 | Blair |
| 2011/0290979 A1 | 12/2011 | Henault et al. |
| 2011/0313789 A1 | 12/2011 | Kamen et al. |
| 2011/0319813 A1 | 12/2011 | Kamen et al. |
| 2012/0001762 A1 | 1/2012 | Turner et al. |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0035561 A1 | 2/2012 | Locke et al. |
| 2012/0046624 A1 | 2/2012 | Locke et al. |
| 2012/0046625 A1 | 2/2012 | Johannison |
| 2012/0071845 A1 | 3/2012 | Hu et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123358 A1 | 5/2012 | Hall et al. |
| 2012/0123796 A1 | 5/2012 | McFaul |
| 2012/0157889 A1 | 6/2012 | Tanis et al. |
| 2012/0157941 A1 | 6/2012 | Luckemeyer et al. |
| 2012/0176394 A1 | 7/2012 | Vik et al. |
| 2012/0181405 A1 | 7/2012 | Zlatic et al. |
| 2012/0182143 A1 | 7/2012 | Gaines et al. |
| 2012/0184930 A1 | 7/2012 | Johannison |
| 2012/0184932 A1 | 7/2012 | Giezendanner et al. |
| 2012/0191475 A1 | 7/2012 | Pandey |
| 2012/0197196 A1 | 8/2012 | Halbert et al. |
| 2012/0197580 A1 | 8/2012 | Vij et al. |
| 2012/0209228 A1 | 8/2012 | Croizat et al. |
| 2012/0212434 A1 | 8/2012 | Bluemler et al. |
| 2012/0212455 A1 | 8/2012 | Kloeffel |
| 2012/0215455 A1 | 8/2012 | Patil et al. |
| 2012/0220960 A1 | 8/2012 | Ruland |
| 2012/0226247 A1 | 9/2012 | Danei et al. |
| 2012/0226768 A1 | 9/2012 | Gaines et al. |
| 2012/0259283 A1 | 10/2012 | Haase |
| 2012/0259651 A1 | 10/2012 | Mallon et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0302976 A1 | 11/2012 | Locke et al. |
| 2012/0310205 A1 | 12/2012 | Lee et al. |
| 2013/0018355 A1 | 1/2013 | Brand et al. |
| 2013/0019744 A1 | 1/2013 | Hu |
| 2013/0023719 A1 | 1/2013 | Bennett |
| 2013/0028788 A1 | 1/2013 | Gronau et al. |
| 2013/0030394 A1 | 1/2013 | Locke et al. |
| 2013/0035615 A1 | 2/2013 | Hsieh |
| 2013/0045764 A1 | 2/2013 | Vik et al. |
| 2013/0053692 A1 | 2/2013 | Barron et al. |
| 2013/0062265 A1 | 3/2013 | Balschat et al. |
| 2013/0066285 A1 | 3/2013 | Locke et al. |
| 2013/0066301 A1 | 3/2013 | Locke et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0088452 A1 | 4/2013 | Glaser-Seidnitzer et al. |
| 2013/0090613 A1 | 4/2013 | Kelch et al. |
| 2013/0090949 A1 | 4/2013 | Tibebu |
| 2013/0102836 A1 | 4/2013 | Millman |
| 2013/0103419 A1 | 4/2013 | Beaudry |
| 2013/0123755 A1 | 5/2013 | Locke et al. |
| 2013/0124227 A1 | 5/2013 | Ellis |
| 2013/0133036 A1 | 5/2013 | Wang et al. |
| 2013/0144227 A1 | 6/2013 | Locke et al. |
| 2013/0144230 A1 | 6/2013 | Wu et al. |
| 2013/0150686 A1 | 6/2013 | Fronterhouse et al. |
| 2013/0159456 A1 | 6/2013 | Daoud et al. |
| 2013/0160082 A1 | 6/2013 | Miller |
| 2013/0165821 A1 | 6/2013 | Freedman et al. |
| 2013/0165854 A1 | 6/2013 | Sandhu et al. |
| 2013/0165877 A1 | 6/2013 | Leeson et al. |
| 2013/0169432 A1 | 7/2013 | Ozgul et al. |
| 2013/0176230 A1 | 7/2013 | Georgiev et al. |
| 2013/0186405 A1 | 7/2013 | Krzyzanowski et al. |
| 2013/0190717 A1 | 7/2013 | Dollar et al. |
| 2013/0190903 A1 | 7/2013 | Balakrishnan et al. |
| 2013/0196703 A1 | 8/2013 | Masoud et al. |
| 2013/0198685 A1 | 8/2013 | Bernini et al. |
| 2013/0204106 A1 | 8/2013 | Bennett |
| 2013/0204210 A1 | 8/2013 | Pratt et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0223979 A1 | 8/2013 | Locke et al. |
| 2013/0226607 A1 | 8/2013 | Woody et al. |
| 2013/0227128 A1 | 8/2013 | Wagstaff |
| 2013/0231596 A1 | 9/2013 | Hornback et al. |

(56) References Cited

U.S. PATENT DOCUMENTS

| | | |
|---|---|---|
| 2013/0245387 A1 | 9/2013 | Patel |
| 2013/0245580 A1 | 9/2013 | Locke et al. |
| 2013/0253952 A1 | 9/2013 | Burke et al. |
| 2013/0254717 A1 | 9/2013 | Al-Ali et al. |
| 2013/0262730 A1 | 10/2013 | Al-Ali et al. |
| 2013/0267917 A1 | 10/2013 | Pan et al. |
| 2013/0267918 A1 | 10/2013 | Pan et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0275145 A1 | 10/2013 | Moore et al. |
| 2013/0285837 A1 | 10/2013 | Uchida |
| 2013/0289536 A1 | 10/2013 | Croizat et al. |
| 2013/0293570 A1 | 11/2013 | Dolgos et al. |
| 2013/0297350 A1 | 11/2013 | Gross et al. |
| 2013/0303975 A1 | 11/2013 | Gvodas et al. |
| 2013/0310631 A1 | 11/2013 | Lee et al. |
| 2013/0310726 A1 | 11/2013 | Miller et al. |
| 2013/0310778 A1 | 11/2013 | Locke et al. |
| 2013/0317420 A1 | 11/2013 | Wehmeyer |
| 2013/0317463 A1 | 11/2013 | Yao et al. |
| 2013/0325508 A1 | 12/2013 | Johnson et al. |
| 2013/0327326 A1 | 12/2013 | Brennan |
| 2013/0331822 A1 | 12/2013 | Patel et al. |
| 2013/0332197 A1 | 12/2013 | Hinkel |
| 2013/0335233 A1 | 12/2013 | Kamar et al. |
| 2013/0345524 A1 | 12/2013 | Meyer et al. |
| 2014/0031884 A1 | 1/2014 | Elghazzawi |
| 2014/0032231 A1 | 1/2014 | Semen et al. |
| 2014/0052202 A1 | 2/2014 | Daynes |
| 2014/0055588 A1 | 2/2014 | Bangera et al. |
| 2014/0058344 A1 | 2/2014 | Toth |
| 2014/0100516 A1 | 4/2014 | Hunt et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0114236 A1 | 4/2014 | Gordon |
| 2014/0114237 A1 | 4/2014 | Gordon |
| 2014/0129250 A1 | 5/2014 | Daniel et al. |
| 2014/0136218 A1 | 5/2014 | Bolene et al. |
| 2014/0148138 A1 | 5/2014 | Chou et al. |
| 2014/0163490 A1 | 6/2014 | Locke et al. |
| 2014/0163493 A1 | 6/2014 | Weston et al. |
| 2014/0194835 A1 | 7/2014 | Ehlert |
| 2014/0236106 A1 | 8/2014 | Locke et al. |
| 2014/0303551 A1 | 10/2014 | Germain et al. |
| 2014/0323906 A1 | 10/2014 | Peatfield et al. |
| 2015/0012290 A1 | 1/2015 | Inciardi et al. |
| 2015/0025482 A1 | 1/2015 | Begin et al. |
| 2015/0025486 A1 | 1/2015 | Hu et al. |
| 2015/0051560 A1 | 2/2015 | Askem |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0133829 A1 | 5/2015 | DeBusk et al. |
| 2015/0174304 A1 | 6/2015 | Askem et al. |
| 2016/0080365 A1 | 3/2016 | Baker et al. |
| 2016/0110507 A1 | 4/2016 | Abbo |
| 2016/0151015 A1 | 6/2016 | Condurso et al. |
| 2016/0203275 A1 | 7/2016 | Benjamin et al. |
| 2017/0065837 A1 | 3/2017 | Tanis et al. |
| 2018/0158545 A1 | 6/2018 | Blomquist |
| 2018/0233016 A1 | 8/2018 | Daniel et al. |
| 2018/0233221 A1 | 8/2018 | Blomquist |

FOREIGN PATENT DOCUMENTS

| | | |
|---|---|---|
| CN | 104721892 A | 6/2015 |
| DE | 10 2010 036 405 | 1/2012 |
| DE | 20 2014 10752 U1 | 6/2014 |
| EP | 0 403 294 | 12/1990 |
| EP | 0 526 166 | 2/1994 |
| EP | 0 829 228 | 3/1998 |
| EP | 1 034 734 | 9/2000 |
| EP | 1 064 053 | 1/2001 |
| EP | 0566381 B1 | 7/2002 |
| EP | 1231965 A2 | 8/2002 |
| EP | 0 809 470 | 10/2002 |
| EP | 1291802 A2 | 3/2003 |
| EP | 1309960 A1 | 5/2003 |
| EP | 1 176 909 | 7/2003 |
| EP | 0 904 788 | 11/2003 |
| EP | 0814864 B1 | 12/2003 |
| EP | 1407624 A2 | 4/2004 |
| EP | 1011420 B1 | 12/2004 |
| EP | 1 199 046 | 1/2005 |
| EP | 1495713 A1 | 1/2005 |
| EP | 1524619 A2 | 4/2005 |
| EP | 1540557 A2 | 6/2005 |
| EP | 1 566 201 A2 | 8/2005 |
| EP | 1 566 201 A3 | 9/2005 |
| EP | 1579367 A2 | 9/2005 |
| EP | 1587017 A2 | 10/2005 |
| EP | 1 633 241 | 3/2006 |
| EP | 1 684 146 | 7/2006 |
| EP | 1 702 649 | 9/2006 |
| EP | 1 788 503 | 5/2007 |
| EP | 1 797 918 | 6/2007 |
| EP | 1839244 A1 | 10/2007 |
| EP | 1839615 A1 | 10/2007 |
| EP | 1 857 950 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 1 610 861 | 3/2009 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2 172 859 | 4/2010 |
| EP | 2 218 478 | 8/2010 |
| EP | 2214552 A1 | 8/2010 |
| EP | 2 246 079 | 11/2010 |
| EP | 2 248 545 | 11/2010 |
| EP | 1 668 556 | 2/2011 |
| EP | 2 279 028 | 2/2011 |
| EP | 1404213 B1 | 3/2011 |
| EP | 1247229 B1 | 4/2011 |
| EP | 1 970 098 | 5/2011 |
| EP | 1406540 B1 | 6/2011 |
| EP | 1812094 B1 | 8/2011 |
| EP | 2384472 A1 | 11/2011 |
| EP | 2226002 B1 | 1/2012 |
| EP | 1610494 B1 | 3/2012 |
| EP | 1 248 660 | 4/2012 |
| EP | 2023800 B1 | 4/2012 |
| EP | 2451513 A1 | 5/2012 |
| EP | 1 248 661 | 8/2012 |
| EP | 2488977 A1 | 8/2012 |
| EP | 2 503 478 | 9/2012 |
| EP | 2 505 169 | 12/2012 |
| EP | 2 529 765 | 12/2012 |
| EP | 2 389 961 | 3/2013 |
| EP | 2619723 A2 | 7/2013 |
| EP | 1881784 B1 | 10/2013 |
| EP | 2664194 A2 | 11/2013 |
| EP | 2 674 845 | 12/2013 |
| EP | 2 650 027 | 1/2014 |
| EP | 1 565 219 | 2/2014 |
| EP | 2745204 A1 | 6/2014 |
| EP | 2 562 665 | 7/2014 |
| EP | 2 066 365 | 4/2015 |
| EP | 2563437 B1 | 3/2017 |
| EP | 2556650 B1 | 5/2017 |
| EP | 2632407 B1 | 8/2017 |
| EP | 2320971 B1 | 5/2018 |
| EP | 2335173 B1 | 5/2018 |
| EP | 2440112 B1 | 10/2018 |
| EP | 3219340 B1 | 1/2019 |
| GB | 2235877 | 3/1991 |
| GB | 2279784 | 1/1995 |
| GB | 2342584 | 4/2000 |

(56) References Cited

FOREIGN PATENT DOCUMENTS

| | | |
|---|---|---|
| GB | 2409951 | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 | 5/2011 |
| GB | 2488904 | 9/2012 |
| GB | 2446923 B | 5/2013 |
| GB | 2491946 B | 8/2014 |
| JP | H10-085288 | 4/1998 |
| JP | 2003-116796 | 4/2003 |
| JP | 2005-027798 | 2/2005 |
| JP | 2005-71314 | 3/2005 |
| JP | 2007-289481 | 11/2007 |
| WO | WO 1996/19335 | 6/1996 |
| WO | WO 1996/025112 | 8/1996 |
| WO | WO 96/27163 A1 | 9/1996 |
| WO | WO 97/44745 A1 | 11/1997 |
| WO | WO 99/24927 A1 | 5/1999 |
| WO | WO 1999/035588 | 7/1999 |
| WO | WO 1999/047209 | 9/1999 |
| WO | WO 99/63886 A1 | 12/1999 |
| WO | WO 2000/032088 | 6/2000 |
| WO | WO 00/60522 A2 | 10/2000 |
| WO | WO 2000/061003 | 10/2000 |
| WO | WO 2001/14048 | 3/2001 |
| WO | WO 01/33457 A1 | 5/2001 |
| WO | WO 2001/036027 | 5/2001 |
| WO | WO 01/81829 A1 | 11/2001 |
| WO | WO 02/17075 A2 | 2/2002 |
| WO | WO 02/33577 A1 | 4/2002 |
| WO | WO 2002/028477 | 4/2002 |
| WO | WO 02/078594 A2 | 10/2002 |
| WO | WO 02/101713 A1 | 12/2002 |
| WO | WO 2002/093301 | 5/2003 |
| WO | WO 03/054668 A2 | 7/2003 |
| WO | WO 2003/055432 | 7/2003 |
| WO | WO 2003/060650 | 7/2003 |
| WO | WO 2003/101508 | 12/2003 |
| WO | WO 2004/057514 A2 | 7/2004 |
| WO | WO 2003/094090 | 9/2004 |
| WO | WO 2004/074457 A2 | 9/2004 |
| WO | WO 2004/093983 | 11/2004 |
| WO | WO 2004/100779 | 11/2004 |
| WO | WO 2005/022349 A2 | 3/2005 |
| WO | WO 2005/031632 A2 | 4/2005 |
| WO | WO 2005/036447 A2 | 4/2005 |
| WO | WO 2005/045461 A1 | 5/2005 |
| WO | WO 2005/053793 A1 | 6/2005 |
| WO | WO 2005/057466 A2 | 6/2005 |
| WO | WO 2005/083619 A2 | 9/2005 |
| WO | WO 2005/101282 A2 | 10/2005 |
| WO | WO 2005/120097 A2 | 12/2005 |
| WO | WO 2005/109297 | 3/2006 |
| WO | WO 2006/021154 A1 | 3/2006 |
| WO | WO 2006/066583 A1 | 6/2006 |
| WO | WO 2006/066585 A2 | 6/2006 |
| WO | WO 2006/071711 A2 | 7/2006 |
| WO | WO 2006/099120 A2 | 9/2006 |
| WO | WO 2006/108858 A1 | 10/2006 |
| WO | WO 2006/111109 A1 | 10/2006 |
| WO | WO 2007/027490 A2 | 3/2007 |
| WO | WO 2007/035646 A2 | 3/2007 |
| WO | WO 2007/056734 | 5/2007 |
| WO | WO 2007/127879 A2 | 11/2007 |
| WO | WO 2007/133478 A2 | 11/2007 |
| WO | WO 2007/137869 A2 | 12/2007 |
| WO | WO 2008/010012 A2 | 1/2008 |
| WO | WO 2008/036344 | 3/2008 |
| WO | WO 2008/036360 | 3/2008 |
| WO | WO 2008/039314 | 4/2008 |
| WO | WO 2008/062382 A2 | 5/2008 |
| WO | WO 2008/104609 | 9/2008 |
| WO | WO 2008/116295 | 10/2008 |
| WO | WO 2008/132215 | 11/2008 |
| WO | WO 2008/157017 | 12/2008 |
| WO | WO 2009/021523 | 2/2009 |
| WO | WO 2009/023432 | 4/2009 |
| WO | WO 2009/047524 | 4/2009 |
| WO | WO 2009/089390 | 7/2009 |
| WO | WO 2009/093116 | 7/2009 |
| WO | WO 2009/117549 | 9/2009 |
| WO | WO 2009/137699 A2 | 11/2009 |
| WO | WO 2009/140669 A2 | 11/2009 |
| WO | WO 2009/151645 | 12/2009 |
| WO | WO 2010/017484 | 2/2010 |
| WO | WO 2010/025166 A1 | 3/2010 |
| WO | WO 2010/025467 A1 | 3/2010 |
| WO | WO 2010/039481 | 4/2010 |
| WO | WO 2010/078558 A1 | 7/2010 |
| WO | WO 2010/085033 | 7/2010 |
| WO | WO 2010/089368 | 8/2010 |
| WO | WO 2010/126668 | 11/2010 |
| WO | WO 2010/132617 A2 | 11/2010 |
| WO | WO 2010/145780 | 12/2010 |
| WO | WO 2011/023275 | 3/2011 |
| WO | WO 2011/023384 A1 | 3/2011 |
| WO | WO 2011/039676 A2 | 4/2011 |
| WO | WO 2011/046860 A2 | 4/2011 |
| WO | WO 2011/047334 A1 | 4/2011 |
| WO | WO 2011/089270 | 7/2011 |
| WO | WO 2011/107972 | 9/2011 |
| WO | WO 2011/123933 A1 | 10/2011 |
| WO | WO 2011/124388 | 10/2011 |
| WO | WO 2009/137699 | 11/2011 |
| WO | WO 2011/137230 | 11/2011 |
| WO | WO 2012/009869 | 1/2012 |
| WO | WO 2012/027342 | 3/2012 |
| WO | WO 2012/027912 | 3/2012 |
| WO | WO 2012/027913 | 3/2012 |
| WO | WO 2012/027914 | 3/2012 |
| WO | WO 2012/027915 | 3/2012 |
| WO | WO 2012/027916 | 3/2012 |
| WO | WO 2012/051278 | 4/2012 |
| WO | WO 2012/054863 | 4/2012 |
| WO | WO 2012/100624 | 8/2012 |
| WO | WO 2012/107430 | 8/2012 |
| WO | WO 2012/127281 | 9/2012 |
| WO | WO 2012/156655 | 11/2012 |
| WO | WO 2012/160164 | 11/2012 |
| WO | WO 2012/172818 | 12/2012 |
| WO | WO 2013/014278 | 1/2013 |
| WO | WO 2013/025815 | 2/2013 |
| WO | WO 2013/026999 A1 | 2/2013 |
| WO | WO 2013/029330 | 3/2013 |
| WO | WO 2013/036853 A2 | 3/2013 |
| WO | WO 2013/054217 | 4/2013 |
| WO | WO 2013/063848 | 5/2013 |
| WO | WO 2013/066775 | 5/2013 |
| WO | WO 2013/078214 | 5/2013 |
| WO | WO 2013/089712 | 6/2013 |
| WO | WO 2013/102855 | 7/2013 |
| WO | WO 2013/109517 | 7/2013 |
| WO | WO 2013/119978 | 8/2013 |
| WO | WO 2013/123022 | 8/2013 |
| WO | WO 2013/126049 | 8/2013 |
| WO | WO 2013/141870 | 9/2013 |
| WO | WO 2013/150025 | 10/2013 |
| WO | WO 2013/175076 | 11/2013 |
| WO | WO 2013/182218 | 12/2013 |
| WO | WO 2014/012802 | 1/2014 |
| WO | WO 2014/151930 | 9/2014 |
| WO | WO 2014/009876 | 12/2014 |
| WO | WO 2015/023515 | 2/2015 |
| WO | WO 2015/091070 | 6/2015 |
| WO | WO 2015/197462 | 12/2015 |

OTHER PUBLICATIONS

Australian Office Action, re AU Application No. 2017201192, dated Nov. 14, 2017.
Canadian Office Action, re CA Application No. 2,814,657, dated Dec. 11, 2017.

(56) References Cited

OTHER PUBLICATIONS

Canadian Office Action, re CA Application No. 2,815,474, dated Jul. 19, 2017.
International Preliminary Report on Patentability and Written Opinion, re PCT/US2014/026692, dated Sep. 24, 2015.
International Search Report and Written Opinion, re PCT Application No. PCT/US2014/026692, dated Mar. 2, 2015.
Invitation to Pay Additional Fees and Search Report, re PCT Application No. PCT/US2014/026692, dated Sep. 26, 2014.
Japanese Office Action, re JP Application No. 2015-254568, dated Jul. 3, 2017.
U.S. Appl. No. 15/362,458, filed Nov. 28, 2016, Tanis et al.
Australian First Exam Report, re AU Application No. 2011316883, dated Feb. 29, 2016.
Australian Second Exam Report, re AU Application No. 2011316883, dated Feb. 2, 2017.
International Search Report and Written Opinion, re International Application No. PCT/US2011/057337, dated Feb. 23, 2012.
International Search Report and Written Opinion, re International Application No. PCT/US2011/057332, dated Mar. 23, 2012.
International Preliminary Report on Patentability, re PCT Application No. PCT/US2011/057337, dated May 2, 2013.
Japanese Office Action, re JP Application No. 2015-254568, dated Feb. 21, 2017.
Oddsson et al., "A Robotic Home Telehealth Platform System for Treatment Adherence, Social Assistance and Companionship—an Overview", 31st Annual International Conference of the IEEE Sep. 2009, pp. 6437-6440.
Cinterion PHS8-P 3G HSPA+, 2012. URL: http://www.cinterion.com/tl_files/cinterion/downloads/cinterion_datasheet_PHS8_web.pdf.
Huntleigh Healthcare, "Negative Pressure Positive Outcomes" WoundASSIST TNP Console and Canister Brochure, 2007, in 6 pages.
International Search Report and Written Opinion, re International Application No. PCT/US2011/055937, dated Dec. 23, 2011.
International Preliminary Report on Patentability, re International Application No. PCT/US2011/055937, dated Apr. 25, 2013.
Japanese Office Action (Notice of Rejection), re JP Application No. 2013-533968, dated Jul. 14, 2015.
"Vivano—Product application description," Hartmann Vivano, http://www.vivanosystem.info/20809.php, accessed Feb. 28, 2013.
U.S. Appl. No. 13/271,870, filed Oct. 12, 2011, U.S. Pat. No. 9,526,920.
U.S. Appl. No. 13/278,565, filed Oct. 21, 2011, Publication No. 2012/0157889.
U.S. Appl. No. 15/357,883, filed Nov. 21, 2016, Publication No. 2017/0065837.

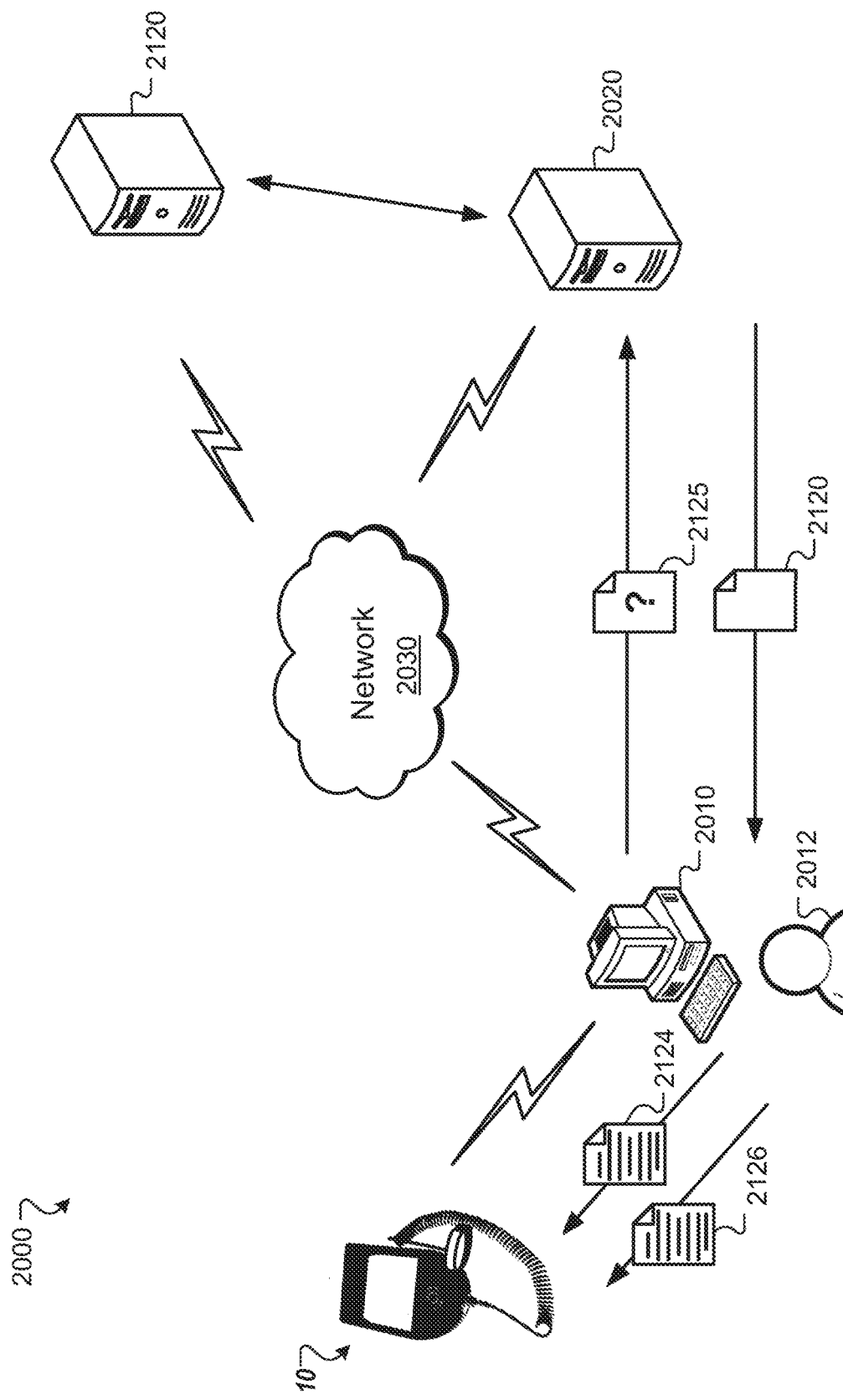

MEDICAL DEVICE

CROSS-REFERENCE TO RELATED APPLICATIONS

This application is a continuation of U.S. application Ser. No. 15/357,883, filed on Nov. 21, 2016, which is a continuation of U.S. application Ser. No. 13/271,870, filed on Oct. 12, 2011, now U.S. Pat. No. 9,526,920, issued on Dec. 27, 2016, which claims the benefit of U.S. Provisional Application No. 61/392,154, filed Oct. 12, 2010, U.S. Provisional Application No. 61/405,405, filed Oct. 21, 2010, U.S. Provisional Application No. 61/405,757, filed Oct. 22, 2010, and U.S. Provisional Application No. 61/483,445, filed May 6, 2011, each of which is incorporated herein in its entirety for all purposes.

FIELD

This description relates to a medical device.

BACKGROUND

Medical devices can provide treatment for a variety of health conditions. In some instances, a patient has a degree of control over treatment with a medical device. For example, a patient may be able to initiate treatment with a medical device. The capabilities of a medical device determine to a large degree the way that the patient and others internet with the medical device. In particular, it is important that a medical device be capable of providing effective treatment and a positive patient experience.

SUMMARY

In one aspect, a medical device includes: a treatment module configured to apply a treatment to a patient; one or more processing devices configured to: disallow treatment using the treatment module until treatment authorization occurs; determine that treatment authorization occurs; and in response to determining that treatment authorization occurs, permit treatment to be applied using the treatment module.

Implementations may include one or more of the following features. For example, treatment authorization occurs via payment. Treatment authorization occurs via patient identification. Treatment authorization is linked to geographic location. Treatment authorization occurs via authorization data stored on a removable medium.

Implementations may include one or more of the following features. For example, the medical device includes a wireless communication module operable to receive the activation code over a wireless communication link. The wireless communication link is a Bluetooth or cellular communication link. The medical device is configured to receive the activation code from an enabling device configured to activate a limited number of medical devices and to not activate more than the limited number of medical devices. The one or more processing devices being configured to receive the activation code includes the one or more processing devices being configured to access the activation code from a removable medium. The activation code includes authorization information indicating a number of treatments authorized using the medical device.

In another general aspect, an enabling device includes: a communication module operable to wirelessly transmit one or more activation codes to a medical device, the one or more activation codes being capable of activating the medical device; one or more data storage devices storing authorization information indicating a number of authorized activations of medical devices that the enabling device is authorized to perform; one or more processing devices configured to: receive user input indicating that a medical device should be activated; determine, based on the authorization information, whether activation of the medical device is authorized; if the determination indicates that the activation of the medical device is authorized: control the wireless communication module to transmit the one or more activation codes, and update the authorization information to decrease the number of authorized activations remaining for the enabling device; if the determination indicates that the treatment is not authorized, control the treatment module such that the one or more activation codes are not transmitted.

Implementations may include one or more of the following features. For example, the enabling device is associated with an inventory of medical devices, and the number of authorized activations of medical devices is based on the associated inventory. The communication module is further configured to receive, over a network, second authorization information altering the number of authorized activations the enabling device is authorized to perform, and the one or more processors are further configured to update the information indicating the number of authorized activations to alter the number of authorized activations by the additional number indicated by the second authorization information. The communication module is further configured to receive, over a network, second authorization information indicating an additional number of authorized activations the enabling device is authorized to perform, and the one or more processors are further configured to update the information indicating the number of authorized activations to increase the number of authorized activations by the additional number indicated by the second authorization information.

In another general aspect, a medical device includes: at least one treatment module configured to apply a treatment to a patient, the treatment module including at least one ultrasound transducer and at least one driver circuit coupled to the ultrasound transducer; one or more data storage devices; an interface configured to operatively connect to a removable storage device storing authorization data that identifies a level of treatment authorization; and at least one processing device configured to perform the following in response to receiving user input indicating a treatment should be initiated: determine whether the removable storage device is valid for use with the medical device; if the removable storage device is determined to be valid, access the authorization data; determine whether the treatment is authorized based on the accessed authorization data; if the treatment is determined to be authorized, control the treatment module to apply the treatment; and if the treatment is determined to not be authorized, control the treatment module such that the treatment is not applied.

Implementations of any of the aspects may include one or more of the following features. For example, to determine whether the removable storage device is valid for use with the medical device, the at least one processing device is configured to: access a serial number of the removable medium; and determine that the removable medium is valid if the serial number is within a predetermined range of values. The at least one processing device is configured to record compliance data for the treatment on the removable storage device if the treatment is applied. The compliance data indicates a time, date, and duration of the treatment. The treatment module includes at least one ultrasound transducer and at least one driver circuit coupled to the ultrasound transducer. To control the treatment module to apply the treatment, the processing device is configured to control the driver circuit such that the driver circuit causes the ultrasound transducer to produce ultrasound with therapeutic properties. To control the treatment module such that the treatment is not applied, the processing device is configured to control the driver circuit such that ultrasound with therapeutic properties is not produced. The driver circuitry includes a signal generator and an ultrasound transducer driver.

The authorization data indicates a number of authorized treatments, and the at least one processing device is configured to decrease the number of authorized treatments indicated by the authorization data after a treatment is applied. The authorization data indicates an authorized amount of treatment time, and the at least one processing device is configured to decrease the amount of authorized treatment time indicated by the authorization data after a treatment is applied. The medical device includes a communication module. The at least one processing device is configured to: receive authorization data that indicates a level of treatment authorization through the communication module; store the received authorization data on the removable storage device or a second storage device of the medical device; and in response to receiving the user input indicating a treatment should be initiated, determine whether the treatment is authorized based on the received authorization data. The communication module is a wireless communication module. The wireless communication module is a cellular communication module.

The authorization data is received from a server system configured to: determine that payment has been made for a number of treatments; determine that the payment is associated with the medical device; generate the authorization data; and transmit the authorization data to the medical device. The processing device is further configured to provide, if the treatment is determined to not be authorized, an indication to the patient that more treatments need to be purchased. The processing device is configured to receive new authorization data after providing the indication to the patient that more treatments need to be purchased, the new authorization data identifying a number of additional treatments for which payment has been received. The authorization data is encrypted, and the processing device is further configured to decrypt the authorization data. The medical device includes a second storage device. The second storage device stores a device identifier that uniquely identifies the medical device, the authorization data is encrypted, the at least one processing device is further configured to decrypt the authorization data; and the device identifier is used to decrypt the authorization data. The medical device includes a payment module configured to receive payment for a number of treatments. The payment module is configured to receive payment through a code, a credit card, or a SIM card. The at least one processing device is configured to: record on the removable storage device or an internal storage device information indicating occurrences of treatment applied by the medical device; and indicate, on a display of the medical device, days during which treatment was applied and days during which treatment was not applied. The medical device stores information about a treatment regimen for use of the medical device; and the at least one processing device is configured to indicate compliance with the treatment regimen by displaying a calendar that indicates the days during which treatment was applied and the days during which treatment was not applied.

Implementations may include one or more of the following features. For example, the enabling device is configured to activate the medical device by transmitting an activation code over a wireless communication link between the enabling device and the medical device, and the medical device is configured to allow treatments using the treatment module in response to receiving the activation code.

In another general aspect, a medical device includes: a treatment module configured to apply a treatment to a patient, the treatment module including at least one ultrasound transducer and at least one driver circuit coupled to the ultrasound transducer, a display, one or more data storage devices, and one or more processing devices. The one or more processing devices are configured to: receive user input that a treatment should be initiated using the treatment module; in response to receiving the user input, apply a treatment using the treatment module; record on the one or more data storage devices information indicating occurrences of treatment using the treatment module; and indicate on the display days during which treatment was applied and days during which treatment was not applied.

Implementations of any of the aspects may include one or more of the following features. For example, the days during which treatment was applied and days during which treatment was not applied are indicated on a calendar. Days of the calendar during which one or more treatments are applied are marked with a check mark and days of the calendar during which one or more treatments were not applied are unchecked. The one or more storage devices store information about a treatment regimen for use of the medical device, and the one or more processing devices are configured to indicate compliance with the treatment regimen on the calendar. The one or more processing devices being configured to indicate on the display days during which treatment was applied and days in which treatment was not applied includes the one or more processing devices being configured to automatically indicate on the display, in response to the medical device being powered on, days during which treatment was applied and days during which treatment was not applied.

In another general aspect, a medical device includes: a treatment module operable to apply a treatment to a patient, the treatment module including at least one ultrasound transducer and at least one driver circuit coupled to the ultrasound transducer; a primary or rechargeable battery configured to supply power to the medical device; a color display configured to display information to a user of the medical device; a wireless communication module; one or more data storage devices; one or more processing devices configured to: disallow treatment using the treatment module until an activation code is received; receive an activation code received by the wireless communication module over a wireless communication link; in response to receiving the activation code, permit treatment to be applied using the treatment module; store on the one or more data storage devices authorization information indicating a number of authorized treatments remaining for the medical device; receive user input indicating a treatment should be initiated; determine whether the treatment is authorized; if the determination indicates that the treatment is authorized, control the treatment module to apply the treatment and update the authorization information to decrease the number of authorized treatments remaining for the medical device; if the determination indicates that the treatment is not authorized, control the treatment module such that the treatment is not applied; record, on the one or more storage devices, compliance information indicating dates during which treatment was performed using the treatment module; cause the wireless communication module to transmit the recorded compliance information over the wireless communication link; and display on the color display a calendar indicating days during which treatment was performed and days during which treatment was not performed.

In another general aspect, a medical device includes: a treatment module operable to apply a treatment to a patient, the treatment module including at least one ultrasound transducer and at least one driver circuit coupled to the ultrasound transducer; a primary or rechargeable battery configured to supply power to the medical device; a color display configured to display information to a user of the medical device; one or more data storage devices including a removable memory card and a non-removable storage device; one or more processing devices configured to cause the medical device to: access from the removable memory card information indicating a number of authorized treatments for the medical device; based on the accessed information, store authorization information indicating the number of authorized treatments for the medical device on the non-removable storage; receive user input indicating a treatment should be initiated; determine, based on the authorization information, whether the treatment is authorized; if the determination indicates that the treatment is authorized, control the treatment module to apply the treatment and update the authorization information to decrease the number of authorized treatments remaining for the medical device; if the determination indicates that the treatment is not authorized, control the treatment module such that the treatment is not applied; record on the one or more storage devices compliance information indicating dates during which treatment was performed using the treatment module; automatically display on the color display, in response to the medical device being powered on, a calendar indicating days during which treatment was performed and days during which treatment was not performed; access, from a second removable memory card, second authorization information indicating a second number of authorized treatments using the medical device; and based on the second authorization information, increase the number of authorized treatments remaining for the medical device stored on the one or more storage devices.

The medical device includes means for determining the geographic location of the medical device, and treatment is not allowed to commence if the determined geographic location is outside an authorized geographic location. The medical device includes means for determining user identity, and treatment is not allowed to commence if the determined user identity does not match an authorized identity. The treatment module is configured to produce a pulsed ultrasound signal having a frequency in the range of 1 MHz to 2 MHz, consisting of pulses generated at a rate in the range of 100 Hz to 10 KHz with each pulse having a duration in the range of 10 microseconds to 2,000 microseconds. The pulsed ultrasound signal has a power intensity of 100 milliwatts per square centimeter or less. The medical device is a hand-held device configured to accelerate bone healing.

In another general aspect a computer-implemented method includes: receiving user input through a user interface of a medical device, the user input indicating a treatment should be administered by the medical device, and the medical device includes a treatment module configured to apply a treatment to a patient; determining whether a removable storage device coupled to the medical device is valid for use with the medical device; in response to determining that the removable storage device is valid for use with the medical device, accessing authorization data stored on the removable storage device; determining that the treatment is authorized based on the accessed authorization data; and controlling the treatment module to apply the treatment in response to determining that the treatment is authorized based on the accessed authorization data.

Implementations of any of the above aspects may include one or more of the following features. For example, the activation code includes the authorization information. The wireless communication link is a Bluetooth or cellular communication link. The one or more storage devices include a removable memory card; and the one or more processing devices configured to: record the compliance information to the removable memory card; and access an activation code stored on the removable memory card or another memory card.

The removable memory card and the second removable memory cards are Secure Digital memory cards. The one or more processing devices being configured to record on the one or more storage devices compliance information indicating dates during which treatment was performed using the treatment module includes the one or more processing devices being configured to record, on the removable memory card and on the non-removable storage, compliance information indicating dates during which treatment was performed using the treatment module. The one or more processing devices being configured to indicate on the display days during which treatment was performed and days in which treatment was not performed includes the one or more processing devices being configured to automatically indicate on the display, in response to the medical device being powered on, days during which treatment was performed and days in which treatment was not performed. The one or more processing devices are further configured to receive an authorization code indicating a number of treatments that are authorized for the medical device and update the authorization information such that the number of treatments indicated by authorization code are added. The one or more processing devices are configured to determine whether the treatment is authorized by determining if the authorization information indicates that at least one treatment is authorized for the medical device. The one or more processing devices are further configured to: access an identifier from the one or more storage devices; and cause the compliance information and the accessed identifier to be transmitted to a server system that is configured to receive the compliance information and the identifier.

Implementations of any of the aspects may include one or more of the following features. For example, determining whether the removable storage device coupled to the medical device is valid for use with the medical device includes accessing a serial number of the removable medium and determining that the removable medium is valid if the serial number is within a predetermined range of values. Recording compliance data for the treatment on the removable storage device if the treatment is applied. The treatment module includes at least one ultrasound transducer and at least one driver circuit. Controlling the treatment module to apply the treatment includes controlling the driver circuit such that the driver circuit causes an ultrasound transducer to produce ultrasound with therapeutic properties. Controlling the treatment module such that the treatment is not applied includes controlling the driver circuit such that ultrasound with therapeutic properties is not produced. Receiving the authorization data, and storing the received authorization data on the removable device.

Receiving the authorization data includes receiving the authorization data with a wireless communication module. The wireless communication module is a cellular communication module. The authorization data indicates a number of authorized treatments, and the computer-implemented method further includes decreasing the number of authorized treatments indicated by the authorization data after a treatment is applied. The authorization data indicates an authorized amount of treatment time, and the computer-implemented method further includes decreasing the amount of authorized treatment time indicated by the authorization data after a treatment is applied. Storing a device identifier that uniquely identifies a medical device. The authorization data is encrypted, accessing the authorization code includes decrypting the authorization data, and the device identifier is used to decrypt the authorization data. Recording on the removable storage device or an internal storage device information indicating occurrences of treatment applied by the medical device. Indicating, on a display of the medical device, days during which treatment was applied and days during which treatment was not applied. Indicating compliance with a treatment regimen by displaying a calendar that indicates the days during which treatment was applied and the days during which treatment was not applied. Receiving payment for a number of treatments. Receiving payment for a number of treatments includes receiving payment at the medical device for a number of treatments, the payment being entered with a code, a credit card, or a SIM card.

In another general aspect, a computer-implemented method includes: receiving user input that a treatment should be initiated using a treatment module of a medical device; in response to receiving the user input, controlling the treatment module to apply a treatment; recording on one or more data storage devices information indicating occurrences of treatment using the treatment module; and indicating, on a display of the medical device, days during which treatment was applied and days during which treatment was not applied.

Implementations of any of the aspects may include one or more of the following features. For example, indicating days during which treatment was applied and days during which treatment was not applied includes indicating the days during which treatment was applied and the days during which treatment was not applied on a calendar. Indicating the days during which treatment was applied and the days during which treatment was not applied on a calendar includes marking days of the calendar during which treatment was applied with a check mark and displaying days of the calendar during which one or more treatments were not applied as unchecked. Storing information about a treatment regimen for use of the medical device, and indicating compliance with the treatment regimen on the calendar. Indicating the days during which treatment was applied and the days during which treatment was not applied occurs in response to the medical device being powered on.

Determining the geographic location of the medical device, and disallowing commencement of treatment using the treatment module if the determined geographic location is outside an authorized geographic location. Determining user identity, and disallowing commencement of treatment using the treatment module if the determined user identity does not match an authorized identity. Controlling the treatment module to apply a treatment includes controlling the treatment module to produce a pulsed ultrasound signal having a frequency in the range of 1 MHz to 2 MHz, consisting of pulses generated at a rate in the range of 100 Hz to 10 KHz with each pulse having a duration in the range of 10 microseconds to 2,000 microseconds. The pulsed ultrasound signal has a power intensity of 100 milliwatts per square centimeter or less.

According to another general aspect, a computer-readable storage medium storing instructions that, when executed by one or more processing devices, cause the one or more processing devices to perform the operations of the computer-implemented methods.

According to another general aspect, a medical device includes: at least one treatment module configured to apply a treatment to a patient, the treatment module including at least one ultrasound transducer and at least one driver circuit coupled to the ultrasound transducer; an interface configured to operatively connect to a removable storage device storing authorization data that identifies a level of treatment authorization; and at least one processing device. The at least one processing device is configured to perform the following in response to receiving user input indicating a treatment should be initiated: determine whether the removable storage device is valid for use with the medical device; if the removable storage device is determined to be valid, access the authorization data; determine whether the treatment is authorized based on the accessed authorization data; if the treatment is determined to be authorized, control the treatment module to apply the treatment by producing ultrasound with therapeutic properties; and if the treatment is determined to not be authorized, control the treatment module such that the treatment is not applied.

The one or more processing devices are further configured to: identify a treatment regimen that identifies a prescribed use of the medical device; compare the information about a recorded use to the prescribed use of the medical device; and generate information indicating the degree that the recorded use matches the prescribed use.

The details of one or more implementations are set forth in the accompanying drawings and the description below. Other features and advantages will become apparent from the description, the drawings, and the claims.

BRIEF DESCRIPTION OF THE DRAWINGS

FIGS. 20 and 21 are diagrams illustrating a system for activating a medical device.

DETAILED DESCRIPTION

Figure 1:
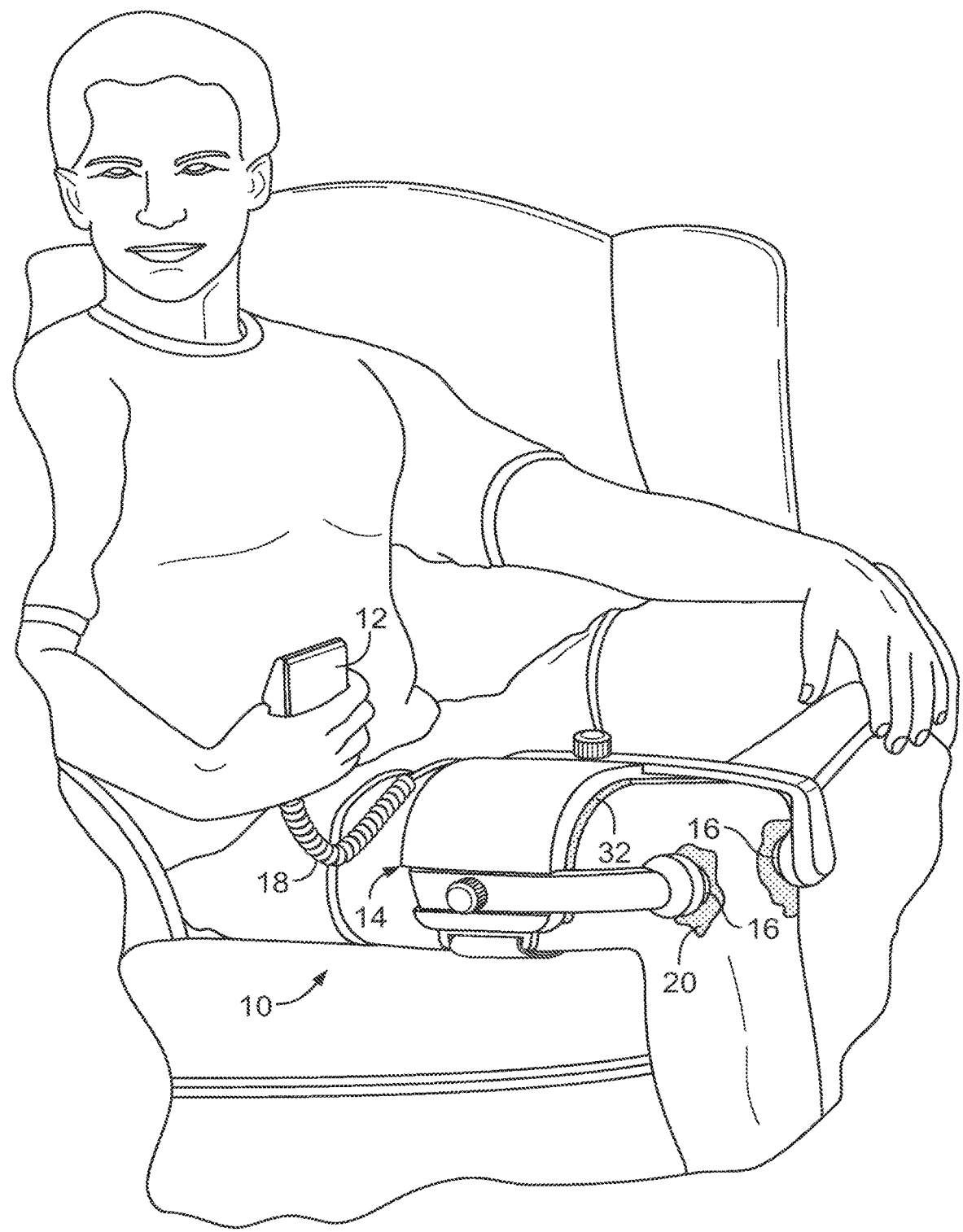
FIG. 1 is a perspective view of a medical device.

In some implementations, a medical device can control its operation to apply treatments that have been purchased and to not apply treatments that have not been purchased. For instance, the medical device can be authorized to provide a particular number of treatments purchased for a patient. When the purchased treatments are exhausted, the medical device can be authorized to perform additional treatments based on additional payment. For example, a user can purchase a card or other removable medium that authorizes a number of additional, prepaid treatments with the medical device. The medical device can access authorization data stored on the removable medium, determine that treatment is authorized, and perform the appropriate treatment.

In addition, or as an alternative, to the above-mentioned features, the medical device can also store information and provide information to a patient. For example, the medical device may provide instructions for using the medical device or information about a particular health condition. The medical device can select the information to provide based a particular health condition of the patient or other information about the patient.

In addition, or as an alternative, to the above-mentioned features, the medical device can record compliance information that indicates occurrences of treatments using the medical device. For example, the compliance information can indicate days and/or times that a patient has performed treatments using the medical device. The compliance information can also indicate the degree to which a patient has complied with a particular treatment regimen. The compliance information can be collected at a server system, and the information can be accessed by multiple parties. The level of access that a party receives can be limited based on the party's relationship to the patient. The server system can receive, store, and provide access to compliance information from multiple medical devices operated by different patients. The medical device can also record errors in the operation of the medical device, send the errors to a server system, and receive service information to address the errors.

In addition, or as an alternative, to the above-mentioned features, the medical device can display information to a patient that indicates the recorded compliance information. The medical device can display a calendar indicating days on which treatment was performed and days on which treatment was not performed. The calendar can also indicate whether or not the treatments that were performed occurred according to the scheduled treatments indicated by a particular treatment regimen for the patient.

In addition, or as an alternative, to the above-mentioned features, the medical device can limit restrict unauthorized use based on an identity of a user or the geographical location of the medical device. The medical device can determine the geographic location of the medical device and not allow treatment to commence if the determined geographic location is outside an authorized geographic region. The medical device can also determine the identity of a user and not allow treatment if the determined identity is not any authorized identity.

Some implementations of the medical device may provide the following advantages. For example, rather than incur a large initial expense by purchasing a medical device with unlimited treatments, in some instances, a patient or third-party payer may pay for only the treatments that are prescribed to the patient. By purchasing treatments as needed, patients and third-party payers may also spread expenses over time. Also, when treatments can be authorized after an initial set of treatments is exhausted, the additional use of the medical device can be easily added. Additional treatments can generally be authorized without service, repair, or reconditioning of the medical device. In some instances, the patient may enter payment directly at the medical device and receive treatment with minimal delay after payment is complete. In addition, by providing only treatments that have been purchased, excessive treatment and misuse of the medical device can be deterred.

Some implementations of the medical device may provide the following additional advantages. Information can be displayed to the patient during treatment, including, for example, information about a health condition of the patient, instructions for using the medical device, and information about the patient's compliance with a treatment regimen. Messages may, for example, encourage, motivate, inform, entertain, and instruct the patient.

Some implementations of the medical device may provide the following additional advantages. Compliance information may be collected and sent to a server system. Security measures can be implemented so that insurance companies, physicians, and caretakers can receive access to the compliance information based on their relationship to the patient. The server system may receive information about errors that occur during operation of the medical device, and the server system may send service information to address the errors.

Some implementations of the medical device may provide the following additional advantages. Medical devices can be maintained in a deactivated state until activated in a controlled process, reducing incentive for theft and misuse. The ability of devices to activate medical devices and authorize medical treatments can be controlled. The number of medical device activations that can be performed by a device can be limited to the inventory associated with the device.

Some implementations of the medical device may provide the following additional advantages. Information indicating a patient's usage of a medical device over time and compliance with a treatment regimen can be displayed. The patient's compliance with a treatment regimen can be easily discernable from a calendar display indicating days on which treatment occurred.

Some implementations of the medical device can limit use by unauthorized users.

Some implementations of the medical device can also limit use outside an authorized geographical area.

Referring to FIG. 1, a patient is shown using a medical device 10 that includes a treatment module for applying a treatment to the patient. In the example illustrated, the medical device 10 is a portable ultrasonic treatment device. The treatment module may include, for example, one or more ultrasound transducers 16 and at least one driver circuit coupled to the ultrasound transducers 16.

The medical device 10 can include a control unit 12 that controls the operation of the transducers 16. The control unit 12 can include the transducer driver circuit. The medical device 10 can also include cables 18 that can carry power, data, and control signals between the control unit 12 and the transducers 16.

The medical device 10 can include a placement module 14 that couples the transducers at a location of the patient's body where treatment is needed, for example, over a fractured bone or next to damaged connective tissue. The placement module 14 can include a band, sleeve, applicator, or other connector to fasten the one or more transducers to a treatment site. An ultrasound conducting gel 20 can be applied to the skin of the patient to enable the ultrasound to propagate effectively to the patient's tissue.

The medical device 10 can use low intensity, high-frequency acoustic energy (ultrasound) to treat injuries, defects, or pathologies. For instance, the ultrasonic treatment device can be designed to treat injuries, defects, or pathologies of bones or connective tissue, and, in some instances, can increase cellular level activity that leads to healing of ischaemic or grafted tissue. The medical device 10 may be used as an adjunct to surgical repair, in order to speed healing, or in some cases can be used alone to heal tissue injuries without surgery (e.g., for degenerative diseases such as osteoarthritis, tendinosis, and tendonitis). The medical device 10 can be suitable for use in treatment of bone fractures and/or connective tissues associated with joints, such as those in the hand, foot, wrist, ankle, knee, elbow, hip, shoulder, back, and neck.

For example, following surgery, the medical device 10 can be applied non-invasively to the outside of the body (e.g., coupled to the skin with coupling media, such as a gel) in the region of the repaired tissue. The medical device 10 can be operated to transmit ultrasound (for example, in the form of pulses) into the tissue in need of treatment, or at the interface with the uninjured tissues. Exposure to the ultrasound can stimulate a faster, better quality repair of the tissue. At a bone interface, the ultrasound can also stimulate bone repair and bone ingrowth into repair or graft tissue. This can give rise to a faster, stronger repair and improved integration of the interface between, for example, tendon, ligament, and bone. The ultrasonic treatment device may also be used to non-invasively treat pathologies of connective tissues, such as osteoarthritis, ligament and tendon conditions, without the need for a surgical procedure.

Figure 2:
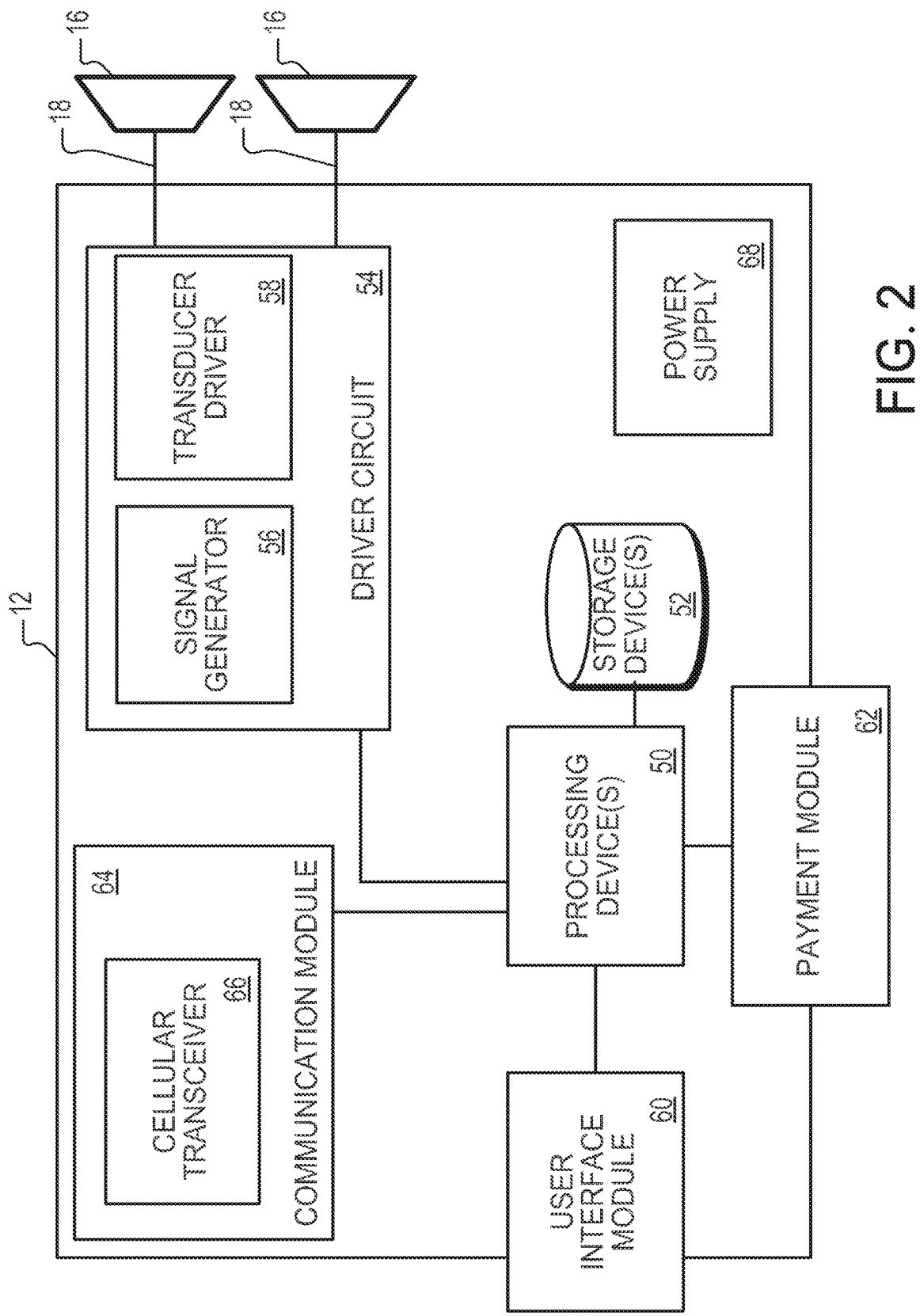
FIG. 2 is a block diagram of the medical device.

Referring to FIG. 2, the control unit 12 of the medical device 10 can include a processing device 50 that executes instructions stored on a storage device 52. The processing device 50 can include one or more processing devices. The storage device 52 can include one or more storage devices, one or more of which may be removable. The control unit 12 can also include a driver circuit 54, a user interface module 60, a payment module 62, a communication module 64, and a power supply 68.

By executing the instructions stored on the storage device 52, the processing device 50 can, for example, determine whether a treatment is authorized. If treatment is authorized, the processing device 50 can control the treatment module (for example, driver circuit 54 and transducers 16) to apply the treatment. Applying the treatment can include controlling the driver circuit 54 to produce ultrasound with therapeutic properties. Controlling the driver circuit 54 to produce ultrasound can include activating the driver circuit 54, for example, supplying power to the driver circuit 54, sending control signals to the driver circuit 54, or causing the driver circuit 54 to produce a particular output. If the treatment is not authorized, the processing device 50 can control the treatment module such that the treatment is not applied. For example, the processing device 50 can control the driver circuit 54 such that ultrasound with therapeutic properties is not produced. Controlling the driver circuit to not apply treatment can include not activating the driver circuit 54, deactivating the driver circuit 54, setting the output of the driver circuit 54 (for example, setting the amplitude to zero), and/or otherwise limiting or preventing treatment. The processing device 50 can also be configured to control other components described below, for example through instructions stored on the storage device 52.

The processing device 50 can determine whether a treatment is authorized by, for example, accessing authorization data. If, for example, accessed authorization data is invalid, is for a different medical device 10, has expired or all treatments associated with the code have been expended, or if no authorization data can be accessed, the processing device 50 can determine that treatment is not authorized. On the other hand, if valid authorization data can be accessed, the processing device 50 determines whether at least one treatment using the medical device 10 is authorized. The authorization data may or may not include an authorization code that indicates that payment for treatments has occurred. The authorization data can be stored in the storage device 52, for example, or, as described further below, in a removable medium.

The storage device 52 can store a device identifier, such as a serial number, that identifies the particular medical device 10. The device identifier can uniquely identify the medical device 10 and distinguish it from all other ultrasonic treatment devices, even those of the same type or model. The storage device 52 can also store information about the treatments that are authorized for the medical device 10, for example, a number of treatments that are authorized or an authorization code that authorizes treatments.

The driver circuit 54 can be configured to send drive signals that cause the transducers 16 to generate ultrasound with therapeutic properties. The driver circuit 54 can include a signal generator 56 that generates a signal and a transducer driver 58 that drives the transducers 16 according to the generated signal. In an implementation, the ultrasound generated by the transducers 16 can include low intensity ultrasound (for example, 100 mW/cm$^2$ or less) having a frequency ranging between about 1 and 2 MHz, more particularly about 1.5 MHz. The ultrasound can be pulsed, with a pulse width ranging from about 10 to 2,000 microseconds, more particularly about 200 microseconds, with a repetition frequency ranging from about 100 Hz to about 10 KHz, more particularly about 1 KHz.

The user interface module 60 can provide information to the patient and enable treatment to be initiated. The user interface module 60 may include one or more input devices or controls, for example, buttons, a keypad, or a touch-sensitive screen. The user interface module 60 may be used by a patient or other person, for example, to enter user input that indicates that a treatment should be administered by the medical device. When the processing device 50 determines that treatment is not authorized, the processing device 50 can provide an indication to the patient on the user interface module 60 that more treatments need to be purchased.

The user interface module 60 may also include one or more output devices, for example a screen, a liquid crystal display, or lights. For example, the interface module 60 can include a screen 72, for example, a liquid crystal display (LCD), a thin-film transistor (TFT) display, a field sequential display, or an organic light-emitting diode (OLED) display. The interface module 60 can also include light-emitting diodes (LEDs) and other indicators. The interface module 60 may include a speaker or other device that can produce sound (not shown), or other output devices. The user interface module 60 may also include input capabilities or input devices (not shown), for example, buttons, one or more keypads, and other controls. The screen 72 may be touch-sensitive to receive input from a user. The user interface module 60 can also include an interface to access a removable storage medium, such as a subscriber identity module (SIM) card, a Secure Digital (SD) card, or other types of removable storage media.

The payment module 62 can enable a patient to enter payment at the control unit 12, or to receive information indicating prior payment. Payment can be enabled through one or more methods. The payment module 62 can include a credit card reader that reads a card and charges treatment to a credit card, debit card, or similar card that is swiped at the control unit 12. The payment module can include a SIM card reader, and a patient may purchase a SIM card that includes information that represents one or more payments made for treatment with the ultrasonic treatment device. The payment module can include a reader for reading other types of removable media, for example, a SD card or other flash memory device. The control unit 12 can be configured to receive payment in the form of a code or other user input that may be entered on the interface module 60. Some implementations may exclude the payment module 62. For instance, in some implementations, provisions may be made to allow payment remotely from the device 10, for example, at a computer connected to a network.

The communication module 64 can be configured to send payment information to a remote system and/or receive authorization information that authorizes additional treatments using the medical device 10.

In some implementations, the processing device 50 is configured to receive an authorization code or other authorization data through the communication module 64 and to store the received authorization code in the storage device 52. The communication module 64 can enable communication with a server system, client system, or other computer system over a wired or wireless connection. The communication module 64 may enable a communication link that is wired or wireless. The communication module may enable communication over, for example, Ethernet, Universal Serial Bus, 502.11, Bluetooth, Zigbee, cellular networks, and other communication links. In one implementation, the communication module 64 can include a cellular transceiver 66 to receive and/or transmit information over a cellular network. The communication module 64 may also enable communication through multiple communication links.

The communication module 64 can be configured to send payment information to a remote system and/or receive authorization information that authorizes additional treatments using the medical device 10. The processing device 50 can be configured to receive an authorization code through the communication module 64 and to store the received authorization code in the storage device 52.

A power supply 68 can provide power to the components of the medical device 10, including the driver circuit 54, the processing device 50, the storage device 52, the payment module 62, the communication module 64, and the user interface module 60. The power supply 68 can include a battery that is integrated into the control unit 12 or is removable. The battery can be primary battery or a rechargeable battery, and the power supply 68 can include a detachable power adapter that can charge a rechargeable battery.

When a user performs treatment using the medical device 10, the medical device 10 can collect and store compliance information. Collecting compliance information can include recording information about use of the medical device 10, for example recording the number of treatments that are performed. Compliance information can include a number of treatments provided by the medical device 10, a date and time that a treatment was provided by the medical device 10, and/or a duration that a treatment was provided by the medical device 10. Information about multiple uses or treatments with the medical device 10 can be collected.

A treatment regimen that identifies a prescribed use of the medical device 10 can be identified. For example, the treatment regimen may be entered on the device after the health condition has been diagnosed or after the medical device 10 has been prescribed to the patient. Information about a treatment regimen may be entered on the medical device 10 or received from a network, which may include a cellular network. The information about the recorded use of the medical device 10 can be compared to the information about the prescribed use of the medical. Information indicating the degree that the recorded use matches the prescribed use can be generated.

Compliance information can be stored on the storage device 52, on a removable medium, or both the storage device 52 and a separate removable medium. The compliance information may, but is not required to, include one or more results of a comparison between the recorded use of the medical device 10 and the treatment regimen of the patient.

Figure 3:
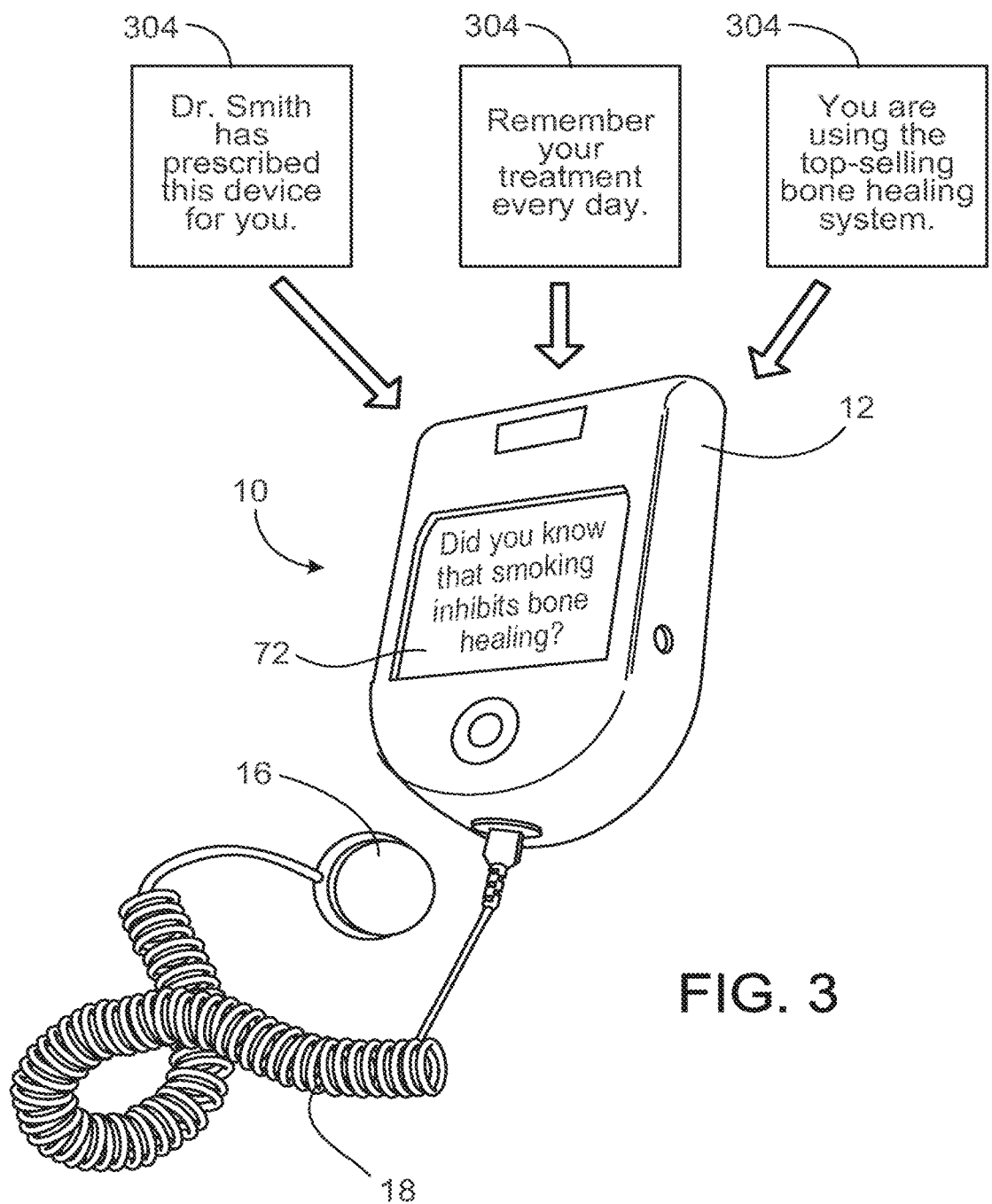
FIG. 3 is a diagram of the medical device configured to display information.

Referring to FIG. 3, the medical device 10 can display information to the patient. For example, the medical device 10 can display information that relates to the particular patient using the medical device 10, for example, information about a health condition of the patient, a treatment regimen of the patient, or a physician of the patient. The information displayed on the medical device 10 can thus be personalized to the particular patient that receives the medical device 10 and a particular health condition of the patient. In some instances, the information displayed may be selected to instruct, encourage, or entertain the patient. In addition, the information can provide advertisements and personalize treatment using the name or brand of, for example a particular physician, hospital, or insurance company.

The information displayed on the medical device 10 may be organized into a plurality of messages 304. Messages 304 can include a variety of media, including text, images, video, and sound. Messages 304 can be stored on the storage device 52 of the control unit 12. Some messages 304 may be entered onto medical device 10 during manufacturing. For example, an initial set of predetermined messages 304 may be loaded onto a storage device 52 before it is shipped. Messages 304 may also be entered at other times to supplement the initially loaded messages 304, including before a medical device 10 is dispensed to a patient and after a patient begins use of the medical device 10. Messages 304 may be received with, for example, the communication module 64 and may be stored on the storage device 52.

Messages 304 can include information related to specific health conditions. For example, some messages 304 may relate to treatment of broken bones of the foot, and others may relate to treatment of broken bones of the arm. The medical device 10 can store messages 304 that relate to a wide variety of health conditions. To ensure that the messages 304 displayed to the patient are useful, the processing device 50 can access information that identifies a health condition of the patient, which can be stored on the storage device 52.

Based on the identified health condition, the processing device 50 can select one or more messages out of the set of messages 304 that are stored on the storage device 52. For example, if the processing device 50 determines that the patient has a broken foot, the processing device 50 can select one or more messages 304 related to broken bones of the foot and treatment of a broken foot. The selected messages 304 can be displayed to the patient on the screen 72. In some implementations, the screen 72 may be part of the interface module 60, while in others the 72 screen may be integrated into the control unit 12.

Selected messages 304 can be displayed to the patient during treatment. For example, while a treatment is applied, the medical device 304 can display information to instruct the patient about proper use of the medical device 10. In many instances, a patient receives only minimal instruction about the proper use of the medical device 10 when the medical device 10 is dispensed to the patient. A patient may forget the proper use of medical device and the details of a treatment regimen, especially when the medical device 10 is new. By providing messages 304 that instruct the patient how to use the medical device 10, the patient may be more likely to perform treatment correctly. The instructive messages 304 can be selected based on the health condition of the patient and the associated treatment regimen for the health condition.

The medical device 10 can select and display a variety of other messages 304 during treatment. For example, messages 304 can also provide general health information, such as, "smoking inhibits bone healing" or "tell your doctor if you use blood thinners."

Messages 304 can also be selected based on a patient's compliance to a treatment regimen. The medical device 10 can store information that indicates when the patient should receive treatment. The medical device 10 can also record information indicating when treatment is actually performed. The medical device 10 can compare the planned or prescribed use of the medical device with the actual use of the device and determine how well the patient has complied with the prescribed treatment regimen. The medical device 10 can display messages 304 to the patient that directly or indirectly provide compliance information. For example, messages can provide direct feedback about a patient's compliance. Messages 304 can also be displayed that motivate, encourage, and remind the patient to follow a consistent treatment schedule. Messages 304 can also describe the benefits of continuing treatment or provide information about how the medical device 10 operates.

Messages 304 can also provide physicians and others an opportunity to provide a personalized message. For example, one or more messages 304 may include the name of a patient's physician, the name of the patient's insurance company, or the logo for a hospital. Customized messages 304 can enable physicians and organizations to reinforce their brands and enhance the patient's experience during treatment. Messages 304 can also include contact information, for example, the phone number for the patient's primary physician. Messages 304 can include advertisements and paid content.

Messages 304 can also be provided to entertain a patient during treatment and thus encourage the patient to complete the treatment. In some implementations, the medical device may enable the patient to acquire or input additional content to display on the medical device.

Figure 4:
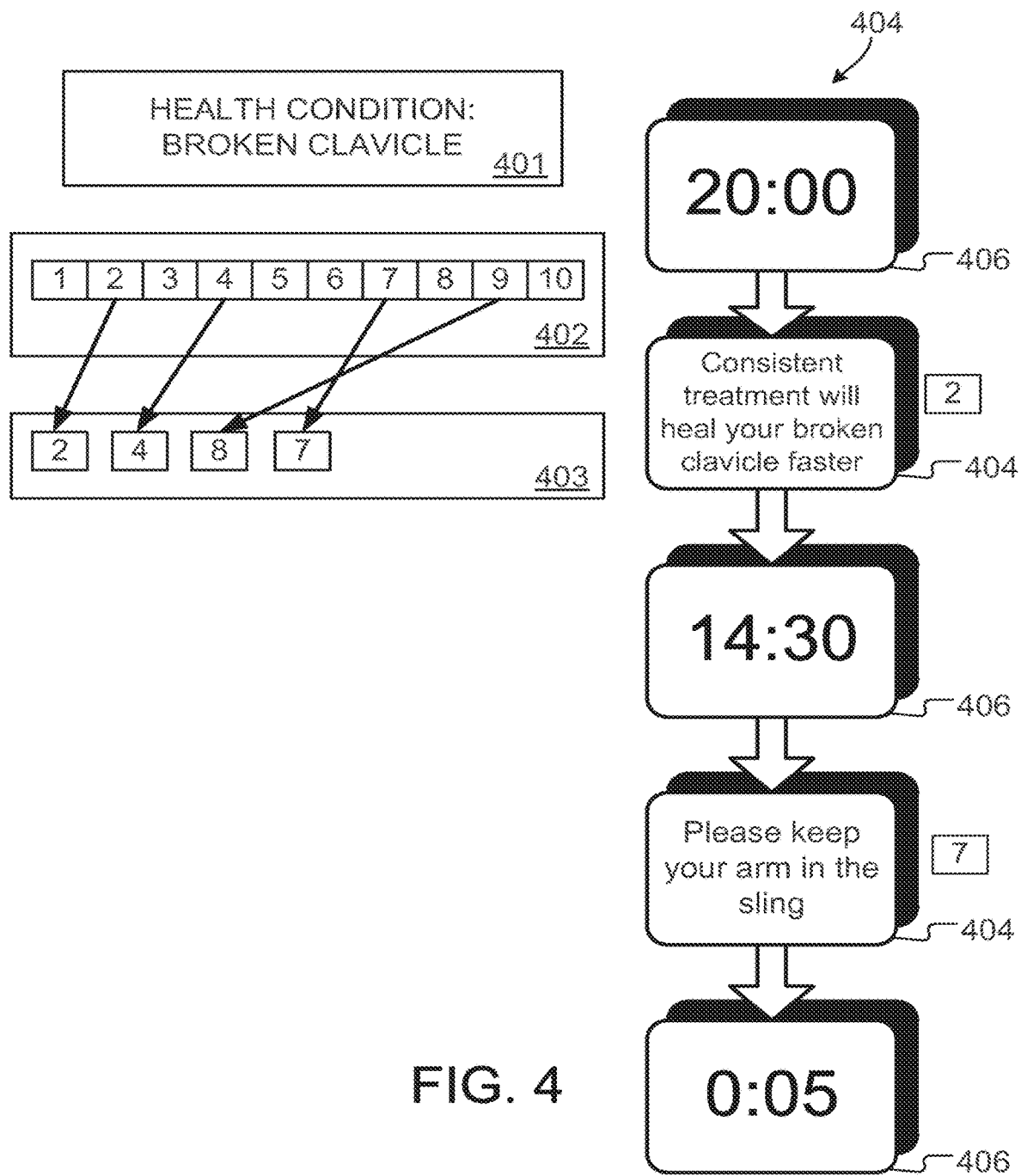
FIG. 4 is a chart illustrating examples of information that may be displayed.

Referring to FIG. 4, a diagram illustrates the selection and display of messages 304 on a screen 72 of the medical device 10.

The processing device 50 of the medical device 10 can access information identifying a health condition of a patient. As illustrated, a health condition record 401 indicates that the health condition of the patient is a broken clavicle. Based on the identified health condition, the processing device 50 can select one or more messages from a plurality of messages 304. The plurality of messages 304 may include a set 402 of predetermined messages 304. Each message 304 in the set 402 may be associated with an identifier, as represented by the numbers from one to ten. From the set 402, a subset 403 of messages 304 may be selected. The selected messages 304 can include messages 304 that relate to the particular health condition of the patient. The selected messages 304 can be ordered into a sequence 404 for display on the medical device 10.

The sequence 404 of messages 304 may be displayed on the screen 72 of the medical device 10. In one implementation, the sequence 404 of messages 304 may begin to be displayed when treatment begins, and the sequence 404 may end roughly when treatment ends. In addition to the messages 304, other information can be included, for example, information that describes the treatment being performed. For example, notifications 406 that indicate the time remaining until treatment is completed may be interspersed between other messages 304.

The messages 304 selected and the sequence 404 of the selected messages 304 can vary according to the needs of the patient and to limit unnecessary repetition. For example, instructions about how to use the medical device 10 may be selected and displayed for an initial set of treatments using the medical device 10, but instructions may be omitted after many treatments have successfully been performed.

Figure 5:
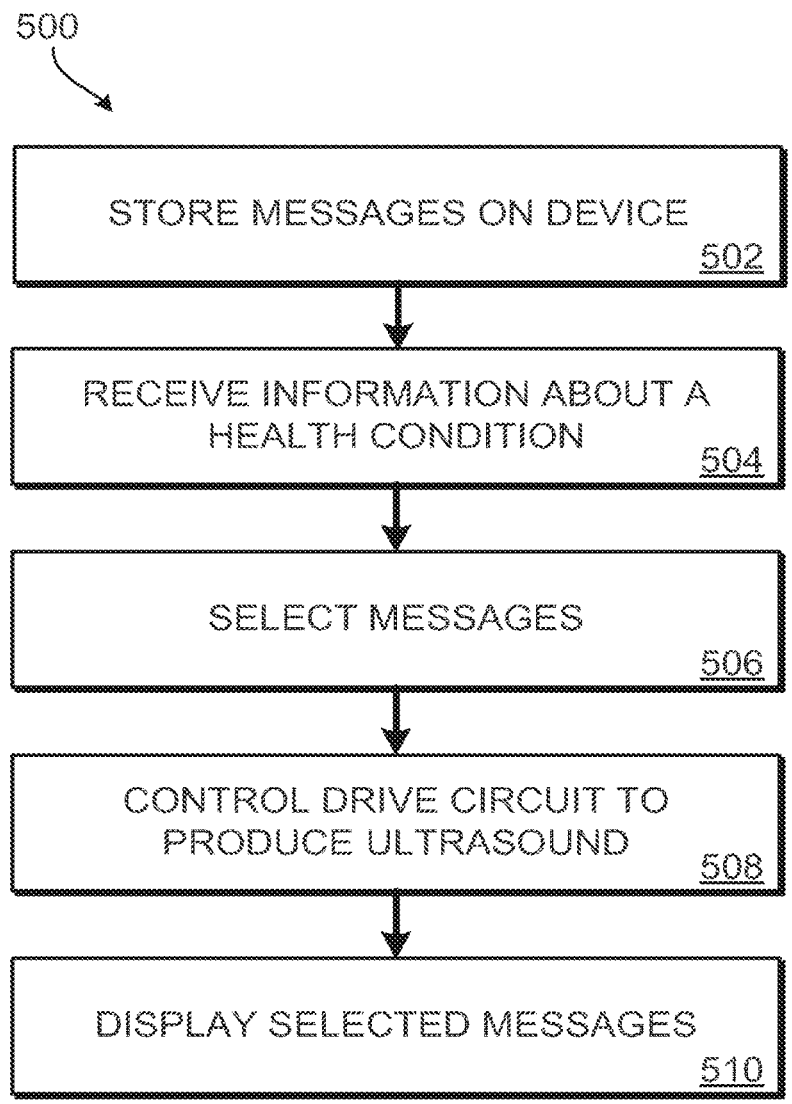
FIG. 5 is a flow diagram illustrating a process for displaying information.

Referring to FIG. 5, an example of a process 500 for providing information is illustrated. The processing device 50 of the medical device 10 can be configured to perform the process 500, for example, by executing instructions stored on the storage device 52.

A plurality of messages is stored on the medical device (502). For example, the storage device may store the plurality of messages. Messages may be entered on the storage device by a manufacturer of the medical device before the medical device is sold. Messages can also be entered on the storage device by sales representatives, physicians, and others at other times.

The medical device receives information about a health condition of a patient (504).

For example, after a patient is diagnosed with a particular health condition, the health condition can be entered on the medical device. A physician, assistant, sales representative, or other person may enter information that indicates the health condition of the patient on the medical device. In addition, or alternately, the medical device may receive information about a health condition of the patient through the communication module. For example, the medical device may receive information about a prescription or diagnosis automatically over a network, without requiring any manual input. The medical device can store the information about the patient's health condition for later access. The health condition can be, for example, a health condition that is treatable by the medical device.

The medical device selects messages for the patient (506). For example, the messages can be selected from the stored messages stored on the storage device. One or more messages can be selected based on the identified health condition of the patient. For example, if the patient has a broken ankle, messages can be selected that describe treatment of a broken ankle. The selected messages can include messages related to multiple health conditions. The selected messages can include instructions for using the medical device. The selected messages can include one or more messages that include information about a doctor that treated the patient or a medical office where the patient was treated. The selected messages can include one or more messages about the medical device or information about the provider of the medical device. The selected messages can include advertisements. The selected messages can include image data or video data.

In some implementations, the medical device can store records indicating use of the medical device. For example, the medical device can record the number of treatments that have been performed using the medical device, the date and time that each treatment is performed, and/or the duration of each treatment. The information in these records, referred to generally as compliance information, indicates the manner in which treatments were performed using the device, from which a patient's compliance with a particular treatment regimen can be determined.

Compliance information can be stored on the one or more storage devices 52. For example, the compliance information can be stored on internal memory of the medical device 10 and can also be stored on a removable medium, such as an SD memory card. Recording the compliance information on internal memory and the removable medium provides a backup in case one of the storage devices should fail. Additionally, the removable medium may be removed and used to transfer compliance information to other systems.

The medical device can also identify a treatment regimen that corresponds to the health condition. For example, the medical device may receive the information from a prescription, a treatment regimen that is entered directly on the medical device, or the medical device may store a number of treatment regimens on the storage device. The medical device can access the records indicating use of the device. The medical device can compare the records indicating use of the medical device to the treatment regimen identified for the health condition of the patient.

The medical device can provide an indication of compliance with the treatment regimen. For example, the medical device may provide an indication of compliance in one or more messages that are selected to be later displayed to the patient. The selected messages can also encourage compliance to a treatment regimen, for example, by praising the patient for past compliance or assuring the patient that continued treatment will bring good results. The selection of messages, including the selection of messages about compliance to the treatment regimen, can be based on the number of uses of the medical device indicated in the records that indicate use of the medical device.

The medical device can also identify the language of the patient and select one or more messages in the language of the patient. The plurality of messages stored on the medical device can include messages in at least two languages. For example, some or all of the stored messages can be included in multiple languages. The medical device can identify the language of the user, for example, based on user input, messages input on the medical device, information received by the communication module, or other information.

The medical device can begin treatment (508). For example, a patient may enter input indicating that treatment should begin, and the medical device may control a driver circuit to drive an ultrasound transducer so that the ultrasound transducer produces ultrasound with therapeutic properties. The medical device can store and update records indicating use of the medical device.

The medical device can display the selected messages (510). The selected messages can be displayed during treatment, for example, while the ultrasound with therapeutic properties is applied to the patient. The messages can be displayed on a liquid crystal display or other screen.

Figure 6A:
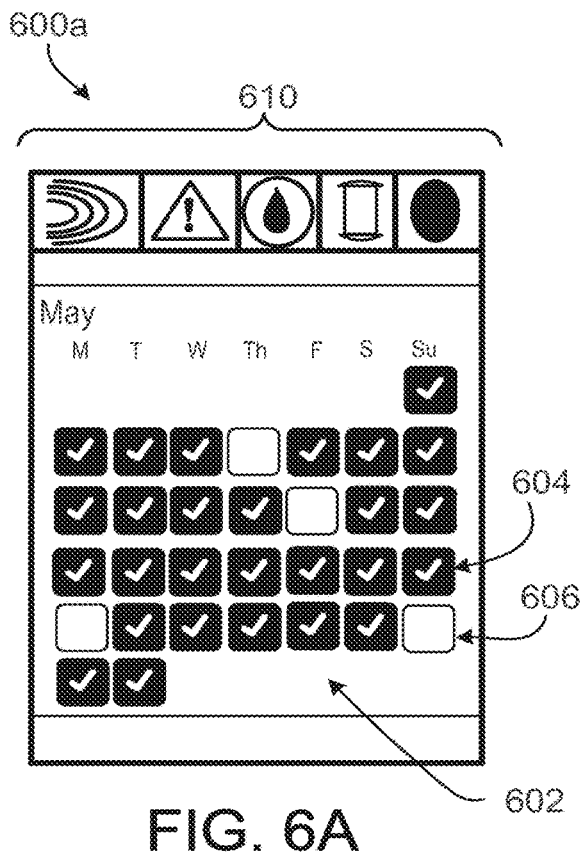
FIGS. 6A to 6C are diagrams illustrating user interfaces for the medical device.

Referring to FIG. 6A, the medical device 10 can display information about a patient's compliance with a treatment regimen on a user interface 600a. The user interface 600a can be displayed on the screen 72 of the user interface module 60. The user interface 600a includes a calendar view 602 that indicates whether treatment was performed each day of, for example, the current month, or the current month and previous months. In the calendar space corresponding to each day that treatment was performed, a compliance indicator 604 can be displayed, for example, a colored square, a check mark, or other image or icon. In the space corresponding to each day in which treatment was not performed, a noncompliance indicator 606 can be displayed, for example, a different image or icon, such as a blank square or a red "X." Thus the user interface 600a can visually distinguish the days during which treatment was performed from days during which treatment was not performed, providing an easily-understandable indication of recent compliance with the treatment regimen.

In some implementations, information about the particular treatment regimen prescribed for the user of the medical device 10 is stored on the medical device 10, and the compliance indicator 604 is displayed to indicate that a treatment performed on a particular day complies with the particular treatment regimen prescribed. In other words, rather than assuming that the treatment regimen requires one treatment each day, the medical device 10 compares times that treatments were performed to times that treatments were scheduled to be performed, as dictated by a treatment regimen. If a treatment regimen involves treatment every other day, for example, a neutral indicator can be displayed to represent days in which treatment was not scheduled and was not performed. The neutral indicator may be, for example, the day of the month that the day occurs. The noncompliance indicator 606 may be displayed, for example, only when treatment was scheduled to be performed on a day and treatment did not occur on that day. If treatment was performed on a day that treatment was not scheduled, an improper treatment indicator different from the noncompliance indicator 606 may be displayed for that day, distinguishing noncompliance by omitted treatment from noncompliance by performance of an unscheduled treatment. As a result, compliance relative to a treatment regimen can be accurately indicated when scheduled treatments are not scheduled every day.

Similarly, compliance can be indicated for treatment regimens that dictate treatment multiple times in a day. For example, multiple compliance indicators 604 or multiple noncompliance indicators 606 can be displayed to indicate each treatment that was completed or missed that day.

In other implementations, the medical device 10 displays the compliance indicator 604 for days that treatment was performed and displays the noncompliance indicator 606 for days that treatments were not performed, without regard to times that treatments were dictated by a prescribed treatment regimen. Thus even when the medical device 10 does not have access to information indicating a treatment regimen, the calendar view 602 indicates when treatments were performed, permitting the user or others to determine compliance with an appropriate treatment regimen.

The user interface 600a may display patient compliance for time period longer or shorter than a month, and for previous periods of time rather than, for example, the most recent weeks or months.

The medical device 10 can automatically display the calendar view 602 as the medical device 10 is powered on or at other times. For example, each time the medical device 10 is powered on, while the medical device 10 is initializing and for a period of time afterward, the calendar view 602 showing compliance can be displayed. The calendar view 602 can also be displayed to physicians, caretakers, and others. The calendar view 602 can be displayed automatically after particular functions of the medical device 10 are accessed, or in response to a request that the calendar view 602 be displayed.

The medical device 10 can automatically display a total compliance to-date indication. For example, if ten days have elapsed since the start of a daily treatment regimen and the patient only used the device for eight out of the ten days, then the total compliance indicator can display 8/10 or 80% to indicate the overall level of compliance.

The user interface 600a can also display notification icons 610. The notification icons 610 can vary in appearance according to the current status of the medical device 10. The notification icons 610 can indicate, for example, the status and availability of communication links such as wireless connections, whether service is needed, that error or notification messages are available, the types or quality of connections with various modules, the remaining battery charge of the medical device, and other notifications.

Figure 6B:
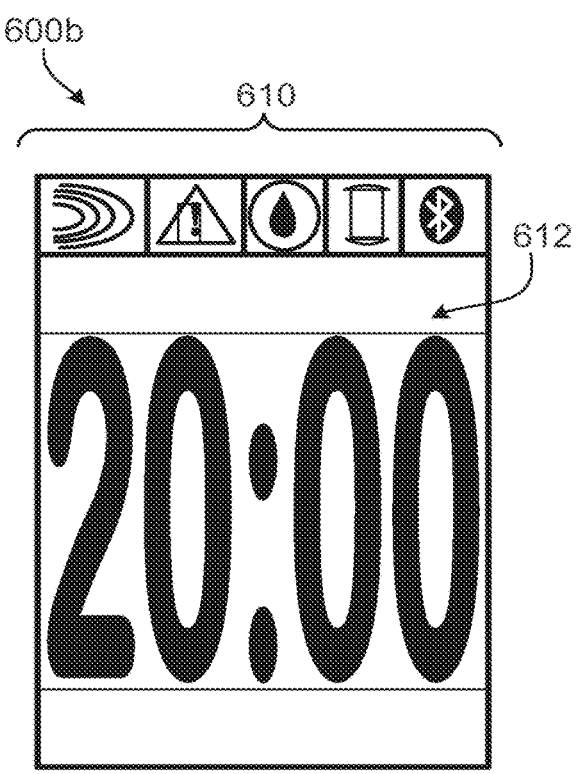

Referring to FIG. 6B, after the calendar view 602 is displayed, or after receiving user input, the medical device 10 can display a treatment timer 612 on a user interface 600b. The treatment timer 612 can indicate the time remaining before a treatment is completed. For example, for a twenty-minute treatment, the treatment timer 612 can initially indicate the duration of treatment, twenty minutes. While a treatment is in progress, the treatment timer 612 can count down toward zero, reaching zero when the treatment ends. The notification icons 61O can also be displayed.

Figure 6C:
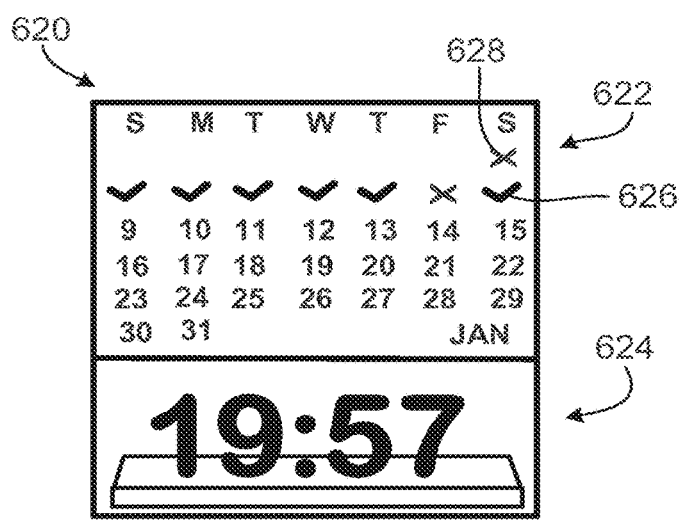

Referring to FIG. 6C, an alternative user interface 620 includes a calendar view 622 indicating daily compliance with the treatment regimen and a treatment timer 624. Days for which treatment was performed as indicated in the treatment regimen are indicated with a first marking 626, while days for which planned treatment failed to be performed are indicated with a different marking 628. Days in the future can be marked with their corresponding calendar numbers.

Figure 7:
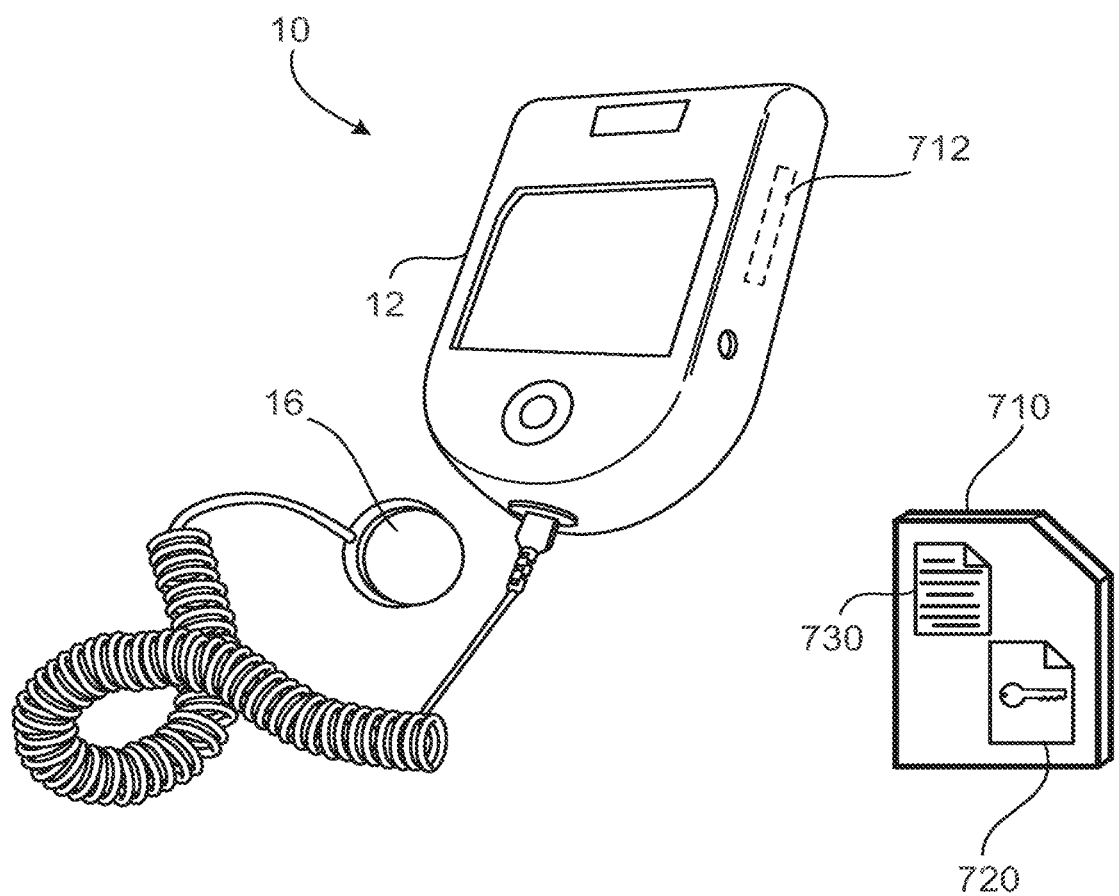
FIG. 7 is a diagram illustrating a medium for authorizing treatment using the medical device.

Referring to FIG. 7, a removable medium 710, for example, an SD card, USB device, or other removable memory device, can be used to authorize use of the medical device 10. The removable medium 710 can store authorization data 720 that indicates a level of treatment authorization, for example, a number of treatments authorized or an amount of treatment time authorized using the medical device 10.

The medical device 10 can include an interface 712 that operatively connects to the removable medium 710, permitting the processing device 50 to access the authorization data 720. The interface 712 can include a slot that receives the removable medium 710 within the medical device 10. The slot can be accessible to a user, permitting the user to replace the removable medium 710 with a different removable medium. The control unit 12 of the medical device 10 can define the slot and can include a cover that covers the slot.

To obtain treatment authorization, the patient can obtain the removable medium 710, which can be a prepaid medium that represents that payment has been made by or for the user. Removable media can store differing levels of treatment authorization. Different removable media may be sold with authorization data 720 that permits, for example, 50, 25, or 10 treatments. Treatment authorization may additionally or alternatively be indicated as an amount of time, for example, 1000, 500, or 100 minutes of treatment. In some implementations, the removable medium 710 can be purchased from a retail store or a physician's office. The fact that the patient obtained the removable medium 710 indicates that payment was made, and no additional verification of payment may be necessary to use the medical device 10.

The removable medium 710 may be a secure mode of communicating that a particular number of treatments are authorized. The removable medium can include a copy-protection or anti-counterfeiting feature that can be used to determine whether the removable medium is genuine. For example, the removable medium can store an encoded value in a manner that the value is not easily duplicated or copied from one removable medium to another. The encoded value can be hardware-encoded or factory-set with a physical setting such that similar removable media cannot be altered to mimic the encoded value. In some implementations, the encoded value is a serial number that is embedded in non-writable storage of the removable medium. Each valid removable medium can have a unique serial number. Only removable media that have a serial number within a predetermined range of values can be considered genuine.

In use, a user interacts with the medical device 10 to indicate that treatment should be initiated, for example, by pressing a button or entering other input. In response, the processing device 50 determines whether a removable medium is present. If no removable medium is present, the processing device 50 disallows treatment.

If a removable medium such as the removable medium 710 is present, the processing device 50 determines whether the removable medium 710 is valid for use with the medical device 10. For example, the processing device 50 determines whether a serial number or other value encoded in the removable medium meets predetermined criteria. In some implementations, the processing device 50 determines whether the value is within a predetermined set or range of values. The serial number can be a value that is not modifiable by a user, for example, a value that is fixed in the hardware configuration of the removable medium and cannot be copied onto a similar removable medium. Thus the processing device 50 can verify that the physical medium is valid. If a removable medium is not genuine, or is not compatible with or intended for the medical device 10, the processing device 50 disallows treatment.

If the removable medium 710 is genuine, the processing device 50 accesses authentication data 720 stored on the removable medium 710. The authentication data 720 can indicate a number of treatments authorized or a number of treatment minutes that treatment is authorized. For example, when each treatment has a duration of twenty minutes, the authorization data 720 may indicate that ten treatments are authorized, or may indicate that two hundred minutes of treatments are authorized. If the authorization data 720 indicates that at least one treatment is authorized, or that one or more treatment minutes are authorized, the processing device 50 controls the treatment module to provide ultrasound with therapeutic properties. If the authorization data 720 indicates that no treatments are authorized, the processing device 50 disallows treatment.

After the medical device 10 applies a treatment, the processing device 50 alters the authorization data 720 to indicate an updated level of authorization. For example, the medical device 10 can decrease the number of authorized treatments or decrease the number of authorized treatment minutes remaining. Modified authorization data that indicates an updated level of authorization can be stored on the removable medium 710, for example, by overwriting the authorization data 720 that was stored before treatment began.

The medical device 10 can also store compliance data 730 on the removable medium 710. When the medical device 10 applies a treatment, the processing device 50 can store information about the treatment performed. For example, the compliance data 730 can indicate the time, date, and duration of the treatment applied, along with other treatment information. The removable medium 710 can thus include a compliance log that indicates use of the medical device 10 over time. The compliance data 730 can also indicate, for example, the degree that the use of the medical device 10 corresponds to planned or prescribed use of the medical device 10. For example, the compliance data 730 can indicate days or times at which treatment was scheduled and whether treatment occurred at those days or times. Compliance data 730 can additionally or alternatively be stored on an internal storage device of the medical device, such as the storage device 52.

In some implementations, the authentication data 720 is encrypted, which can discourage tampering. In such implementations, the processing device 50 decrypts the authentication data 720 before determining whether treatment is authorized. Also, after modifying the authentication data to indicate a decreased level of authorization, the processing device 50 encrypts the modified data and stores the encrypted data on the removable medium 710.

When additional treatments are desired, for example, after the treatment authorization of the authorization data 720 is depleted, a user can obtain a different removable medium that includes authorization data for additional treatments.

In some implementations, the authorization data 720 directly authorizes the treatments, without the medical device 10 needing additional information or confirmation from another system. In some implementations, as described below, the medical device 10 verifies the authenticity of authorization data 720 by communicating with a server system or other device.

Figure 8:
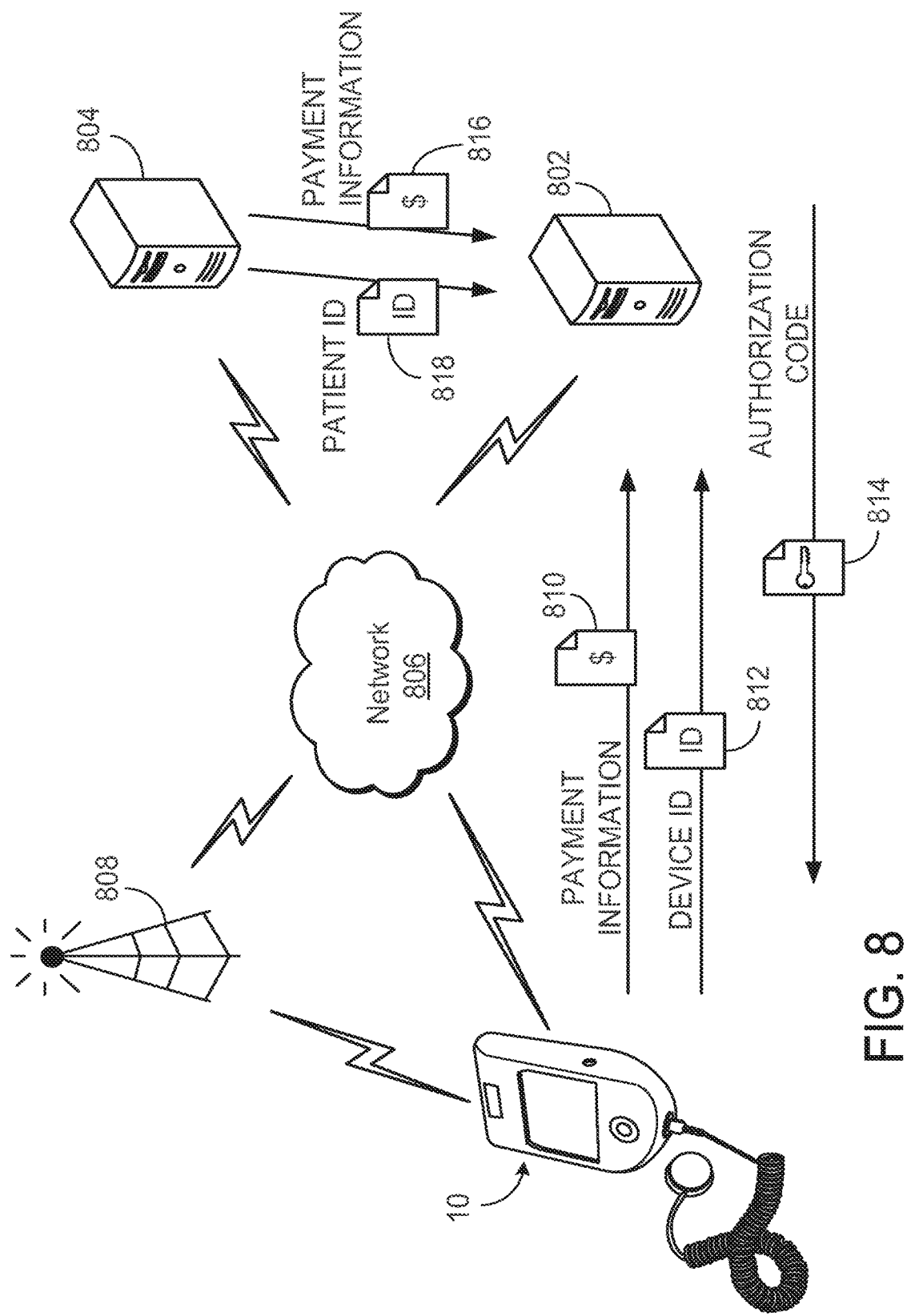
FIG. 8 is a diagram of a system for authorizing medical treatments.

Referring to FIG. 8, a system 800 for authorizing medical treatments includes the medical device 10 connected to a server system 802 via a network 806. The system 800 can also include a third-party server system 804 and a cellular network 808. After payment is made by or for a patient, authorization data can be entered at or received by the medical device 10. The authorization data indicates a level of treatment authorization, and can include an authorization code.

A patient may desire to authorize medical treatments using the ultrasonic treatment device 10. For example, the patient may receive the ultrasonic treatment device 10 in a condition in which treatments have not yet been authorized. As another example, the patient may have used treatments authorized for the ultrasonic treatment device 10 so that an insufficient number of treatments are currently authorized to complete treatment.

To purchase additional treatments of the medical device 10, the patient may provide payment information 810 at the medical device 10. Payment information 810 includes payment entered or authorized at the medical device 10 and also information that indicates that payment has been made in another manner. For example, the patient may enter a credit card, a debit card, or another payment device into an appropriate reader of the medical device 10 and authorize a charge to an account owned by the patient. The patient may also enter an account number on the user interface module 60 of the medical device 10 to authorize payment. The patient may also purchase a prepaid medium, for example, a SIM card, a Secure Digital (SD) card, or a prepaid card with a magnetic strip, an optical code, or a printed code, from a store or physician's office. In one implementation, the prepaid medium may be a secure mode of communicating an amount of payment that has been paid. The patient may enter the prepaid medium at the ultrasonic treatment device 10 to indicate that payment has been made. The patient may also purchase treatments in a store or through a web site, may receive a confirmation code for the transaction, and may enter the confirmation code at the ultrasonic treatment device 10. The system 800 can also be used to verify the validity of an authorization code received from a prepaid medium.

The medical device 10 can send the payment information 810 to a server system 802. The payment information 810 can be associated with a device identifier 812 that identifies the medical device 10, which can also be sent to the server system 802. In addition to, or instead of, sending a device identifier 812, the medical device 10 may send a patient identifier that identifies the patient, together with the payment information. As will be described in greater detail below, the server system 802 can send an authorization code to the medical device 10 after receiving the payment information 810 and the device identifier 812.

The medical device 10 may send the payment information 810 and the device identifier 812 to the server system 802 through the network 806. Alternatively, or additionally, the medical device 10 may initiate a communication using the cellular network 808 to send the payment information 810 and the device identifier 812 to the server system 802. Payment information 810 can also be received through a removable medium, token, code or other indication that treatment is authorized.

In one implementation, a prepaid medium can store an authorization code that can directly authorize treatments, so that the ultrasonic treatment device 10 is not required to transmit any information to the server system 802. A prepaid medium can include an authorization code that can enable treatments of the ultrasonic treatment device 10, independent of a server system 802. For example, a patient may purchase a SIM card or other device that stores an authorization code compatible with the ultrasonic treatment device 10. The SIM card containing the authorization code can be entered at the ultrasonic treatment device 10 and the treatments authorized by the authorization code can be enabled on the ultrasonic treatment device 10. Payment is received by the retail store or physician's office where the prepaid medium was obtained. The fact that the patient obtained the prepaid medium proves that payment was made, and no additional verification may be necessary. In some implementations, the ultrasonic treatment device 10 may verify that the authentication code included with the prepaid medium is authentic, and may ensure that the authentication code of the prepaid medium is not used multiple times (for example, by altering the data on the prepaid medium). In another implementation, a mechanical device or key may also be used to indicate authorization of additional treatments of the ultrasonic treatment device 10.

Treatments can also be purchased for a patient by a third-party payer, for example, an insurance company. A third-party server system 804 can transfer payment information 816 to the server system 802 with a patient identifier 818 that identifies the patient. The payment information 816 can include the information that completes the act of payment or indicates that payment has been made. The patient identifier 818 can include a name, prescription number, insurance policy number, or other identifier.

The server system 802 can receive the payment information 810 and the device identifier 812 from the medical device 10, or can receive the payment information 816 and the patient identifier 818 from the third-party server system 804.

The server system 802 can determine that payment has been made for a number of treatments, for example, using the payment information 810, 816. The server system 802 can also determine that patient is associated with the medical device, for example, using the patient identifier 818 or device identifier 812 associated with the payment information 810, 816. The server system 802 can use the received information and stored records to associate the payment with the patient to be treated with the medical device 10. The server system 802 may store records that associate patient identifiers 818 and device identifiers 812 with particular patients and medical devices 10 so that payment can be applied for the correct patient and medical device 10.

The server system 802 can also generate an authorization code 814 that enables the medical device 10 to provide a number of treatments. The number of treatments authorized can be based on the amount of payment received. The server system 802 can send the authorization code 814 to the medical device 10 through the network 806 and/or through the cellular network 808.

The authorization code 814 can be encrypted or encoded so that the authorization code 814 enables treatments only for the particular medical device 10 associated with a particular payment received. In one implementation, the authorization code 814 can be encrypted so that the unique device identifier 812 or another unique decryption key is necessary to decrypt or decode the authorization code 814. For example, the authorization code 814 can be encrypted using a symmetric-key or asymmetric-key encryption scheme.

Using a symmetric-key or shared-key encryption system, a key may be used as both the encryption and decryption key. The key can be stored on both the server system 802 and the medical device 10, for example, by the manufacturer of the medical device 10. To prevent interception, the key may not be transmitted. The medical device 10 can send a patient identifier or a device identifier 812 unrelated to the key to identify the medical device 10. The server system 802 can send the encrypted data to the medical device 10, which can decrypt the data with the stored key.

Using an asymmetric-key cryptography system, for example, a public key private key pair encryption system, the server system 802 can store an encryption key and the medical device 10 can store a corresponding decryption key. The server system 802 may encrypt the authorization code 814 using the encryption key and send the encrypted data to the medical device 10. The medical device 10 can include a stored decryption key that can decrypt the encrypted data. The decryption key can include the device identifier 812 or another key. In an implementation, the encryption key that encrypts messages for a particular medical device 10 may be known only to the server system 802.

Because the server system 802 can store records associating patients, medical devices 10, and corresponding encryption keys, the system 800 may not require that the decryption key be sent to the server system 802. If the device identifier 812 is used to decrypt an authorization code 814, instead of sending the device identifier 812, the medical device 10 can send another identifier, such as a patient identifier or a device identifier unrelated to the encryption scheme. The device identifier 812 can be independent of the encryption scheme so that interception of the device identifier does not compromise the encryption scheme.

The medical device 10 can receive the encrypted authorization code 814 through the network 806 or the cellular network 808 and can decrypt the authorization code 814. The medical device 10 can use the authorization code 814 to authorize a number of treatments of the medical device 10. The authorization code 814 or information determined based on the authorization code 814 can be stored to indicate the number of treatments authorized. When the patient attempts to initiate treatment with the medical device 10, the processing device of the medical device 10 can determine that authorized treatments remain for the medical device 10 and initiate treatment.

The medical device 10 may also use the authorization code 814 to determine a change in treatment. For example, an authorization code 814 may indicate that treatment should be disallowed after a particular period of time has elapsed or if the patient does not apply a treatment for a period of time. The authorization code 814 may indicate that the number of treatments that are available each day should be changed, for example, from one treatment each day to two treatments each day. The authorization code 814 may indicate that the intensity of ultrasound produced by the medical device 10 should be changed, for example, that the intensity should be reduced if the patient is healing well.

Figure 9A:
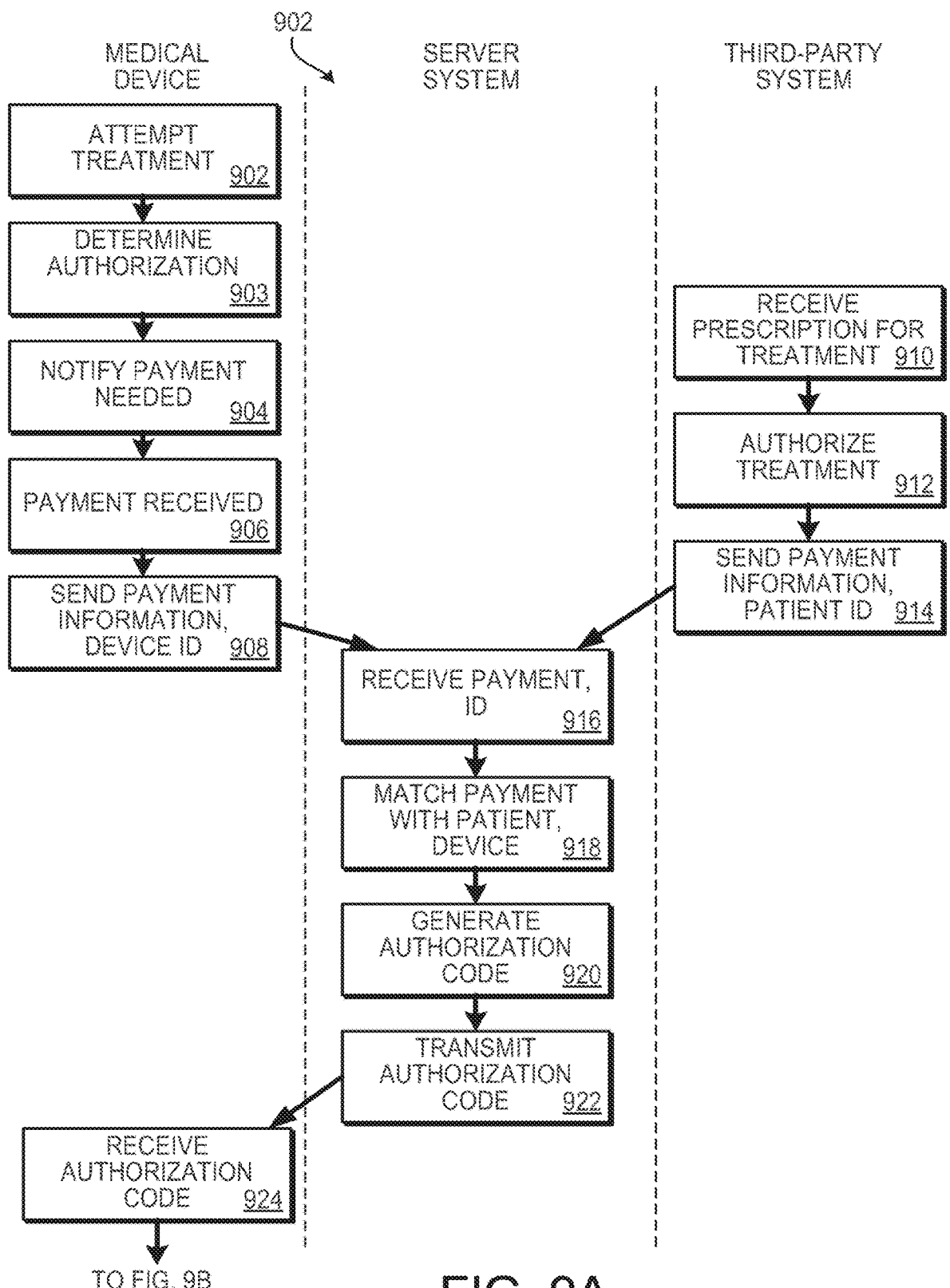
FIGS. 9A and 9B are flow diagrams of a process for authorizing medical treatments.

Referring to FIG. 9A, a process 900 for authorizing medical treatments can include actions by a medical device, a server system, and/or a third-party system. The medical device can be an ultrasonic treatment device as described above.

As illustrated, the process 900 can include payment for treatment by a patient at the medical device, payment by a third-party at a remote system, or both sources of payment. The actions performed by the medical device can be performed by one or more processing devices of the medical device configured to perform those actions. The server system can include one or more processing devices and one or more storage devices that store instructions that, when executed by the one or more processing devices, cause the processing devices to perform the various functions of the server system described below.

A patient can attempt to initiate treatment with the medical device (902). For example, the medical device can receive user input indicating that a treatment should be administered by the medical device.

The medical device can determine whether treatment is authorized (903). For example, the medical device can determine whether at least one treatment is authorized based on stored information that indicates the number of treatments that are authorized. The medical device can access an authorization code that has been received, for example, and determine whether treatment is authorized based on the accessed authorization code. The determination whether the attempted treatment is authorized can be performed in response to the attempt to initiate treatment in (902).

If the determination indicates that treatment by the medical device is authorized, the medical device can control a treatment module to apply the treatment that the patient attempted. If the determination indicates that treatment is not authorized, the medical device can control the treatment module so that the treatment attempted by the patient is not applied. No treatment may be authorized for a medical device if, for example, all of the previously authorized treatments have already been used or if the medical device has not received an initial authorization code to enable treatments.

When treatment is not authorized for the medical device, the medical device can notify the patient that payment is needed to purchase additional treatments (904). The example illustrated in FIG. 9A shows a scenario in which the medical device is not initially authorized to perform a treatment attempted by a patient, so additional payment and authorization of the medical device is needed.

Payment can be received at the medical device (906). The patient can then enter payment in one or more ways, including entering payment at the medical device using, for example, a credit card or a debit card to purchase additional treatments. The patient may also complete payment at a location other than the medical device, and enter proof of payment at the medical device. The patient may purchase treatments for example, at a store, at a medical office, or over the Internet. The patient may then enter proof of payment at the medical device in the form of, for example, a computer file, a code, or a SIM card.

The medical device can then send payment information for the payment received and an identifier to the server system (908). The identifier may be a device identifier that uniquely identifies the particular medical device used by the patient. In other words, the device identifier can identify not merely a model or type of medical device, but a single, particular medical device. The identifier may be a patient identifier that identifies a particular patient associated with the medical device.

Treatments can also be purchased for a patient by a third-party, for example, an insurance company. The third-party system can receive, for example, a prescription for treatment of the patient using the medical device (910). The third-party system can authorize one or more treatments using the medical device (912). For example, the third-party system can authorize the treatments identified in the received prescription.

The third party system can send payment information and an identifier to the server system (914). The payment information can include information that enables a transaction to occur, for example, an authorization to charge an account or otherwise cause funds to be transferred, and can include information that indicates that payment has been performed. The identifier can identify the patient associated with the prescription that was received in action (910). For example, the identifier can include a name of the patient, an insurance policy number for the patient, a prescription identifier, or other information relating to the patient. The identifier may also identify the medical device for the patient.

The server system can receive payment information and an associated identifier from either the medical device or the third party system (916). The associated identifier can be a device identifier that uniquely identifies the medical device. The server system can match the payment described in the payment information with the patient and the medical device of the patient (918). The server system can store one or more associations between a patient and the medical device configured to apply a medical treatment to the patient. For example, the server system can store records that associate patients with particular medical devices, patient identifiers, and medical device identifiers.

The server system may use one or more received identifiers to determine which patient and device are associated with a payment. Specifically, the server system can determine that payment has been made for the patient for a particular number of treatments by the medical device. The determination can be made based on the received information that payment has been made for the patient. The server system can identify the medical device associated with the patient based on the stored association between the patient and the medical device and, for example, based on a received device identifier that uniquely identifies the medical device. The server system may also record the determination that payment has been made for the user and the identification of the medical device associated with the patient.

The server system can generate an authorization code that can authorize the medical device associated with the patient to perform the purchased treatments (920). The authorization code can enable the number of treatments purchased by the patient or third-party payer. The authorization code can be generated so that the code only enables treatments of the particular medical device associated with the patient for whom payment was received. For example, the authorization code may be encoded or encrypted so that only the particular medical device associated with the payment can decode or decrypt the authorization code. The authorization code may include or be transmitted with a unique device identifier, and a medical device can be configured to enter an authorization code only when a device identifier of the medical device matches the device identifier received with an authorization code.

The server system can transmit the authorization code to the medical device (922).

The authorization code may be transmitted, for example, over a cellular communication link to the medical device that the server system identified as being associated with the patient.

The medical device can receive the authorization code (924). The authorization code may be a new authorization code that is received after an initial or prior authorization code that authorized different treatments. The new authorization code can be received after the medical device has provided an indication to the patient that more treatments need to be purchased, and the new authorization code can identify a number of additional treatments for which payment has been received.

Figure 9B:
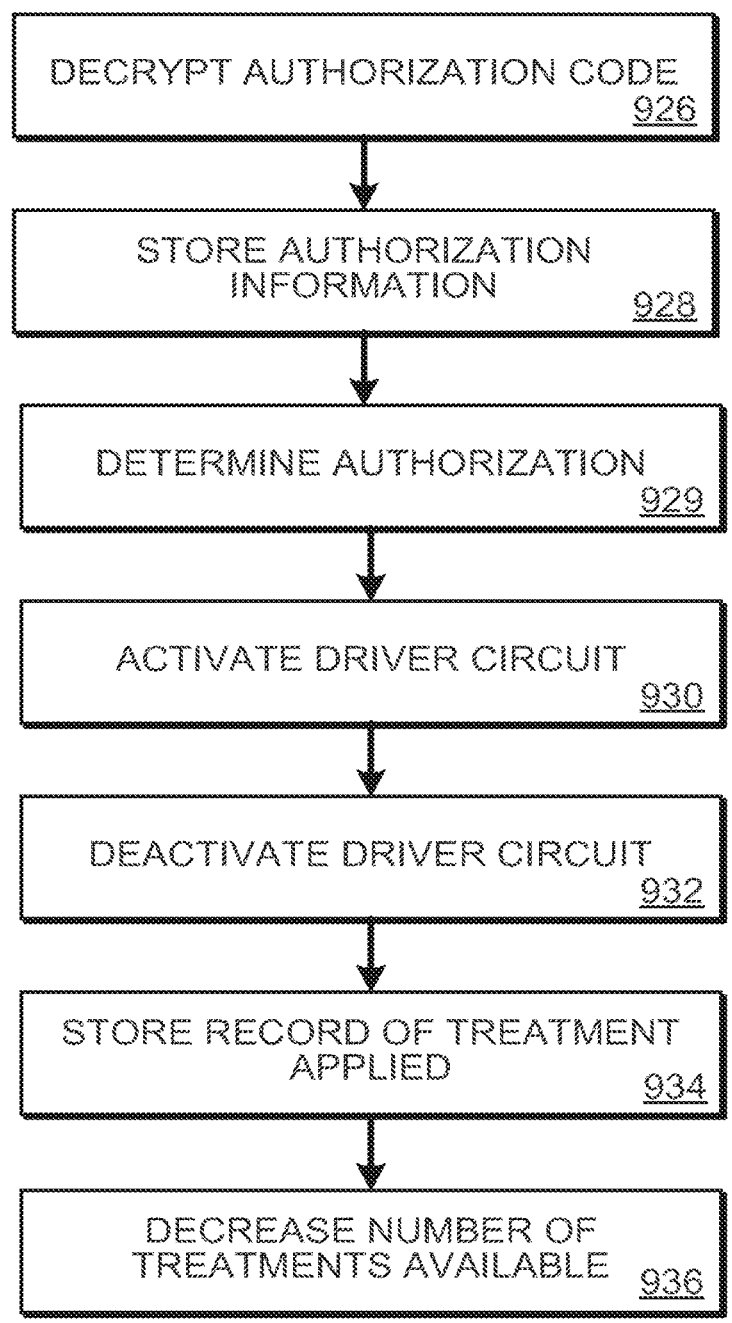

Referring to FIG. 9B, the medical device can decrypt or decode the authorization code (926). In one implementation, the medical device may decrypt the authorization code using a unique device identifier or decryption key stored on the medical device. The medical device may determine that an authorization code is authentic or intended for the particular medical device that received it. The medical device may determine, using decrypted or decoded data, what treatments are authorized. For example, the medical device may determine that a particular number of treatments are authorized. The medical device may also determine that treatment using the medical device should be modified in some way, for example, that two treatments are authorized each day instead of one treatment each day, or that the intensity of ultrasound produced should be changed.

The medical device can store authorization information (928). For example, the medical device can store the number of treatments that the authorization code indicates should be authorized. The medical device can also store the authorization code received, the authorization information extracted from the received data, and other authorization information. In some instances, treatments using the medical device can be authorized without any input or action by the patient. For example, when a third-party payer sends payment to the server system, the medical device can be authorized without involvement from the patient.

The medical device can determine whether treatment is authorized (929). For example, the medical device can determine whether treatment is authorized based on the authorization code that was accessed by the medical device. The medical device can determine whether treatment authorized in response to receiving user input that treatment should be provided, in (902) or through later inputs. In the situation that the patient has attempted treatment with the medical device in (902), and subsequently entered payment needed to authorize treatment in (906), the medical device can proceed to apply the treatment after the determination is made that treatment is authorized. For example, the payment and authorization process may occur quickly so that the patient perceives very little delay between entering payment and the initiation of treatment. In one implementation, treatment may begin automatically when the patient has previously attempted to initiate treatment. Treatment may alternatively be delayed until the patient imitates treatment again or confirms that treatment should proceed.

If the determination indicates that treatment is authorized, the medical device can control a driver circuit to apply treatment (930). For example, the medical device may control an ultrasound transducer driver circuit in a manner that causes one or more ultrasound transducers to produce ultrasound with therapeutic properties. For example, the driver circuit can be activated to drive one or more ultrasound transducers. The driver circuit may continue to drive the ultrasound transducers until treatment is complete. Of course, if the determination indicates that treatment is not authorized based on the authorization code (for example, if the authorization code is for a different medical device, or if the treatments authorized by that code have already been expended), the medical device can control the driver circuit so that treatment is not applied, for example, by not activating the driver circuit so that treatment is prevented.

The driver circuit can be deactivated when treatment is finished (932). The medical device can store a record of the treatment applied (934). The medical device can also decrease the number of treatments authorized for the medical device (936). For example, if the medical device had received an authorization code that authorized twenty treatments of the medical device, after one treatment is completed, the medical device may update the number of authorized treatments to reflect that only nineteen treatments are currently authorized for the medical device.

Figure 10:
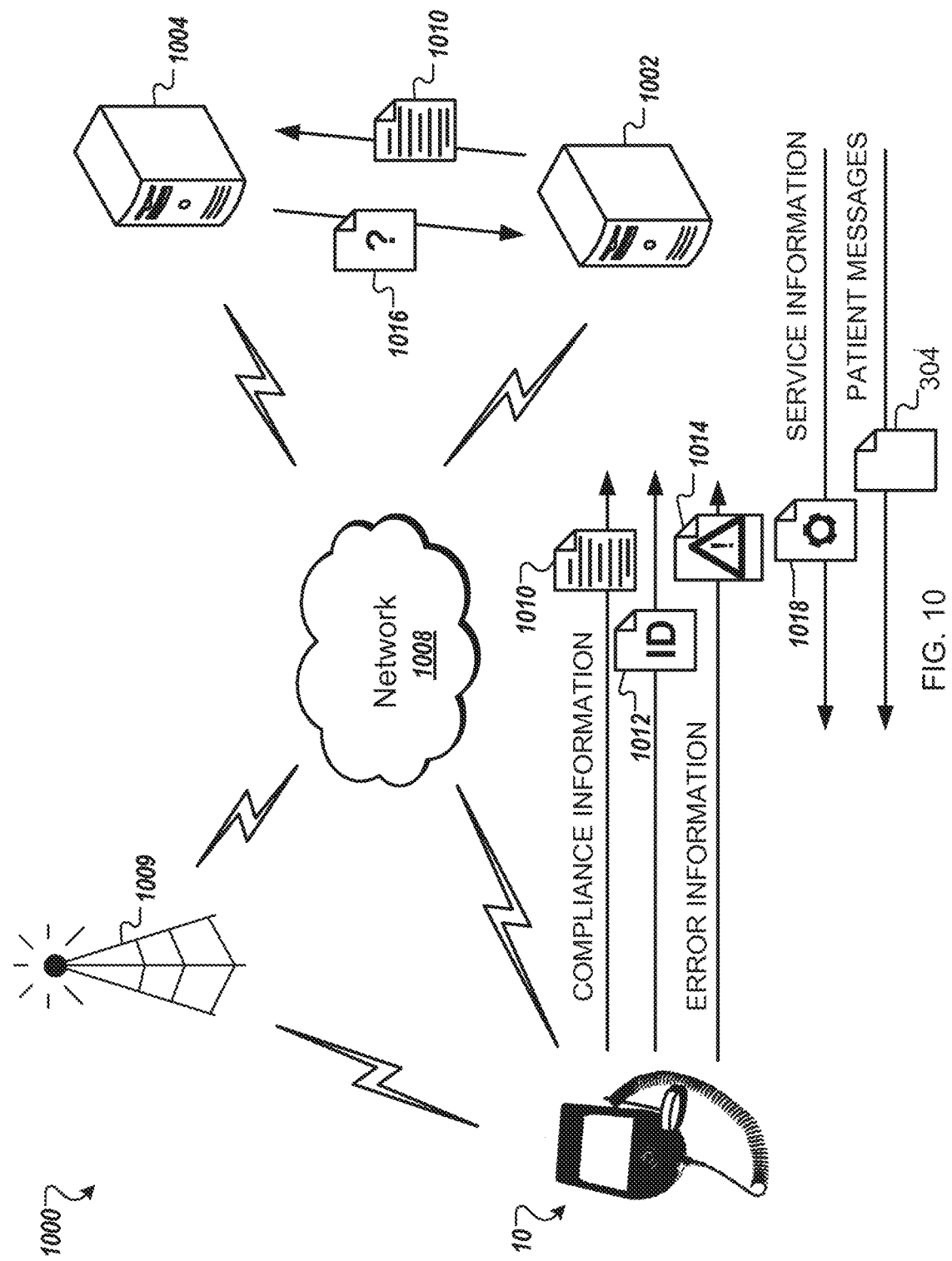
FIG. 10 is a diagram illustrating a system for collecting information related to a medical device.

Referring to FIG. 10, an example of a system 1000 for collecting compliance information includes the medical device 10, a server system 1002, and a third-party system, all connected by a network 1008. The medical device 10 and the server system 1002 may, additionally or alternatively, communicate through a cellular network 1009.

The medical device 10 can record use of the medical device 10, for example, by recording the date, time, and duration that treatment occurs using the medical device 10. The recorded use of the medical device 10 can be collected as compliance information 1010. For example, the medical device 10 can collect information about multiple treatments performed or multiple aspects of treatment.

As described above, in some implementations, the medical device 10 may receive information about the treatment regimen for the patient. For example, the treatment regimen may be entered on the device after the health condition has been diagnosed or after the medical device 10 has been prescribed to the patient. The compliance information 1010 may, but is not required to, include one or more results of a comparison between the recorded use of the medical device 10 and the treatment regimen of the patient.

To distinguish the medical device 10 from other medical devices 10, the medical device 10 may store a device identifier 1012 that enables the medical device 10 to be identified. For example, the device identifier 1012 may uniquely identify a particular medical device 10.

The medical device 10 can send the compliance information 1010 to the server system 1002. Compliance information 1010 can be sent automatically, for example, after a predefined number of treatments are performed, after a particular amount of time has elapsed, or after a treatment regimen has been completed. The medical device 10 may send the compliance information 1010 over the network 1008. Additionally, or alternatively, medical device 10 may send the compliance information 1010 over a cellular network 1009. The medical device 10 can also send the device identifier 1012 to the server system 1002 with the compliance information 1010, enabling the server system 1002 to associate the compliance information 1010 with the particular device. In addition to a device identifier, or alternatively, the medical device 10 may send a patient identifier with the compliance information 1010.

The server system 1002 can be configured to receive the compliance information 1010 and the device identifier 1012 from the medical device 10. The server system 1002 can determine a patient identifier using the device identifier 1012. For example, the server system 1002 may store records that associate device identifiers 1012 for multiple medical devices 10 with patient identifiers. The server system 1002 can compare the received device identifier 1012 to stored device identifiers to determine a patient identifier and identify the patient that uses the medical device 10. The server system can store the compliance information 1010 in association with the determined patient identifier.

The server system 1002 can be configured to receive compliance information from multiple medical devices 10 operated by different patients. For example, the server system 1002 may include a compliance database of many patients and information about the prescriptions and medical devices 10 that correspond to each patient. The server system 1002 can receive and record compliance information from each or any of patients or medical devices 10 described in the compliance database. The server system 1002 can add information about additional patients and medical devices 10 to the compliance database records.

The server system 1002 can provide access to the stored compliance information 1010 to one or more parties that have a relationship with the patient. For example, an insurance company for the patient may use the compliance information 1010 to determine whether the patient is using the medical device 10 that the insurance company paid for. A physician or a caretaker of the patient may use compliance information 1010 to determine if the patient is complying with a treatment regimen that has been prescribed. To obtain compliance information 1010 for the patient, a third-party system 1004 may submit an inquiry requesting the compliance information 1010 to the server system 1002. For example, the inquiry 1016 may include one or more patient identifiers to identify one or more patients. The server system 1002 can provide access to the compliance information 1010 for one or more users in response to receiving the inquiry from the third-party system 1004.

Because the server system 1002 can store compliance information about multiple patients and multiple medical devices 10, the server system 1002 can provide aggregate information about multiple patients and medical devices 10. For example, the server system 1002 may provide an insurance provider with a summary of the treatments performed for all patients covered by the insurance provider. As another example, a physician may receive compliance information for each of his patients from the server system 1002, without being required to interface with each of the prescribed medical devices 10 individually.

Summaries, reports, graphs, and comparisons can be provided based on compliance data for multiple patients, including, for example, information about a set or subset of patients. For example, the compliance of patients that have a particular health condition can be provided.

Access to the compliance information 1010 can be limited based on the relationship of the third party to the patient. The server system 1002 can store records that associate various third parties with various patients. The third party system 1004 may be required to be authenticated or comply with other security measures before access to compliance information 1010 is provided. Access to compliance information 1010 can also be limited by restricting the quantity or detail of information available. For example, one third party may receive more detailed compliance information 1010 than a different third party may receive for the same patient. For example, an insurance company for the patient may be provided access only to the number of treatments performed with the medical device 10, but the physician of the patient may be provided access to the particular dates and times that treatments occurred in addition to the total number of treatments.

The medical device 10 can also detect and record information about errors of the medical device 10. During treatment or during other operation of the medical device 10, one or more errors may occur. The medical device can store information about the errors as error information 1014, and can send the error information 1014 to the server system 1002 with the device identifier 1012. In one implementation, error information 1014 can be sent soon after the error is detected. Examples of errors that can be detected, and for which information can be recorded and sent, include a gel error indicating that there is insufficient ultrasound conductive gel on a transducer, a battery error that indicates that remaining power of the battery is low, and a connectivity error that indicates that a wire to a transducer is disconnected or broken.

The server system 1002 can be configured to receive the error information 1014 and the device identifier 1012. The server system 1002 can store the received error information 1014 and can associate error information 1014 with the device identifier 1012. The received error information 1014 may quickly and accurately indicate which medical devices 10 and which types of medical devices 10 experience errors and at what frequency errors occur.

The received error information may also enable the server system 1002 to provide information to the medical device 10 to address the errors. For example, the server system 1002 may use error information 1014 to determine a possible cause of an error. The server system 1002 may select service information 1018 that addresses the error. For example, the server system 1002 may select information to store on the medical device 10, which may include information to restore or replace outdated or incorrect information. The server system 1002 may select control instructions to be executed on the medical device 10, for example, control instructions to clear an error or to reinitialize the medical device 10. The server system 1002 can send the selected service information 1018 that addresses one or more errors to the medical device 10. The service information 1018 can include, for example, software or firmware updates, instructions to the user of the medical device 10, instructions to trained service personnel, and/or control instructions to alter the functioning of the medical device 10 and modules coupled to the medical device 10.

The medical device 10 can send information including one or more messages 304 to the medical device 10. The messages 304 may be stored on the medical device 10 and displayed to the patient during treatment. The messages 304 can include updated information or additional information to add to the variety of messages 304 already stored on the medical device 10. In addition, one or more messages 304 can be provided to instruct the patient how to correct an error of the medical device 10, or to inform the patient that an error has been corrected.

Figure 11:
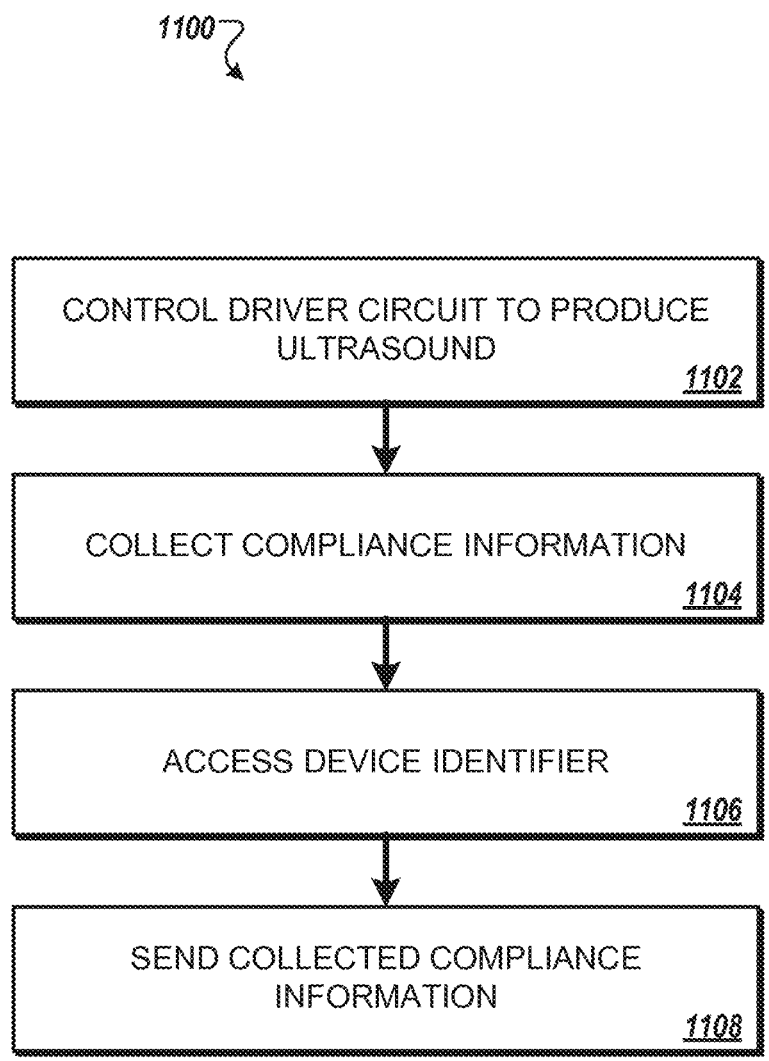
FIG. 11 is a flow diagram illustrating a process for sending information from a medical device.

Referring to FIG. 11, a medical device 10 may collect and send information as illustrated in the process 1100. The processing device 50 of the medical device 10 may, for example, execute instructions stored on the storage device 52 to perform the process 1100.

A driver circuit is controlled to produce ultrasound with therapeutic properties (1102).

Compliance information is collected (1104). Collecting compliance information can include recording information about use of the medical device, for example recording the number of treatments that are performed. Compliance information can include a number of treatments provided by the medical device, a date and time that a treatment was provided by the medical device, and/or a duration that a treatment was provided by the medical device. Information about multiple uses or treatments with the medical device can be collected.

A treatment regimen that identifies a prescribed use of the medical device can be identified. For example, information about a treatment regimen may be entered on the medical device or received from a network, which may include a cellular network. The information about the recorded use of the medical device can be compared to the information about the prescribed use of the medical. Information indicating the degree that the recorded use matches the prescribed use can be generated.

A device identifier can be accessed (1106). The device identifier can be stored on the medical device. The compliance information can be sent (1108). The accessed device identifier can be sent with the compliance information. For example, the compliance information can be sent to a server system configured to receive the compliance information. Compliance information can be sent automatically after a predetermined number of treatments have been performed. Compliance information may be sent using a wireless module, and the wireless module can include a cellular transceiver. For example, compliance information may be sent to a server system over a cellular network using the cellular transceiver. The medical device can include a SIM card that associates a particular telephone number with the medical device.

One or more errors of the medical device can be detected. Information about the detected errors can be sent with the accessed device identifier to a server system. Service information to address the detected errors can be received from the server system.

Figure 12:
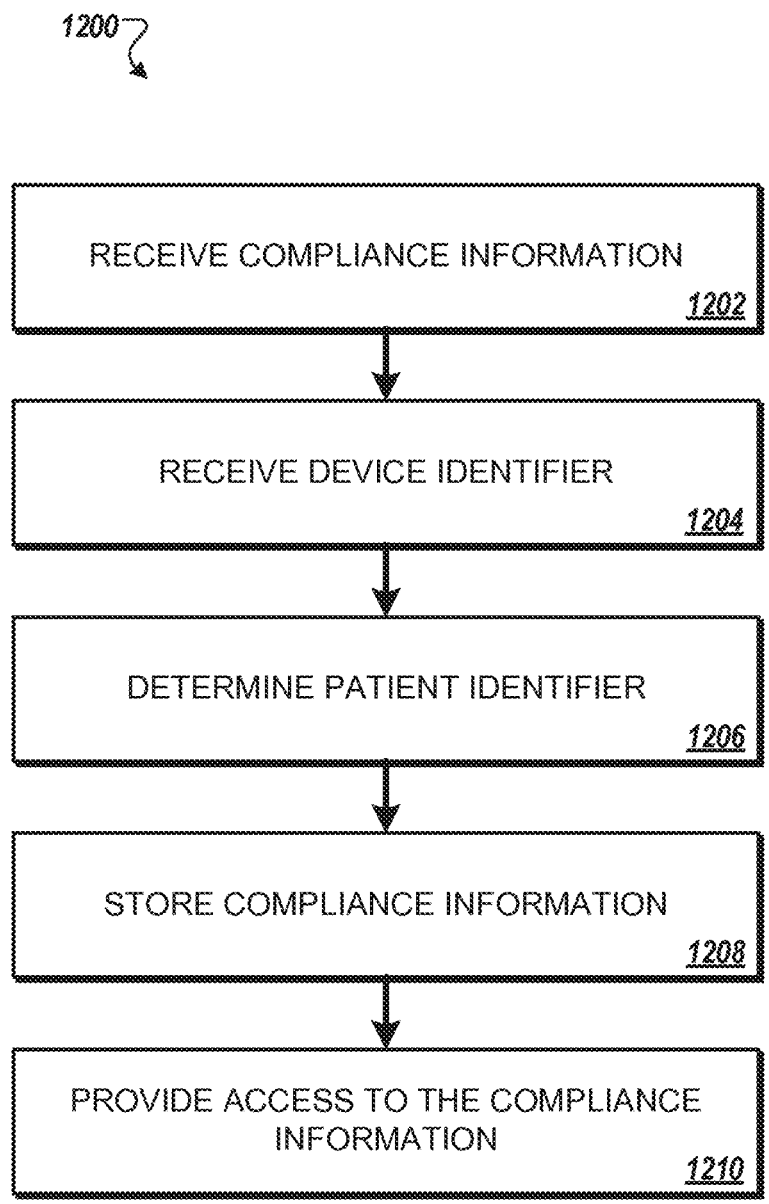
FIG. 12 is a flow diagram illustrating a process for collecting information.

Referring to FIG. 12, a server system can process information according to the illustrated process 1200. For example, one or more storage devices can store instructions that, when executed by one or more processing devices, cause the server system to perform the process 1200.

Compliance information can be received (1202). For example, compliance information can be received over a network or cellular network from one or more medical devices. Compliance information for multiple medical devices operated by different patients can be received. For example, the server system may be configured to receive compliance information from each of a plurality of patients, and each patient can be associated with at least one of a plurality of medical devices. The compliance information can include a number of treatments provided by a medical device, a date and time that a treatment was provided by the medical device, and/or a duration that a treatment was provided by the medical device. Compliance information can be received for multiple medical devices operated by different patients.

A device identifier can be received (1204). The device identifier can be received with the compliance information. A patient identifier can be determined (1206). For example, the received device identifier can be used to determine the patient identifier. The server system can store records that associate device identifiers with one or more patient identifiers. The recorded device identifiers can be compared to the received device identifier to determine a recorded device identifier that matches the received device identifier.

The compliance information can be stored (1208). The compliance information can be stored in association with the patient identifier that was determined to correspond to the compliance information. For example, the server system may be configured to store compliance information for each of a plurality of patients, and each patient can be associated with at least one of a plurality of medical devices. Compliance information for each patient can be stored in association with one or more device identifiers and/or patient identifiers.

Access to the compliance information can be provided (1210). For example, access may be provided to one or more users of the server system. Users may submit an inquiry to the server system, and the inquiry can be associated with a patient identifier. Users can include, for example, one or more of a representative of an insurance provider of the patient, a physician of the patient, and a caretaker of the patient. Access to the compliance information for a particular patient can be provided to the users in response to receiving the inquiry that is associated with the patient identifier for the particular patient. Access to the compliance information can be limited based on the relationship of the user to the patient.

For example, a physician of the patient may receive access to only a portion of the compliance information, such as only the number of times the medical device was used. A physician, on the other hand, may receive access to more detailed compliance information, such as the date, time, and duration that the medical device was used.

Because compliance information for multiple patients and multiple medical devices can be stored, access to compliance information for multiple patients and multiple medical devices can be provided. For example, compliance information can be provided to a third party for treatment performed by multiple medical devices operated by multiple patients.

Users that can receive access to the compliance information can include, for example, one or more caretakers, physicians, and representatives of insurance providers for any of the multiple patients whose compliance information is stored. Access can be provided to compliance information for each of a plurality of patients, where each patient is associated with at least one of a plurality of medical devices. Access to the compliance information for a particular patient can be provided to the users in response to receiving the inquiry that is associated with the patient identifier for the particular patient.

Information about one or more errors of the medical device can be received. Based on the information about the errors, service information to address the errors can be selected and transmitted to the medical device. One or more messages for the patient can be transmitted to the medical device.

Figure 13:
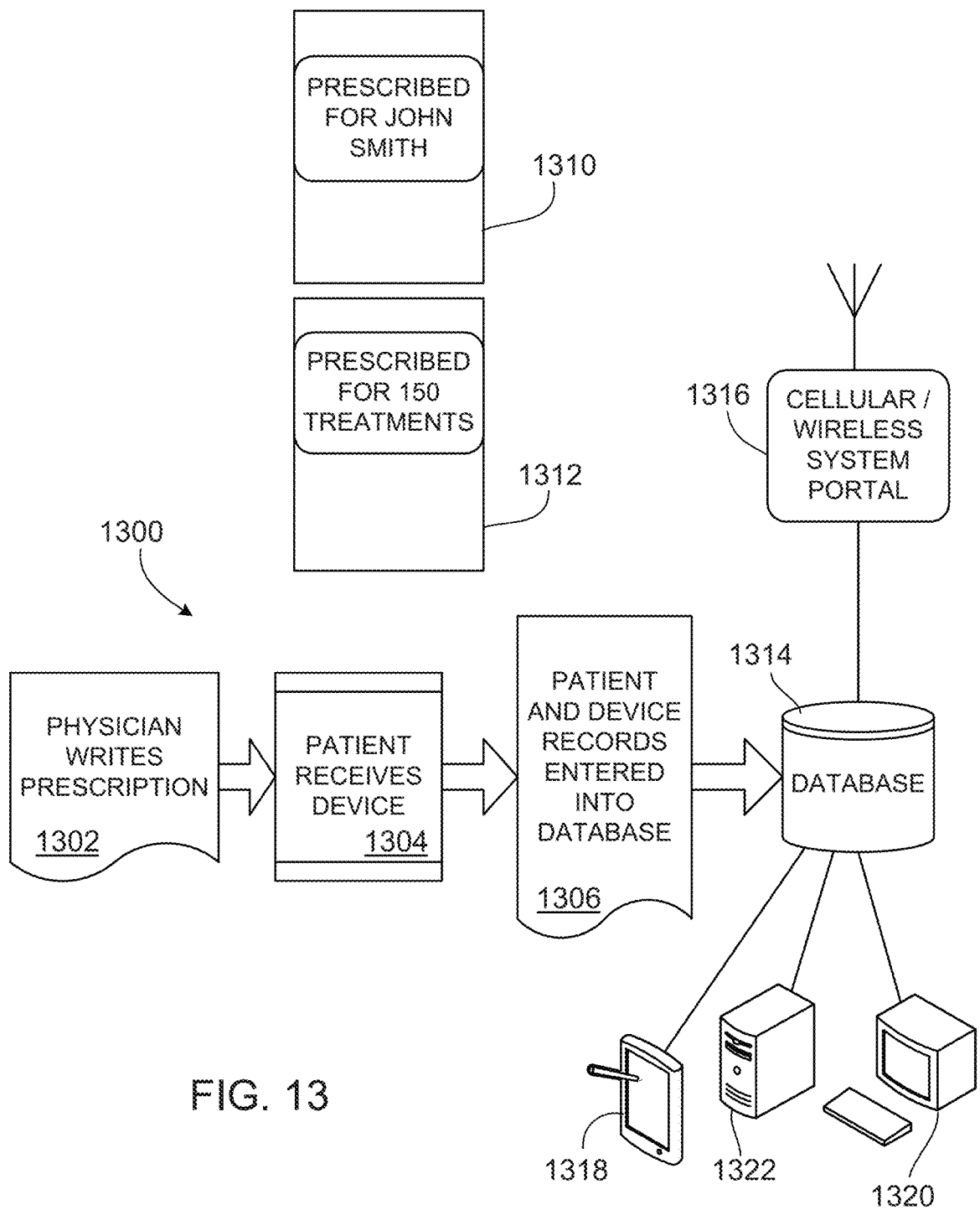
FIG. 13 is a diagram of a process for storing patient information.

Referring to FIG. 13, a process 1300 for storing patient information can begin with a physician writing a prescription for a patient for treatment using a medical device (1302). To carry out the prescribed treatment, a medical device can be dispensed to the patient (1304). The medical device can be authorized at the time the medical device is dispensed or at a later time.

Records for the patient and the dispensed medical device can be entered into a database 1314 (1306). For example, the database 1314 may store a patient record 1310 that associates a particular medical device or treatment with a particular patient, in the example, a patient named "John Smith." The database 1314 may also store a prescription record 1312 that indicates the number of treatments that can be purchased for the patient. The number of treatments indicated in a prescription record 1312 may be authorized for application by the medical device after payment has been received for the prescribed treatments. For example, the treatments can be enabled after a third-party payer agrees to pay for the treatments or after the patient enters payment at the medical device. The database 1314 may also store other records including records that identify patient identifiers and medical device identifiers. The information in the database can be accessed by one or more client devices 1318, 1320, a server system 1322, or other systems. For example, the server system 1322 may use the patient record 1310 to match payment to a particular medical device or patient. The records stored in the database 1314 may also be used to inform a third-party payer or patient the number of treatments that should be purchased to enable a treatment plan to be carried out.

Figure 14:
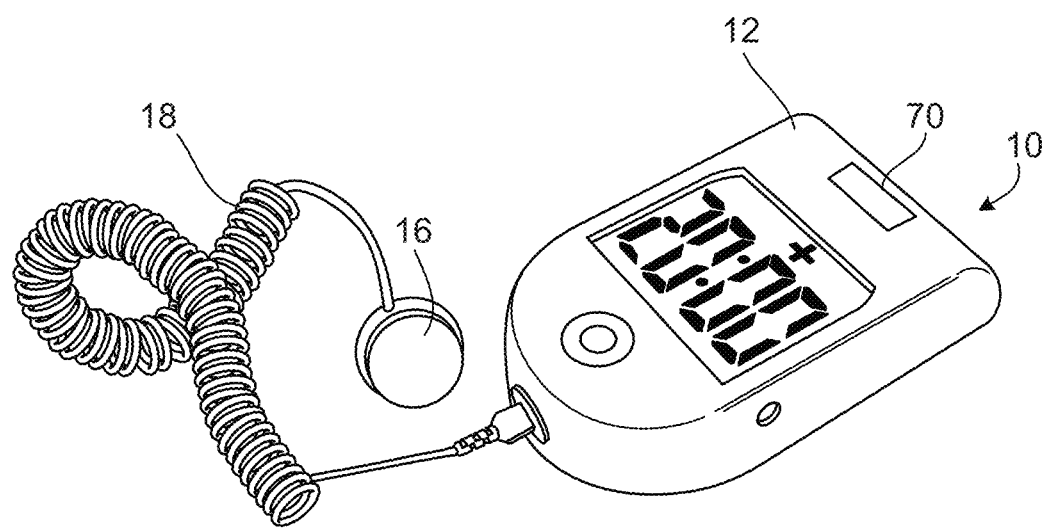
FIG. 14 is a diagram of the medical device.

Referring to FIG. 14, the authorized use of the medical device 10 can be limited to a particular patient and/or geographic area. In some instances, it is desirable by an automated method to limit the use of a medical device by an unauthorized person or in an unauthorized geographic area, such as in a country where the device has not received regulatory approval or in which an unauthorized sale of the device circumvents the chain of distribution of the device. Other examples where "geolocking" of a medical device may be desirable is where devices are sold at different price points in different regions and it is desirable to limit the ability of a lower priced device to be sold in a higher priced region, where device have region specific chargers, include specific languages, or are designed for single patient use or multiple patient use such as in some hospitals.

It is also desirable to limit a single patient use device from being shared with other than the intended patient by, for example, resale or shared use with friends or family members, particularly where the device is a prescription device. The desire to limit such use is particularly applicable to medical devices such as the Exogen™ Ultrasound Bone Healing System sold by Smith & Nephew, Inc. that is easily transported.

Figure 15:
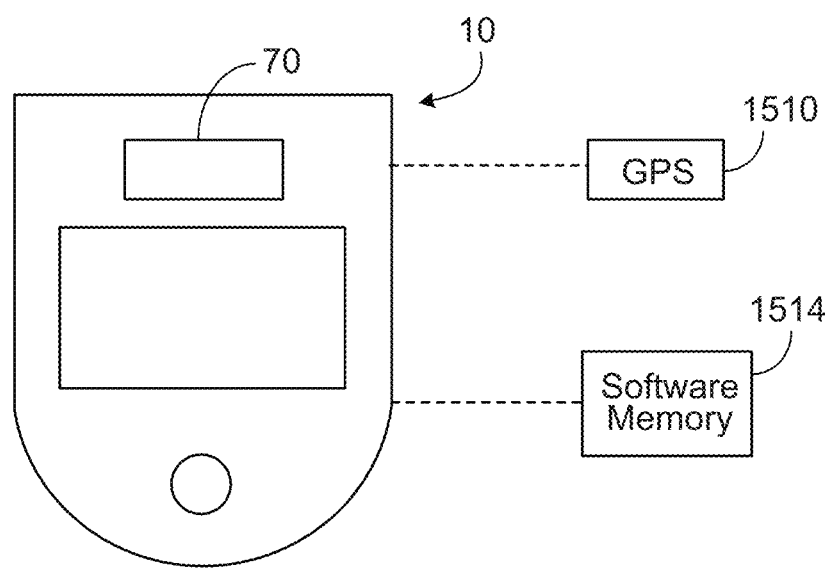
FIG. 15 is a diagram of a main operating unit of the medical device.

To limit, and preferably prevent, the use of a medical device 10 (FIG. 14) in an unauthorized geographic area, the medical device 10 includes hardware and software that determine the geographical location of the medical device 10 upon start-up and compare the determined geographical location to an authorized geographical location. The authorized geographical location can be, for example, programmed in the medical device 10 during the manufacturing process. Referring to FIG. 15, the medical device 10 include a GPS receiver 1510 to determine geographical location, and memory 1514 to store authorized operating areas for the medical device 10. Alternatively, the medical device 10 can use cell phone networks or Wi-Fi to determine geographical location.

Figure 16:
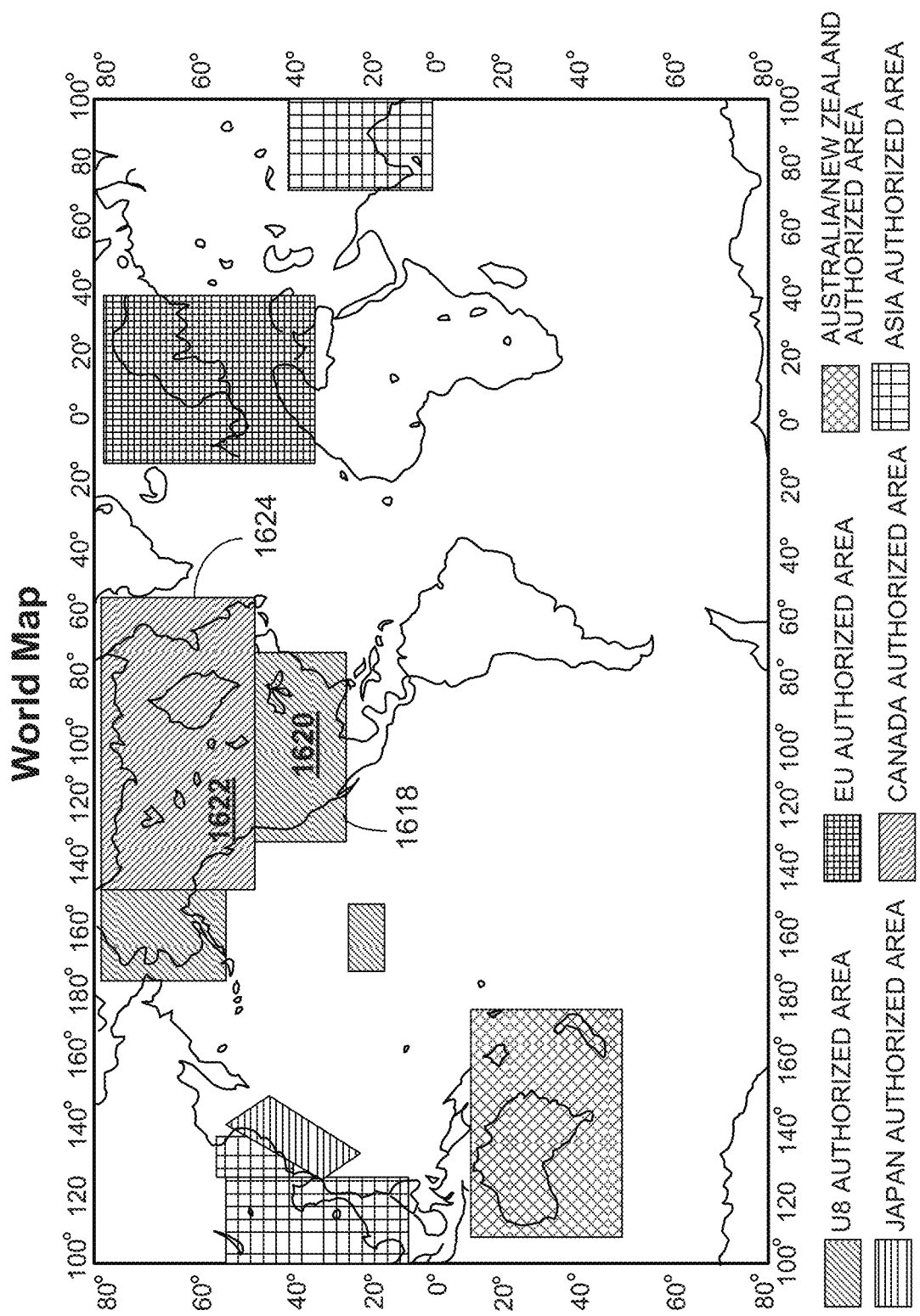
FIG. 16 shows authorized geographic areas.

Referring to FIG. 16, the location of the medical device 10 is compared to an approved area 1618 in which treatment is authorized. If the geographical location 1620 of the device 10 is within the authorized area 1618, treatment begins. If the geographical location 1622 of the device 10 is in an unauthorized area 1624, no treatment is delivered. The device can include two-way communication, such as cellular, internet or wireless communication. To accommodate patient travel, the medical device 10 can be configured to accept over-the-air-updates to the authorized geographical location.

Figure 17:
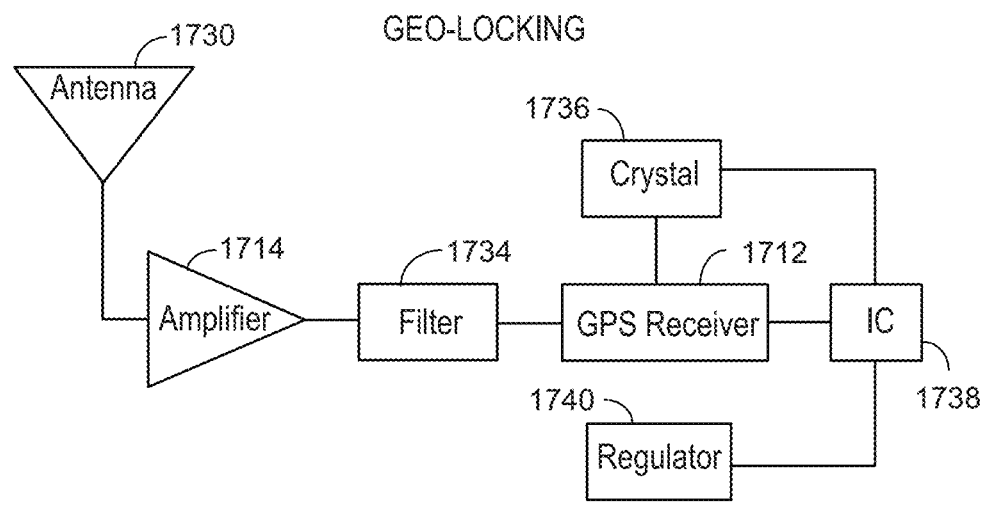
FIG. 17 is a block diagram of geo-locking components of the medical device.

As illustrated in FIG. 17, for "geolocking" purposes, the medical device 10 includes the GPS receiver 1712, an antenna 1730 connected to the GPS receiver 1712 via an amplifier 1732 and a filter 1734, and a crystal 1736, an integrated circuit 1738, and a regulator 1740.

Advantageously, a medical device can be designed for use within only a specific geographical area, for example, a country or region as illustrated in FIG. 16, such that use of the device in unintended markets is limited or prevented.

To limit, and preferably prevent, the use of the medical device 10 by an unauthorized person, the medical device 10 requires proof of patient identity using, for example, a key card or token issued to the user, a password, or physical evidence. For example, referring to FIG. 2, the medical device 10 includes hardware and software and a user interface 70 implemented on the device to identify the patient using a fingerprint, retinal scan, or voice recognition.

The identity of the user is compared to the stored patient identity and treatment is only authorized when the user is confirmed to be the patient.

Figure 18:
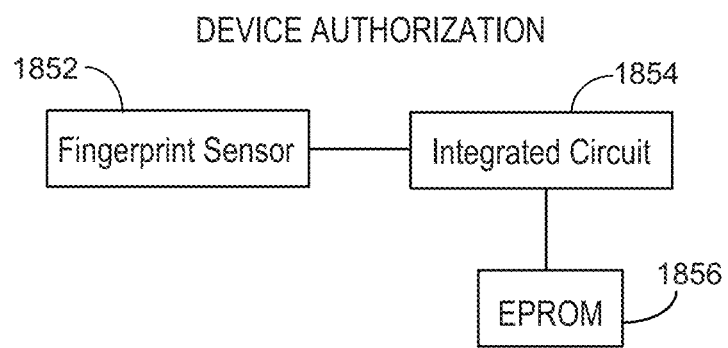
FIG. 18 is a block diagram of device authorization components of the medical device.

As illustrated in FIG. 18, for device authorization purposes, the medical device 10 includes, for example, a fingerprint sensor 1852, control electronics such as an integrated circuit 1854, and an EPROM 1856.

Advantageously, the use of a fingerprint, retinal scan, or voice recognition ensures that the patient is at least present during the treatment. In situations where the patient is, for example, young or elderly, the identity of a supervising individual can alternatively or additionally be required. The fingerprint, voice or retinal scan of the authorized user is saved into the memory of the device when the device is prescribed and fitted by a responsible party, for example, a doctor, pharmacist or sales representative.

Figure 19:
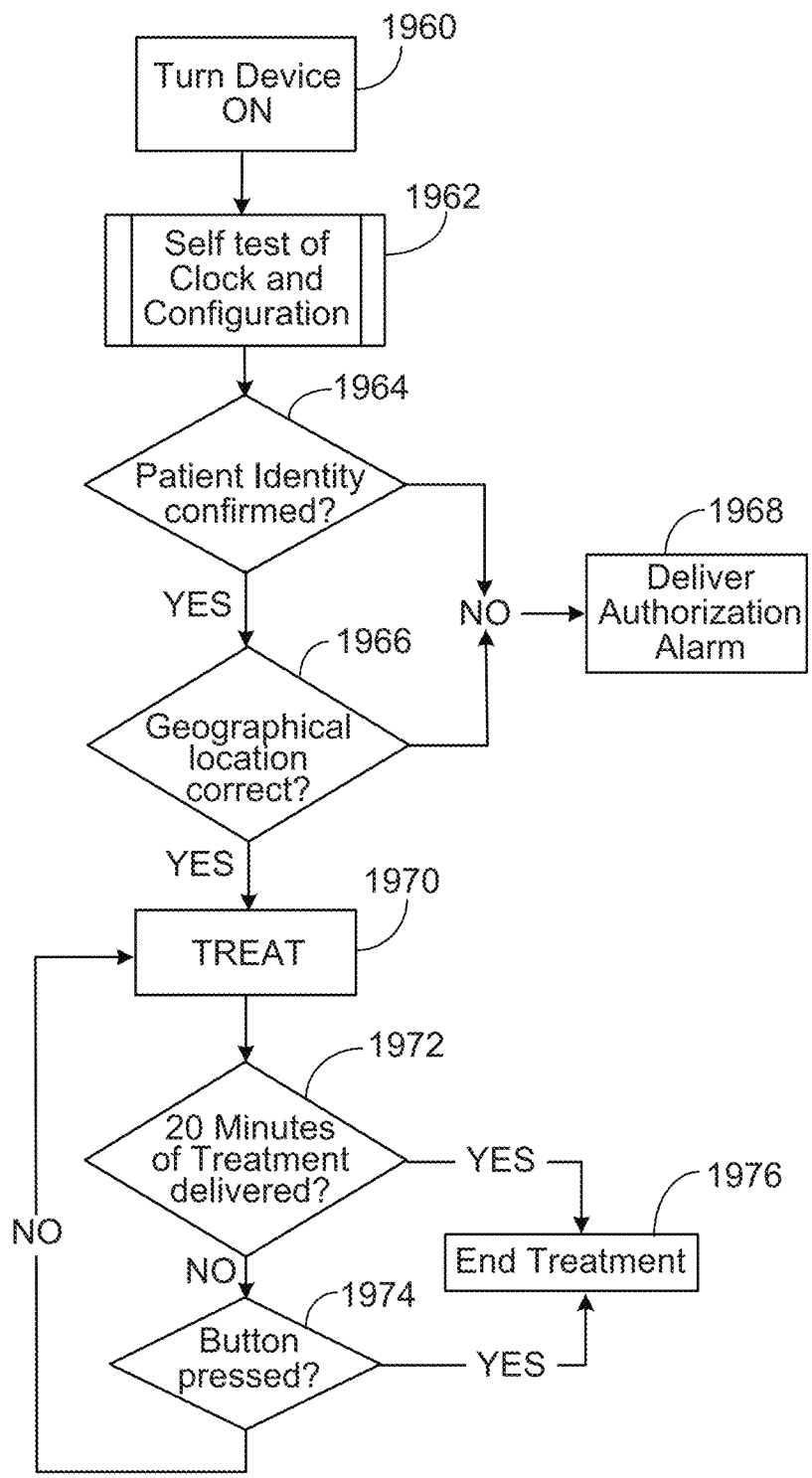
FIG. 19 is a flowchart depicted use of the medical device.

Referring to FIG. 19, a method for limiting unauthorized use of the medical device 10 includes determining the geographic location of the medical device 10 and not allowing treatment to commence if the determined geographic location is outside an authorized geographic location, and/or includes determining user identity and not allowing treatment to commence if the determined user identity does not match an authorized identity. The medical device 10 includes means for determining the geographic location of the medical device 10 and means for determining user identity. Treatment is not allowed to commence if either the determined geographic location is outside an authorized geographic location or the determined user identity does not match an authorized identity.

In use, the patient turns the device 10 on at step 1960, the device performs a self-test of the clock and configuration at step 1962, the patient, for example, scans his or her index finger over the fingerprint sensor 1852, and the device confirms the patient identity at step 1964. If the patient is the authorized user, the geographical location of the device is checked at step 1966. If the patient is not the authorized user, an authorization alarm is delivered at step 1968 and treatment will not commence. If the patient is the authorized user and the device 10 is within its authorized geographical location treatment can be started at step 1970. If the device 10 is not within its authorized geographical location, an authorization alarm is delivered at step 1968 and treatment will not commence.

At steps 1972, 1974 and 1976, the device 10 monitors the time of use, allowing up to 20 minutes of treatment to be delivered before ending treatment.

Figure 20:
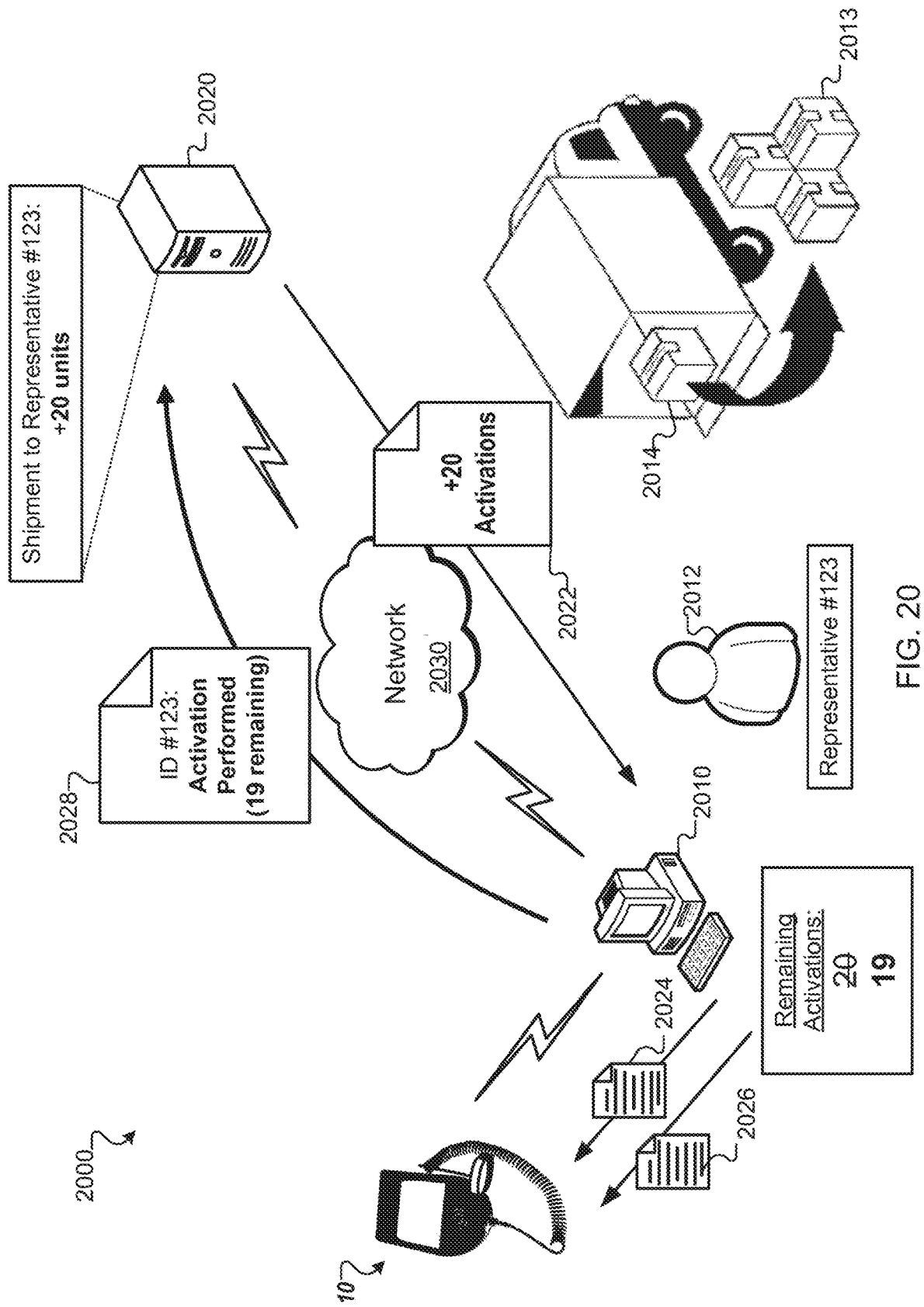

Referring to FIG. 20, an inventory tracking and medical device activation system 2000 can be used to control the distribution of medical devices 10. The system 2000 includes an enabling device 2010 that communicates with the medical device 10. The enabling device 2010 also communicates with a server 2020 over a network 2030.

Each medical device 10 can be provided to a distributor or physician in a disabled or deactivated state. For example, the medical device 10 can be provided in a state in which no treatments are authorized. Additionally, the medical device 10 can be provided in a state in which treatments cannot be purchased or authorized, until the medical device 10 is activated and thus made operative by an enabling device. Because the medical devices 10 are shipped and stored in inventory in an inoperative state, the potential for unauthorized use is very low.

The enabling device 2010 includes the capability to activate medical devices 10. For example, the enabling device 2010 can include an activation module including a wireless or wired communication system to transmit activation information. The server 2020, however, can limit the enabling device 2010. For example, the server 2020 can authorize the enabling device 2010 to activate only a limited number of medical devices 10. The total number of medical device activations that the enabling device can be performed can be limited (e.g., no more than 10 activations, until further authorization is received). Additionally, or alternatively, the number of activations that can be performed over a particular period of time can be limited (e.g., no more than 10 activations per month). As described in further detail below, the server 2020 can limit the number of medical device activations that the enabling device 2010 can perform so that, at any given time, the enabling device 2010 is authorized to perform a number of medical device activations no greater than the number of medical devices in a particular inventory 2013 of a particular sales representative 2012. The enabling device 2010 is associated with the sales representative 2012, and a unique identifier for the enabling device 2010 or for the representative 2012 associates the enabling device 2010 with the inventory 2013 of the representative 2012.

The server 2020 tracks the inventories of multiple representatives. The server 2020 can identify changes in inventories using information from reliable sources, for example, information that is verifiable or outside the control of the representatives. For example, the server 2020 receives information from manufacturers or distributors of medical devices about shipments of products to the representatives.

Based on the inventory 2013 for the representative 2012, the server 2020 adjusts the ability of the enabling device 2010 to activate medical devices 10. For example, the server 2020 authorizes the enabling device 2010 to activate as many medical devices 10 as are in the official inventory 2013 for the representative 2012. For example, when the medical devices 10 are shipped to the representative 2012, the server 2020 receives information about the shipment 2014 from the manufacturer or distributor. In response to determining that the inventory 2013 for the representative 2012 has increased, the server 2020 transmits to the representative's enabling device 2010 an authorization code 2022 permitting a number of medical device 10 activations corresponding to the size of the shipment 2014. If twenty medical devices 10 are shipped to the representative 2012, the server 2020 sends an authorization code 2022 permitting the enabling device 2010 to activate up to twenty medical devices 10.

When the medical device 10 is purchased or dispensed to a patient, the sales representative 2012 can activate the medical device 10 using the enabling device 2010. The enabling device 2010 communicates with the medical device 10 over a wired link or a wireless link, such as Bluetooth. For example, the enabling device 2010 supplies an activation code 2024 to the medical device 10 that unlocks the functionality of the medical device 10. The enabling device 2010 can also supply an authorization code 2026 that authorizes a particular number of treatments to be performed with the medical device 10. The activation code 2024 and the authorization code 2026 can be combined in a single message or code. After the medical device 10 receives the activation code 2024, the medical device 10 determines whether the activation code 2024 is valid to activate the medical device 10 and/or one or more of its treatment modules. In response to determining that the activation code 2024 is valid, the medical device 10 may send an activation confirmation message (not shown) to the enabling device 2010 to indicate that activation was successful.

After the enabling device 2010 activates the medical device 10, the enabling device 2010 automatically decreases the number of activations that the enabling device 2010 can provide. For example, the number of activations permitted is decreased by one, from twenty to nineteen. The number of activations can be decreased in response to receiving the activation confirmation message from the medical device 10 so that the number is decreased only after successful activation attempts.

Once the activations allowed by the authorization code 2022 are exhausted, the enabling device 2010 is restricted from activating additional medical devices 10. The representative 2012 is thus restricted from activating medical devices 10 beyond those legitimately in the representative's inventory 2013. When a new shipment of medical devices 10 is sent to the representative 2012, the server 2020 transmits a new authorization code that permits the enabling device 2010 to activate the medical devices 10 in the new shipment.

In some implementations, the server 2020 can also communicate with the enabling device 2010 to reduce the number of activations allowed, for example, if the inventory 2013 of the representative 2012 decreases due to returning unused medical devices to the manufacturer. Accordingly, the number of activations that can be provided by the enabling device 2010 is maintained according to the current inventory 2013 of the representative 2012.

In some implementations, the enabling device 2010 sends a message 2028 to the server 2020 that indicates when an activation of a medical device 10 has occurred, allowing the server 2020 to monitor activations. The remaining number of activations currently allowed by the enabling device 2010 can also be included in the message 2028.

In some implementations, after the medical device 10 expends all of the treatments authorized by the authorization code 2026, a second authorization code can be received to permit additional treatments to be performed. As described above, the second authorization code can be received in response to payment by a patient or a patient's insurance provider. The second authorization code can be received, for example, over the network 2030, from the enabling device 2010, or from a removable medium.

By contrast, in some implementations, the medical device 10 returns to an inoperative, deactivated state after the treatments authorized by the authorization code 2026 are exhausted. Thus the medical device 10 must be activated with an activation code from the enabling device 2010 before further treatments are permitted.

The medical device 10 can be configured to transmit information indicating usage of the medical device 10, including compliance with a treatment regimen, to the enabling device 2010 over the same communication link used to receive the activation code. Thus, as part of the exchange, the medical device 10 receives a new activation code from the enabling device 2010, and the enabling device 2010 receives usage information from the medical device 10. The enabling device 2010 can then transmit the usage information to the server 2020, with identifiers to identify, for example, the patient, prescription, and medical device 10 associated with the usage information.

In some implementations, rather than being enabled by a transmission of an activation code from an enabling device, a medical device can be activated by a code accessed from a removable medium, such as an SD memory card.

Referring to FIG. 21, the system 2000 can also control medical device activations and treatment authorizations based on prescriptions and insurance payment authorizations. For example, the enabling device 2010 can be limited to activating a medical device when a valid prescription for the medical device is received, or when an insurance company authorizes payment for a prescribed medical device.

The enabling device 2010 can be configured to require an authorization code before performing each activation. Each time a medical device is activated, a new authorization code is required. The server 2020 provides authorization codes over the network 2030. The server 2020 can provide an authorization code allowing the activation of a single medical device based on a particular prescription for the medical device. If no prescription is submitted to the server 2020, the server 2020 does not send an authorization code to the enabling device 2010, and the enabling device 2010 is unable to activate medical devices.

For example, after a physician issues a prescription for treatment using the medical device 10, the prescription can be entered on the enabling device 2010, which transmits identifying information 2115 identifying the prescription to the server 2020. For example, the enabling device 2010 transmits a representative identifier and a prescription identifier in the identifying information 2115. The identifying information 2115 may be additionally or alternatively transmitted by the medical device 10, a physician's computer system, an insurance company computer system, or other system. In some implementations, the identifying information 2115 can identify the prescription, the patient receiving the prescription, the doctor or office issuing the prescription, an insurance company for the patient, an insurance policy for the patient, the representative 2012, the medical device 10 to be activated, and/or the enabling device 2010, and the information can be stored by the server 2020.

The server 2020 verifies the prescription information, for example, by comparing the prescription information to other prescription records or by verifying an authentication signature in the received information. The server 2020 can also communicate with another server system 2110, such as a server for an insurance company of the patient, to determine whether payment has been authorized for the prescription.

If the prescription is determined to be valid, and/or if payment has been authorized, the server 2020 transmits an authorization code 2120 to the enabling device 2010. The authorization code 2120 permits the enabling device 2010 to activate a single medical device 10 for the patient and prescription that were verified. The enabling device 2010 transmits an activation code 2124 to the medical device 10. The enabling device 2010 also transmits an authorization code 2126 to the medical device 10, permitting the medical device 10 to apply the number of treatments indicated in the prescription, or the number of treatments for which payment was authorized by the insurance company.

The enabling device 2010 can transmit information to the server 2020 indicating that the activation of the medical device 10 was performed. Based on the initial identifying information 2115 and/or information received subsequent to the activation, the server 2020 can record the transaction identifying, for example, the patient, the prescription, the medical device 10, the representative 2012, the enabling device 2010, and the authorization code 2120 associated with the activation.

When no prescription is submitted to the server 2020, the server 2020 does not send an authorization code to the enabling device 2010, and the enabling device 2010 cannot activate the medical device 10. Similarly, if the prescription information sent to the server 2020 is invalid or is not verifiable, or if payment is refused by an insurance provider, the server 2020 can withhold the authorization code, disallowing the activation of the medical device 10.

In a similar manner, the system 2000 can be used to track and/or evaluate passes for unpaid treatments. In some implementations, the enabling device 2010 can be authorized to provide a limited number of complimentary medical device activations or treatment authorizations for previously activated medical devices 10. Each time a pass is provided, the enabling device 2010 transmits information to the server 2020 identifying, for example, the physician, representative 2012, medical device 10, and insurance provider associated with the pass. The information may also identify the patient and prescription associated with the pass. The server 2020 can thus maintain a database tracking the issuance of complimentary passes for different representatives 2012, physicians, and insurance providers.

In some implementations, the enabling device 2010 can be limited to providing passes when the server 2020 provides authorization for each pass individually. For example, the server 2020 can evaluate the circumstances of a particular patient and a particular prescription to determine whether the patient qualifies for complimentary or reduced cost treatment.

The enabling device 2010 transmits a request to the server 2020 that indicates the circumstances of the desired pass. The request can indicate, for example, the medical condition to be treated, the identity of the patient, an associated prescription, the patient's income or other financial status, whether and to what degree treatment is covered by insurance, and what insurance provider covers the treatment. The request can also identify the physician, representative 2012, enabling device 2010, and medical device 10 associated with the request.

The server 2020 receives and evaluates the request for the pass. For example, the server 2020 uses the information in the request to evaluate the patient's medical needs, economic circumstances, and other circumstances to determine whether to authorize the activation and treatment authorization of a medical device for the patient. If the patient's circumstances meet the criteria for complimentary treatment, the server 2020 sends an authorization code to the enabling device 2010 permitting the enabling device 2010 to provide a pass for the particular patient. If the patient does not qualify for a pass, the server system 2020 withholds the authorization code necessary to activate a medical device or authorize additional treatments for the medical device. The server 2020 can record each request for a pass, each pass granted, and activations and treatments that occur based on the pass.

The techniques described above are not limited to any particular hardware or software configuration. Rather, they may be implemented using hardware, software, or a combination of both. The methods and processes described may be implemented as computer programs that are executed on programmable computers comprising at least one processor and at least one data storage system. The programs may be implemented in a high-level programming language and may also be implemented in assembly or other lower level languages, if desired.

Any such program will typically be stored on a computer-usable storage medium or device (e.g., CD-ROM, RAM, or magnetic disk). When read into the processor of the computer and executed, the instructions of the program cause the programmable computer to carry out the various operations described above.

A number of implementations have been described. Nevertheless, it will be understood that various modifications may be made. For example, the described features of presentation of messages selected for a particular patient, the collection and display of compliance information, and treatment authorization, and medical device locking based on identity or geographical location may be implemented for a single medical device. In addition, any subset of the features described can be implemented. Each of the message presentation, compliance information collection and display, treatment authorization, and medical device locking features may be implemented individually, separate from the other features described, or together in any combination.

Accordingly, other implementations are within the scope of the following claims.

The invention claimed is:

1. A medical device configured to communicate with a remote computer system, the medical device comprising:
 a treatment source configured to apply a therapy to damaged tissue of a patient to facilitate healing of the damaged tissue; and
 one or more processing devices configured to:
  receive, via a wireless network or a user input, a treatment regimen that identifies a scheduled use of the treatment source;

responsive to receiving an activation code to enable the therapy, control the treatment source to apply the therapy to the damaged tissue in accordance with the treatment regimen;

generate usage information indicative of the therapy applied by the treatment source;

compare the usage information and the scheduled use;

generate compliance information reflecting a degree that the usage information matches the scheduled use; and send the compliance information with a device identifier to a remote computer system, thereby causing the remote computer system to:

determine a patient identifier based upon the device identifier;

store the compliance information in association with the patient identifier; and provide access to the compliance information to one or more users in response to receiving an inquiry associated with the patient identifier from the one or more users.

2. The medical device of claim 1, wherein:
the treatment source comprises a driver circuit coupled to an ultrasound transducer; and
the one or more processing devices are configured to control the driver circuit to produce ultrasound with the ultrasound transducer.

3. The medical device of claim 1, wherein the compliance information comprises at least one of:
a number of times that the therapy was applied by the treatment source;
a date or a time that the therapy was applied by the treatment source; or
a duration that the therapy was applied by the treatment source.

4. The medical device of claim 1, wherein the one or more processing devices are further configured to:
detect one or more errors; and
send error information about the one or more errors with the device identifier to the remote computer system.

5. The medical device of claim 4, wherein the one or more processing devices are further configured to receive service information from the remote computer system to address the one or more errors.

6. The medical device of claim 1, wherein the one or more processing devices are configured to send the compliance information with the device identifier after the treatment source has applied the therapy a set number of times.

7. The medical device of claim 1, wherein the one or more processing devices are further configured to determine whether the activation code is valid prior to controlling the treatment source to apply the therapy.

8. The medical device of claim 7, wherein the one or more processing devices are further configured to transmit an activation acknowledgement if the activation code is determined to be valid.

9. The medical device of claim 1, wherein the activation code includes activation information indicative of a number of times that the therapy is to be applied by the treatment source.

10. The medical device of claim 1, wherein the one or more processing devices are further configured to transmit an activation acknowledgement.

11. The medical device of claim 1, wherein the treatment regimen identifies the scheduled use of the treatment source by the patient rather than another individual, and the treatment regimen indicates to apply the therapy a plurality of times.

12. The medical device of claim 1, wherein the wireless network comprises a cellular network.

13. The medical device of claim 1, wherein the device identifier identifies at least one of the treatment source or the one or more processing devices.

14. The medical device of claim 1, in combination with the remote computer system.

15. A method of operating a medical device, the method comprising:
receiving, via a wireless network or a user input to the medical device, a treatment regimen that identifies a scheduled use of a treatment source, the treatment source being configured to apply a therapy to damaged tissue of a patient to facilitate healing of the damaged tissue;

receiving an activation code to enable the therapy;

in response to receiving the activation code to enable the therapy, controlling the treatment source to apply the therapy to the damaged tissue in accordance with the treatment regimen;

generating, by one or more processing devices of the medical device, usage information indicative of the therapy applied by the treatment source;

comparing, by the one or more processing devices, the usage information and the scheduled use;

generating, by the one or more processing devices, compliance information reflecting a degree that the usage information matches the scheduled use; and sending, by the one or more processing devices, the compliance information with a device identifier to a remote computer system, thereby causing the remote computer system to:

determine a patient identifier based upon the device identifier;

store the compliance information in association with the patient identifier; and provide access to the compliance information to one or more users in response to receiving an inquiry associated with the patient identifier from the one or more users.

16. The method of claim 15, wherein the treatment source comprises a driver circuit coupled to an ultrasound transducer and wherein the controlling the treatment source comprises controlling the driver circuit to produce ultrasound with the ultrasound transducer.

17. The method of claim 15, wherein the compliance information comprises at least one of:
a number of times that the therapy was applied by the treatment source;
a date or a time that the therapy was applied by the treatment source; or
a duration that the therapy was applied by the treatment source.

18. The method of claim 15, further comprising:
detecting one or more errors of the medical device; and
sending error information about the one or more errors with the device identifier to the remote computer system.

19. The method of claim 18, further comprising receiving, from the remote computer system, service information to address the one or more errors.

20. The method of claim 15, wherein the sending the compliance information with the device identifier is performed after the treatment source has applied the therapy a set number of times.

21. The method of claim 15, further comprising determining whether the activation code is valid prior to controlling the treatment source to apply the therapy.

22. The method of claim 21, further comprising transmitting an activation acknowledgement if the activation code is determined to be valid.

* * * * *